US008258179B2

(12) United States Patent
Yao et al.

(10) Patent No.: US 8,258,179 B2
(45) Date of Patent: *Sep. 4, 2012

(54) CRYSTALLINE FORM OF A (3S)-AMINOMETHYL-5-METHYL-HEXANOIC ACID PRODRUG AND METHODS OF USE

(75) Inventors: Fenmei Yao, Mountain View, CA (US); Mark A. Gallop, Palo Alto, CA (US); Ronald W. Barrett, Saratoga, CA (US); Peter A. Virsik, Portola Valley, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/962,472

(22) Filed: Dec. 7, 2010

(65) Prior Publication Data

US 2011/0224295 A1 Sep. 15, 2011

Related U.S. Application Data

(63) Continuation of application No. 12/358,454, filed on Jan. 23, 2009, now Pat. No. 7,872,046.

(60) Provisional application No. 61/023,808, filed on Jan. 25, 2008, provisional application No. 61/023,813, filed on Jan. 25, 2008, provisional application No. 61/121,859, filed on Dec. 11, 2008.

(51) Int. Cl.
*A61K 31/27* (2006.01)
*C07C 271/22* (2006.01)
*C07C 269/08* (2006.01)

(52) U.S. Cl. ........................................ 514/478; 514/479

(58) Field of Classification Search .................. None
See application file for complete search history.

(56) References Cited

U.S. PATENT DOCUMENTS

| 4,024,175 | A | 5/1977 | Satzinger et al. |
| 4,126,684 | A | 11/1978 | Robson et al. |
| 4,760,057 | A | 7/1988 | Alexander |
| 4,916,230 | A | 4/1990 | Alexander |
| 5,006,560 | A | 4/1991 | Kreutner et al. |
| 5,563,175 | A | 10/1996 | Silverman et al. |
| 5,684,018 | A | 11/1997 | Alexander |
| 5,719,185 | A | 2/1998 | Bountra et al. |
| 6,020,370 | A | 2/2000 | Horwell et al. |
| 6,028,214 | A | 2/2000 | Silverman et al. |
| 6,103,932 | A | 8/2000 | Horwell et al. |
| 6,117,906 | A | 9/2000 | Silverman et al. |
| 6,117,908 | A | 9/2000 | Andrews et al. |
| 6,562,865 | B1 | 5/2003 | Codd et al. |
| 6,818,787 | B2 | 11/2004 | Gallop et al. |
| 6,927,036 | B2 | 8/2005 | Gallop et al. |
| 6,972,341 | B2 | 12/2005 | Gallop et al. |
| 7,026,351 | B2 | 4/2006 | Gallop et al. |
| 7,109,239 | B2 | 9/2006 | Gallop et al. |
| 7,186,855 | B2 | 3/2007 | Gallop et al. |
| 7,227,028 | B2 | 6/2007 | Gallop et al. |
| 7,232,924 | B2 | 6/2007 | Raillard et al. |
| 7,300,956 | B2 | 11/2007 | Gallop et al. |
| 7,432,299 | B2 | 10/2008 | Taylor et al. |
| 7,491,835 | B2 | 2/2009 | Donevan et al. |
| 7,700,652 | B2 | 4/2010 | Barrett |
| 7,872,046 | B2 | 1/2011 | Yao et al. |
| 2004/0176456 | A1 | 9/2004 | Taylor, Jr. et al. |
| 2004/0254246 | A1 | 12/2004 | Barrett et al. |
| 2005/0070483 | A1 | 3/2005 | Donevan et al. |
| 2005/0090550 | A1 | 4/2005 | Barrett |
| 2005/0153946 | A1 | 7/2005 | Hirsh et al. |
| 2005/0192353 | A1 | 9/2005 | Barrett et al. |
| 2008/0161393 | A1 | 7/2008 | Barrett et al. |

FOREIGN PATENT DOCUMENTS

| GB | 2 374 595 | 10/2002 |
| WO | WO 92/09560 | 6/1992 |
| WO | WO 93/23383 | 11/1993 |
| WO | WO 97/29101 | 8/1997 |
| WO | WO 97/33858 | 9/1997 |
| WO | WO 97/33859 | 9/1997 |
| WO | WO 98/17627 | 4/1998 |
| WO | WO 99/08670 | 2/1999 |
| WO | WO 99/08671 | 2/1999 |
| WO | WO 99/21824 | 5/1999 |
| WO | WO 99/31057 | 6/1999 |
| WO | WO 99/31074 | 6/1999 |
| WO | WO 99/31075 | 6/1999 |
| WO | WO 99/61424 | 12/1999 |
| WO | WO 00/15611 | 3/2000 |
| WO | WO 00/31020 | 3/2000 |
| WO | WO 00/50027 | 8/2000 |
| WO | WO 00/61135 | 10/2000 |
| WO | WO 01/08675 | 2/2001 |
| WO | WO 01/13904 | 3/2001 |
| WO | WO 01/26638 | 4/2001 |
| WO | WO 02/00209 | 1/2002 |
| WO | WO 02/096404 | 12/2002 |

(Continued)

OTHER PUBLICATIONS

U.S. Appl. No. 12/266,169, filed Nov. 6, 2008, Benson et al.
U.S. Appl. No. 61/023,808, filed Jan. 25, 2008, Yao et al.
U.S. Appl. No. 61/023,813, filed Jan. 25, 2008, Yao et al.
U.S. Appl. No. 61/121,859, filed Dec. 11, 2008, Gallop et al.
Alexander et al., (Acyloxy)alkyl carbamate prodrugs of norfloxacin. *J. Med. Chem.* 1991, 34(1), 78-81.
Alexander et al., (Acyloxy)alkyl carbamates as novel bioreversible prodrugs for amines: increased permeation through biological membranes. *J. Med. Chem.* 1988, 31(2), 318-322.
Becker et al., Pregabalin is effective against behavioural and electrographic seizures during alcohol withdrawal. *Alcohol & Alcoholism* 2006, 41(4), 399-406.
Ben-David et al., Gabapentin therapy for vulvodynia. *Anesth, Analg.* 1999, 89, 1459-60.
Blommel et al., Pregabalin: an antiepileptic agent useful for neuropathic pain. *Am J Health Syst Pharm* 2007, 64(14), 1475-82.
Bowsher, Neurogenic pain syndromes and their management. *Br. Med. Bull.* 1991, 47(3), 644-66.

(Continued)

*Primary Examiner* — Joseph K. McKane
*Assistant Examiner* — Alicia L Otton
(74) *Attorney, Agent, or Firm* — Dorsey & Whitney LLP

(57) ABSTRACT

A crystalline form of a (3S)-aminomethyl-5-hexanoic acid prodrug and methods of preparing a crystalline form of a (3S)-aminomethyl-5-hexanoic acid prodrug, and methods of using a crystalline form of a (3S)-aminomethyl-5-hexanoic acid prodrug are provided.

21 Claims, 9 Drawing Sheets

FOREIGN PATENT DOCUMENTS

| | | |
|---|---|---|
| WO | WO 02/100347 | 12/2002 |
| WO | WO 2004/054565 | 7/2004 |
| WO | WO 2005/010011 | 2/2005 |
| WO | WO 2005/025563 | 3/2005 |
| WO | WO 2005/089872 | 9/2005 |
| WO | WO 2007/027476 | 3/2007 |
| WO | WO 2007/027477 | 3/2007 |
| WO | WO 2007/052999 | 5/2007 |
| WO | WO 2009/061934 | 5/2009 |

OTHER PUBLICATIONS

Brittain et al., Polymorphism in pharmaceutical dosage forms. *Polymorphism in Pharmaceutical Solids XX* (1999), pp. 235-238, 348-361.

Bryans et al., 3-Substituted GABA analogs with central nervous system activity: a review. *Med. Res. Rev.* 1999, 19(2), 149-177.

Bryans et al., Identification of novel ligands for the gabapentin binding site on the a2δ subunit of a calcium channel and their evaluation as anticonvulsant agents. *J. Med. Chem.* 1998, 41, 1838-1845.

Buvanendran et al., Preoperative cyclooxygenase-2 inhibitor treatment reduces the incidence of heterotopic ossification after hip arthroplasty: six-month follow-up. *Anesthesiology* 2007, 107(2), 358-359.

Ciccaglione et al., Effect of acute and chronic administration of the $GABA_B$ agonist baclofen on 24 hour pH metry and symptoms in control subjects and in patients with gastro-oesophageal reflux disease. *Gut* 2003, 52, 464-70.

Codd et al. Tramadol and several anticonvulsants synergize in attenuating nerve injury-induced allodynia. *Pain* 2008, 134, 254-262.

Coluzzi et al., Chronic non-cancer pain: focus on once-daily tramadol formulations. *Ther Clin Risk Manage* 2007, 3(5), 819-29.

Crofford et al., Pregabalin for the treatment of fibromyalgia syndrome: results of a randomized, double-blind, placebo-controlled trial. *Arthritis and Rheumatism* 2005, 52(4), 1264-73.

Dahl et al., Protective premedication: an option with gabapentin and related drugs? A review of gabapentin and pregabalin in the treatment of post-operative pain. *Acta Anesthesiol Scand* 2004, 48(8), 1130-36.

Dapas et al., Baclofen for the treatment of acute low-back syndrome—a double-blind comparison with placebo. *Spine* 1985, 10(4), 345-9.

Freedman et al., Pregabalin has opioid-sparing effects following augmentation mamaplasty. *Aesthetic Surgery J* 2008, 28(4), 421-424.

Freitag, Preventative treatment for migraine and tension-type headaches: do drugs having effects on muscle spasm and tone have a role? *CNS Drugs* 2003, 17(6), 373-81.

Freynhagen et al., Efficacy of pregabalin in neuropathic pain evaluated in a 12-week, randomized, double-blind, multicentre, placebo-controlled trial of flexible- and fixed-dose regimens. *Pain* 2005, 115(3), 254-63.

Fromm et al., Role of inhibitory mechanisms in trigeminal neuralgia. *Neurology* 1981, 31, 683-7.

Gatti et al., Controlled-release oxycodone and pregabalin in the treatment of neuropathic pain: results of a multicenter Italian study. *Eur Neurol* 2009, 61, 129-137.

Gilron, Gabapentin and pregabalin for chronic neuropathic and early postsurgical pain: current evidence and future directions. *Curr Opin Anaesthesiol* 2007, 20, 456-472.

Gogate et al., N-(Acyloxyalkoxycarbonyl) derivatives as potential prodrugs of amines. I. Kinetics and mechanism of degradation in aqueous solutions. *International Journal of Pharmaceutics* 1987, 40, 235-248.

Grond et al., Clinical pharmacology of tramadol. *Clin Pharmacokinet* 2004, 43(13), 879-923.

Guttuso et al., Gabapentin's effects on hot flashes in postmenopausal women: a randomized controlled trial. *Obstet. Gynecol.* 2003, 101(2), 337-345.

Guttuso, Gabapentin's effects on hot flashes and hypothermia. *Neurology* 2000, 54, 2161-2163.

Hanna et al., Prolonged-release oxycodone enhances the effects of existing gabapentin therapy in painful diabetic neuropathy patients. *Eur J Pain* 2008, 12, 804-13.

Heiss et al., Polyethylene glycol monomethyl ether-modified pig liver esterase: preparation, characterization and catalysis of enantioselective hydrolysis in water and acylation in organic solvents. *Tetrahedron Lett*. 1995, 36(22), 3833-3836.

Hill et al., Pregabalin in patients with postoperative dental pain. *Eur J Pain* 2001, 5, 119-124.

Hindmarch et al., A double-blind study in healthy volunteers to assess the effects on sleep of pregabalin compared with alprazolam and placebo. *Sleep* 2005, 28(2), 187-93.

Jeffery et al., Gabapentin for hot flashes in prostate cancer. *Ann. Pharmacother.* 2002, 36(3), 433-436.

Jokela et al., A randomized controlled trial of perioperative administration of pregabalin for pain after laparoscopic hysterectomy. *Pain* 2008, 134, 106-112.

Keskinbora et al., Gabapentin and an opioid combination versus opioid alone for the management of neuropathic cancer pain: a randomized open trial. *J Pain Symptom Manage* 2007, 34, 183-189.

Loprinzi et al., Pilot evaluation of gabapentin for treating hot flashes. *Mayo Clin. Proc.* 2002, 77, 1159-1163.

Mathew et al., Efficacy of gabapentin in migraine prophylaxis. *Headache* 2001, 41, 119-128.

Morissette et al., High-throughput crystallization: polymorphs, salts, co-crystals and solvates of pharmaceutical solids. *Adv. Drug. Deliv. Rev*. (2004), 56: pp. 275-300.

Pande et al., Efficacy of the novel anxiolytic pregabalin in social anxiety disorder: a placebo-controlled, multicenter study. *J Clin Psychopharmacol* 2004, 24(2), 141-149.

Pohl et al., Efficacy of pregabalin in the treatment of generalized anxiety disorder: double-blind, placebo-controlled comparison of BID versus TID dosing. *J Clin Psychopharmacol* 2005, 25(2), 151-8.

Price et al., Are baclofen-sensitive $GABA_B$ receptors present on primary afferent terminals of the spinal cord? *Nature* 1984, 307, 71-4.

Rao et al., Efficacy of gabapentin in the management of chemotherapy-induced peripheral neuropathy: a phase 3 randomized, double-blind, placebo-controlled, crossover trial (N00C3). *Cancer* 2007, 110(9), 2110-8.

Raphael et al., Efficacy and adverse effects of intravenous lignocaine therapy in fibromyalgia syndrome. *BMC Musculoskeletal Disorders* 2002, 3(17), Epub Jun. 20, 2002 (8 pages).

Reuben et al., Preventing the development of chronic pain after orthopedic surgery with preventative multimodal analgesic techniques. *J Bone Joint Sur Am*. 2007, 89, 1343-1358.

Reuben et al., The analgesic efficacy of celecoxib, pregabalin, and their combination for spinal fusion surgery. *Anesth Analg*. 2006, 103(5),1271-7.

Rickels et al., Pregabalin for treatment of generalized anxiety disorder: a 4-week, multicenter, double-blind, placebo-controlled trial of pregabalin and alprazolam. *Arch Gen Psychiatry* 2005, 62(9), 1022-1030.

Ringel et al., Glossopharyngeal neuralgia: successful treatment with baclofen. *Ann Neurol* 1987, 21(5), 514-5.

Ruoff et al., Tramadol/acetaminophen combination tablets for the treatment of chronic lower back pain: a multicenter, randomized, double-blind, placebo-controlled outpatient study. *Clinical Ther* 2003, 25(4), 1123-1141.

Ruppert et al., Activity enhancement of pig liver esterase in organic solvents by colyophilization with methoxypolyethylene glycol: kinetic resolution of alcohols. *Tetrahedron Asymmetry*, 1997, 8(21), 3657-3664.

Sabatowski et al., Pregabalin reduces pain and improves sleep and mood disturbances in patients with post-herpetic neuralgia: results of a randomized, placebo-controlled clinical trial. *Pain* 2004, 109, 26-35.

Saif, Successful amelioration of oxaliplatin-induced hyperexcitability syndrome with the antiepileptic pregabalin in a patient with pancreatic cancer. *Cancer Chemother Pharmacol* 2008, 61(3), 349-354.

Siddall et al., Pregabalin in central neuropathic pain associated with spinal cord injury: a placebo-controlled trial. *Neurology* 2006, 67(10), 1792-800.

Sommer et al., Pregabalin in restless legs syndrome with and without neuropathic pain. *Acta Neurol Scand* 2007, 115(5), 347-50.

Sun et al., N-Acyloxymethyl carbamate linked prodrugs of pseudomycins are novel antifungal agents. *Bioorganic & Medicinal Chemistry Letters* 2001, 11, 1875-1879.

Taylor et al., Pharmacology and mechanism of action of pregabalin: the calcium channel $\alpha 2$-$\delta$ subunit as a target for antiepileptic drug discovery. *Epilepsy Res* 2007, 73(2), 137-50.

Tiippana et al., Do surgical patients benefit from perioperative gabapentin/pregabalin? A systematic review of efficacy and safety. *Anesth Analg* 2007, 104, 1545-56.

Tzschentke et al., (−)-(1R,2R)-3-(3-Dimethylamino-1-ethyl-2-methyl-propyl)-phenol hydrochloride (Tapentadol HCl): a novel μ-opioid receptor agonist/norepinephrine reuptake inhibitor with broad-spectrum analgesic properties. *J Pharm Expt'l Ther* 2007, 323(1), 265-276.

Van Herwaarden et al., The effect of baclofen on gastro-oesophageal reflux, lower oesophageal sphincter function and reflux symptoms in patients with reflux disease. *Aliment. Pharmacol. Ther.* 2002, 16, 1655-62.

Vippagunta, Crystalline solids. *Adv. Drug Deliv. Rev.* (2001), 48: pp. 3-26.

Wessely et al., Preliminary results of a double blind study with the new migraine prophylactic drug gabapentin. *Cephalalgia* 1987, 7(Suppl 6), 477-478).

Woolf et al., Preemptive analgesia—treating postoperative pain by preventing the establishment of central sensitization. *Anesth Analg* 1993, 77(2), 362-79.

Zareba, Pregabalin: a new agent for the treatment of neuropathic pain. *Drugs Today* 2005, 41(8), 509-16.

Zuniga et al., Intrathecal baclofen is analgesic in patients with chronic pain. *Anesthesiology* 2000, 92(3), 876-880.

International Search Report, dated Aug. 18, 2009, issued in PCT Appl. No. PCT/US2009/031867 (5 pages).

Written Opinion of the International Searching Authority, dated Aug. 18, 2009, issued in PCT Appl. No. PCT/US2009/031867 (10 pages).

Restriction Requirement dated Oct. 28, 2009, U.S. Appl. No. 12/358,454, 10 pages.

Response to Election Requirement dated Nov. 25, 2009, U.S. Appl. No. 12/358,454, 4 pages.

Office Action dated Feb. 23, 2010, U.S. Appl. No. 12/358,454, 24 pages.

Response to Office Action dated Jun. 23, 2010, U.S. Appl. No. 12/358,454, 22 pages.

Notice of Allowance and Interview summary dated Sep. 7, 2010, 12 pages.

CRYSTALLINE FORM OF A (3S)-AMINOMETHYL-5-METHYL-HEXANOIC ACID PRODRUG AND METHODS OF USE

This application is a continuation of U.S. patent application Ser. No. 12/358,454, filed Jan. 23, 2009, now U.S. Pat. No. 7,872,046, which claims the benefit under 35 U.S.C. §119(e) of U.S. Provisional Application Serial Nos. 61/023,808 filed Jan. 25, 2008; 61/023,813 filed Jan. 25, 2008; and 61/121,859 filed Dec. 11, 2008, each of which is incorporated by reference in its entirety.

FIELD

A crystalline form of a (3S)-aminomethyl-5-hexanoic acid prodrug, pharmaceutical compositions comprising a crystalline form of a (3S)-aminomethyl-5-hexanoic acid prodrug, and methods of making a crystalline form of a (3S)-aminomethyl-5-hexanoic acid prodrug are disclosed. This crystalline form of a (3S)-aminomethyl-5-hexanoic acid prodrug may be used as a therapeutic agent in the treatment of certain diseases and disorders, including, for example, neuropathic pain, epilepsy, generalized anxiety disorder, fibromyalgia, migraine, hot flashes, restless legs syndrome, and sleep disorders.

BACKGROUND

In general, crystalline forms of drugs are preferred over amorphous forms of drugs, in part, because of their superior stability. For example, in many situations, an amorphous drug converts to a crystalline drug form upon storage. Because amorphous and crystalline forms of a drug typically have different physical/chemical properties, potencies and/or bioavailabilities, such interconversion is undesirable for safety reasons in pharmaceutical administration. A key characteristic of any crystalline drug substance is the polymorphism of such a material. Polymorphs are crystals of the same molecule which have different physical properties because the crystal lattice contains a different arrangement of molecules. The different physical properties exhibited by polymorphs can affect important pharmaceutical parameters such as storage, stability, compressibility, density (important in formulation and product manufacturing) and dissolution rates (important in determining bioavailability). Stability differences may result from changes in chemical reactivity (e.g., differential hydrolysis or oxidation, such that a dosage form discolors more rapidly when the dosage form contains one polymorph rather than another polymorph), mechanical changes (e.g., tablets crumble on storage as a kinetically favored crystalline form converts to a thermodynamically more stable crystalline form) or both (e.g., tablets of one polymorph are more susceptible to breakdown at high humidity). Solubility differences between polymorphs may, in extreme situations, result in transitions to crystalline forms that lack potency and/or are toxic. In addition, the physical properties of the crystalline form may be important in pharmaceutical processing. For example, a particular crystalline form may form solvates more readily or may be more difficult to filter and wash free of impurities than other forms (e.g., particle shape and size distribution might be different between one crystalline form relative to other forms).

Agencies such as the United States Food and Drug Administration closely regulate the polymorphic content of the active component of a drug in solid dosage forms. In general, the regulatory agency requires batch-by-batch monitoring for polymorphic drugs if anything other than the pure, thermodynamically preferred polymorph is marketed. Accordingly, medical and commercial reasons favor synthesizing and marketing solid drugs as the thermodynamically stable polymorph, substantially free of kinetically favored polymorphs.

(3S)-{[1-Isobutanoyloxyethoxy]carbonylaminomethyl}-5-methyl-hexanoic acid (1) is a prodrug of the GABA analog pregabalin, (3S)-aminomethyl-5-methyl-hexanoic acid (2), which has high bioavailability as pregabalin when dosed either orally or directly into the colon of a mammal (Gallop et al., U.S. Pat. No. 6,972,341; and Gallop et al., U.S. Pat. No. 7,186,855, each of which is incorporated by reference in its entirety).

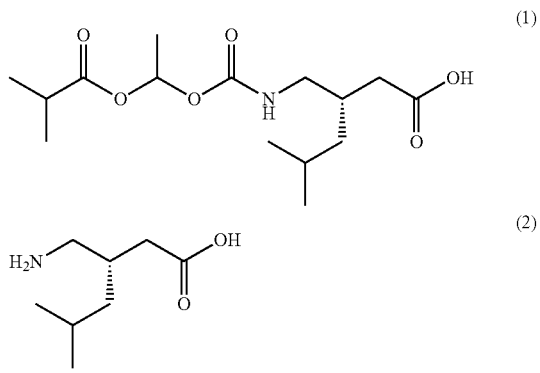

This high oral and/or colonic bioavailability makes this prodrug suitable for use in oral dosage forms (including sustained-release dosage forms) useful for treating diseases such as a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation.

Compound (1), prepared as disclosed in Gallop et al., U.S. Pat. No. 6,972,341 and Gallop et al., U.S. Pat. No. 7,227,028, consists of a mixture of two diastereomers ((1S)/(1R)) and is isolated as a thick oil after concentration from solutions in organic solvents. The oily nature of the materials obtained by this process disclosed in Gallop et al. is undesirable from the perspective of formulating stable, pharmaceutically acceptable oral dosage forms. Moreover, it has been found that transformation of the diastereomeric compounds to certain alkali metal salt forms (e.g., sodium salts) affords solid materials that are distinctly hygroscopic. Hygroscopic solids are difficult to handle using typical pharmaceutical processing conditions because of low bulk densities and unsatisfactory flow properties. Moreover, handling of hygroscopic solids requires special techniques and equipment to obtain, for example, reproducible amounts of active compound or solid formulation stability. Furthermore, drugs that are hygroscopic must be packaged in special containers that are impervious to water vapor, thus substantially increasing the cost of such products.

SUMMARY

Accordingly, a need exists for crystalline forms of (3S)-{[1-isobutanoyloxyethoxy]carbonylaminomethyl}-5-methyl-hexanoic acid (1) and pharmaceutically acceptable salts thereof with physicochemical properties that may be used advantageously in pharmaceutical processing and in pharmaceutical compositions.

A crystalline form of calcium (3S)-{[(1R)-isobutanoyloxyethoxy]carbonylaminomethyl}-5-methyl-hexanoate (3) is provided that satisfies this and other needs.

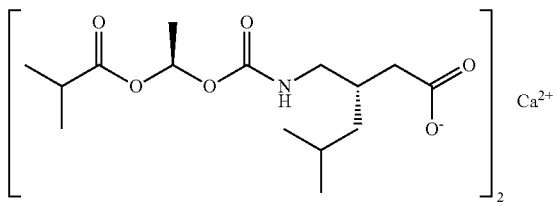

(3)

More specifically, crystalline calcium (3S)-{[(1R)-isobutanoyloxyethoxy]carbonylaminomethyl}-5-methyl-hexanoate hydrate (3a) and crystalline calcium (3S)-{[(1R)-isobutanoyloxyethoxy]carbonylaminomethyl}-5-methyl-hexanoate monohydrate are disclosed.

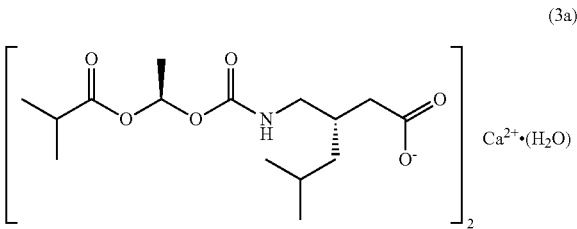

(3a)

In a first aspect, crystalline calcium (3S)-{[(1R)-isobutanoyloxyethoxy]carbonylaminomethyl}-5-methyl-hexanoate hydrate, which exhibits characteristic scattering angles (2θ) at least at 5.1°±0.2°, 7.3°±0.2°, 8.0°±0.2°, 11.6°±0.2°, 16.3°±0.2°, 17.3°±0.2°, and 19.2°±0.2° in an X-ray powder diffractogram measured using Cu—K$_\alpha$ radiation is provided.

In a second aspect, pharmaceutical compositions are provided comprising crystalline calcium (3S)-{[(1R)-isobutanoyloxyethoxy]carbonylaminomethyl}-5-methyl-hexanoate hydrate, which exhibits characteristic scattering angles (2θ) at least at 5.1°±0.2°, 7.3°±0.2°, 8.0°±0.2°, 11.6°±0.2°, 16.3°±0.2°, 17.3°±0.2°, and 19.2°±0.2° in an X-ray powder diffractogram measured using Cu—K$_\alpha$ radiation and a pharmaceutically acceptable vehicle.

In a third aspect, methods of preparing the compound crystalline calcium (3S)-{[(1R)-isobutanoyloxyethoxy]carbonylaminomethyl}-5-methyl-hexanoate hydrate, which exhibits characteristic scattering angles (2θ) at least at 5.1°±0.2°, 7.3°±0.2°, 8.0°±0.2°, 11.6°±0.2°, 16.3°±0.2°, 17.3°±0.2°, and 19.2°±0.2° in an X-ray powder diffractogram measured using Cu—K$_\alpha$ radiation are provided, by steps comprising providing a solution comprising calcium (3S)-{[(1R)-isobutanoyloxyethoxy]carbonylaminomethyl}-5-methyl-hexanoate, water, and a water-miscible solvent; and adjusting the temperature of the solution to provide crystalline calcium (3S)-{[(1R)-isobutanoyloxyethoxy]carbonylaminomethyl}-5-methyl-hexanoate hydrate.

In a fourth aspect, methods of treating a disease in a patient are provided comprising administering to a patient in need of such treatment a therapeutically effective amount of a pharmaceutical composition comprising crystalline calcium (3S)-{[(1R)-isobutanoyloxyethoxy]carbonylaminomethyl}-5-methyl-hexanoate hydrate, wherein the disease is chosen from a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation.

In a fifth aspect, kits are provided comprising a pharmaceutical composition comprising crystalline calcium (3S)-{[(1R)-isobutanoyloxyethoxy]carbonylaminomethyl}-5-methyl-hexanoate hydrate and instructions for administering the pharmaceutical composition to a patient in need thereof for treating a disease chosen from a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation.

In a sixth aspect, methods of modulating the α2δ subunit of the voltage-dependent calcium channel in a patient are provided comprising administering a pharmaceutical composition comprising crystalline calcium (3S)-{[(1R)-isobutanoyloxyethoxy]carbonylaminomethyl}-5-methyl-hexanoate hydrate to the patient.

In a seventh aspect, kits are provided comprising a pharmaceutical composition comprising crystalline calcium (3S)-{[(1R)-isobutanoyloxyethoxy]carbonylaminomethyl}-5-methyl-hexanoate hydrate, an agent chosen from an opioid agonist, a selective serotonin re-uptake inhibitor, and a selective noradrenaline re-uptake inhibitor, and instructions for administering the pharmaceutical composition to a patient in need thereof for managing chronic pain.

In an eighth aspect, methods of managing chronic pain in a patient are provided comprising administering to a patient in need of such treatment a pharmaceutical composition comprising crystalline calcium (3S)-{[(1R)-isobutanoyloxyethoxy]carbonylaminomethyl}-5-methyl-hexanoate hydrate, an agent chosen from an opioid agonist, a selective serotonin re-uptake inhibitor, and a selective noradrenaline re-uptake inhibitor, and a pharmaceutically acceptable vehicle.

DETAILED DESCRIPTION

Definitions

Figure 1:
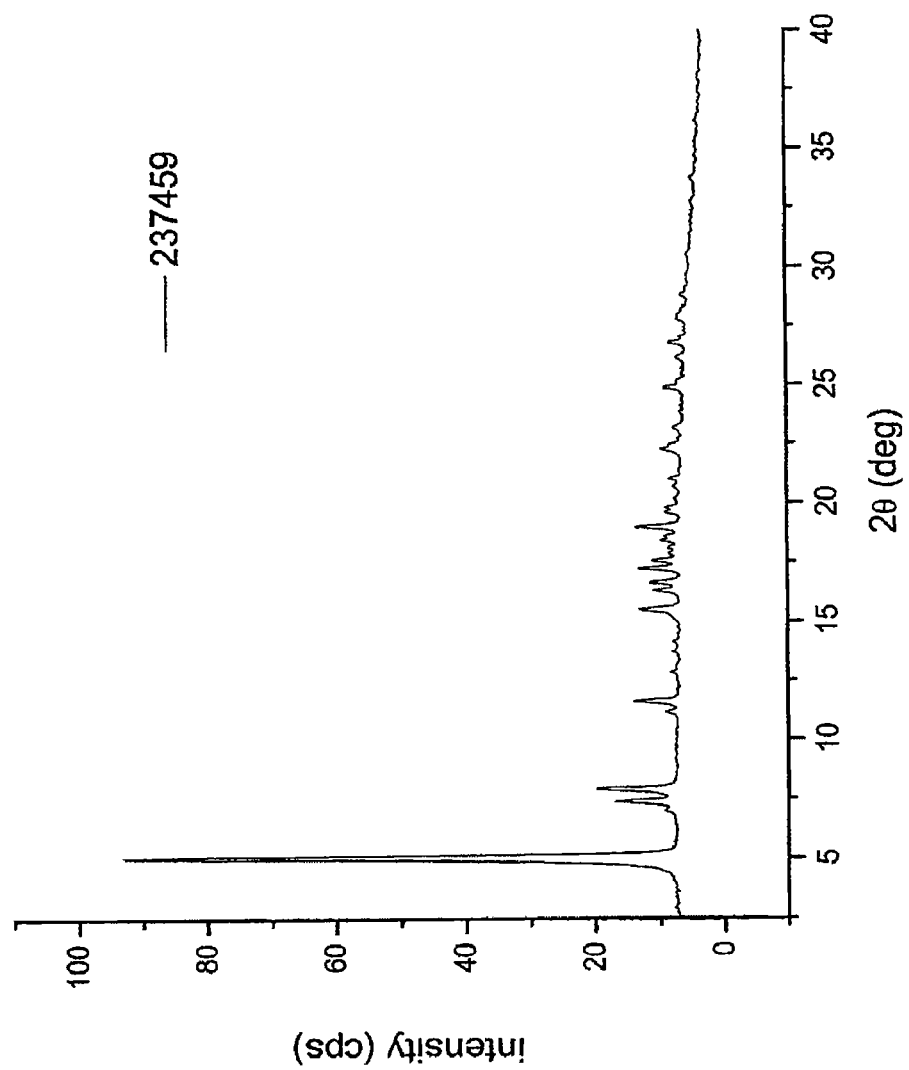
FIG. 1 shows an X-ray powder diffractogram of crystalline calcium (3S)-{[(1R)-isobutanoyloxyethoxy]carbonylaminomethyl}-5-methyl-hexanoate hydrate crystallized from ethanol/water.

"Bioavailability" refers to the amount of a drug that reaches the systemic circulation of a patient following administration of the drug or prodrug thereof to the patient and may be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or prodrug thereof to the patient, and $T_{max}$ is the time to the maximum concentration ($C_{max}$) of a drug in the plasma or blood of a patient following administration of a dose of the drug or prodrug thereof to the patient.

"Calcium (3S)-{[(1R)-isobutanoyloxyethoxy]carbonylaminomethyl}-5-methyl-hexanoate" (3) refers to a salt comprising the anion (3S)-{[(1R)-isobutanoyloxyethoxy]carbonylaminomethyl}-5-methyl-hexanoate and the calcium (2+) cation in a [2:1] molar ratio. Other chemical names for calcium (3S)-{[(1R)-isobutanoyloxyethoxy]carbonylaminomethyl}-5-methyl-hexanoate include 3-({[(1R)-1-(2-methylpropanoyloxy)ethoxy]-carbonylamino}methyl)(3S)-5-methylhexanoic acid calcium salt and (1-(R)-3-({[1-(2-methylpropanoyloxy)-ethoxy]carbonylamino}methyl)(3S)-5-methylhexanoic acid, calcium salt.

"Crystalline" means having a regularly repeating arrangement of molecules.

"Disease" refers to a disease, disorder, condition, symptom, or indication.

"Hydrate" means associated with water.

"Hydrate of crystalline calcium (3S)-{[(1R)-isobutanoyloxyethoxy]carbonylaminomethyl}-5-methyl-hexanoate" or "crystalline calcium (3S)-{[(1R)-isobutanoyloxyethoxy]carbonylaminomethyl}-5-methyl-hexanoate hydrate" (3a) refers to a compound in which anhydrous calcium (3S)-{[(1R)-isobutanoyloxyethoxy]carbonylaminomethyl}-5-methyl-hexanoate is associated with water molecules, including fractional water molecules. For example, crystalline calcium (3S)-{[(1R)-isobutanoyloxyethoxy]carbonylaminomethyl}-5-methyl-hexanoate hydrate may contain less than one molar fraction of water, or from about 1 to about 3 moles of water, including fractional moles of water, per mole of crystalline calcium (3S)-{[(1R)-isobutanoyloxyethoxy]carbonylaminomethyl}-5-methyl-hexanoate hydrate. Crystalline calcium (3S)-{[(1R)-isobutanoyloxyethoxy]carbonylaminomethyl}-5-methyl-hexanoate hydrate, for example, may contain from about 2 wt % water to about 5 wt % water. The one or more molecules of water may be incorporated into the crystal lattice or loosely bound to the crystal lattice. In certain embodiments, one molecule of water per molecule of anhydrous calcium (3S)-{[(1R)-isobutanoyloxyethoxy]carbonylaminomethyl}-5-methyl-hexanoate is incorporated into the crystalline lattice and any additional water content is bound to the exterior of the crystalline lattice. Crystalline calcium (3S)-{[(1R)-isobutanoyloxyethoxy]carbonylaminomethyl}-5-methyl-hexanoate hydrate includes crystalline calcium (3S)-{[(1R)-isobutanoyloxyethoxy]carbonylaminomethyl}-5-methyl-hexanoate monohydrate and crystalline calcium (3S)-{[(1R)-isobutanoyloxyethoxy]carbonylaminomethyl}-5-methyl-hexanoate dihydrate. Other chemical names for crystalline calcium (3S)-{[(1R)-isobutanoyloxyethoxy]carbonylaminomethyl}-5-methyl-hexanoate monohydrate are 3-({[(1R)-1-(2-methylpropanoyloxy)ethoxy]-carbonylamino}methyl)(3S)-5-methylhexanoic acid calcium salt (2:1) monohydrate; 3-({[(1R)-1-(2-methylpropanoyloxy)ethoxy]carbonylamino}methyl)(3S)-5-methylhexanoic acid calcium salt, monohydrate; and (1-(R)-3-({[1-(2-methylpropanoyloxy)-ethoxy]carbonylamino}methyl)(3S)-5-methylhexanoic acid, calcium salt, monohydrate.

"Patient" includes mammals, such as for example, humans.

"Pharmaceutical composition" refers to a composition comprising at least one compound provided by the present disclosure and at least one pharmaceutically acceptable vehicle with which the compound is administered to a patient.

"Pharmaceutically acceptable" refers to approved or approvable by a regulatory agency of a federal or a state government, listed in the U.S. Pharmacopeia, or listed in other generally recognized pharmacopeia for use in mammals, including humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which crystalline calcium (3S)-{[(1R)-isobutanoyloxyethoxy]carbonylaminomethyl}-5-methyl-hexanoate hydrate can be administered to a patient and which does not destroy the pharmacological activity thereof and which is nontoxic when administered in doses sufficient to provide a therapeutically effective amount of the compound.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach, or the agent may be supplied exogenously. For example, the promoiety of (3S)-{[(1R)-isobutanoyloxyethoxy]carbonylaminomethyl}-5-methyl-hexanoate is:

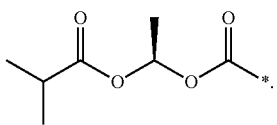

"Sustained release" refers to release of a therapeutic or preventive amount of a drug or an active metabolite thereof over a period of time that is longer than that of an immediate release formulation of the drug. For oral formulations, the term "sustained release" typically means release of the drug within the gastrointestinal tract lumen over a time period ranging, for example, from about 2 to about 30 hours, and in certain embodiments, over a time period ranging from about 4 to about 24 hours. Sustained release formulations achieve therapeutically effective concentrations of the drug in the systemic circulation over a prolonged period of time relative to that achieved by oral administration of an immediate release formulation of the drug.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. A "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance can be readily ascertained by those skilled in the art or capable of determination by routine experimentation.

Crystalline Form of a
(3S)-Aminomethyl-5-methyl-Hexanoic Acid Prodrug

The individual diastereomers of compound (I) form calcium salts that differ in their propensity to be isolated as crystalline solids. Thus, for the diastereomeric salts of (3S)-{[1-isobutanoyloxyethoxy]carbonylaminomethyl}-5-methyl-hexanoic acid (1), i.e., calcium (3S)-{[(1R)-isobutanoyloxyethoxy]carbonylaminomethyl}-5-methyl-hexanoate and calcium (3S)-{[(1S)-isobutanoyloxyethoxy]carbonylaminomethyl}-5-methyl-hexanoate, one isomer, calcium (3S)-{[(1R)-isobutanoyloxyethoxy]carbonylaminomethyl}-5-methyl-hexanoate (1-R):

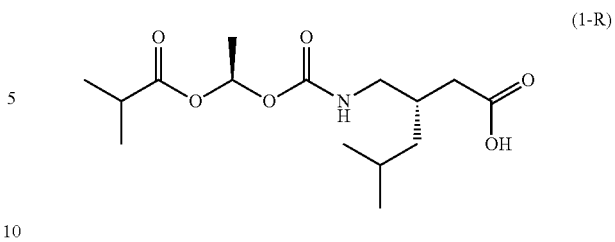

is more readily isolated in morphologically crystalline form. Crystalline calcium (3S)-{[(1R)-isobutanoyloxyethoxy]carbonylaminomethyl}-5-methyl-hexanoate (3) can be isolated in hydrate form (3a) and this material can be crystallized to provide a solid exhibiting a highly ordered crystalline lattice as evidenced by an extensive pattern of both low-angle and high-angle reflections within the X-ray powder diffraction (XRPD) diffractogram.

Reference to calcium (3S)-{[(1R)-isobutanoyloxyethoxy]carbonylaminomethyl}-5-methyl-hexanoate (3) includes all possible tautomeric forms of the conventional chemical structure for this compound and all isotopically labeled derivatives of this compound (e.g., $^2$H, $^3$H, $^{13}$C, $^{14}$C, $^{15}$N, $^{17}$O, $^{18}$O, etc.).

Calcium (3S)-{[(1R)-isobutanoyloxyethoxy]carbonylaminomethyl}-5-methyl-hexanoate (3) can be synthesized following the methods described in Scheme 1.

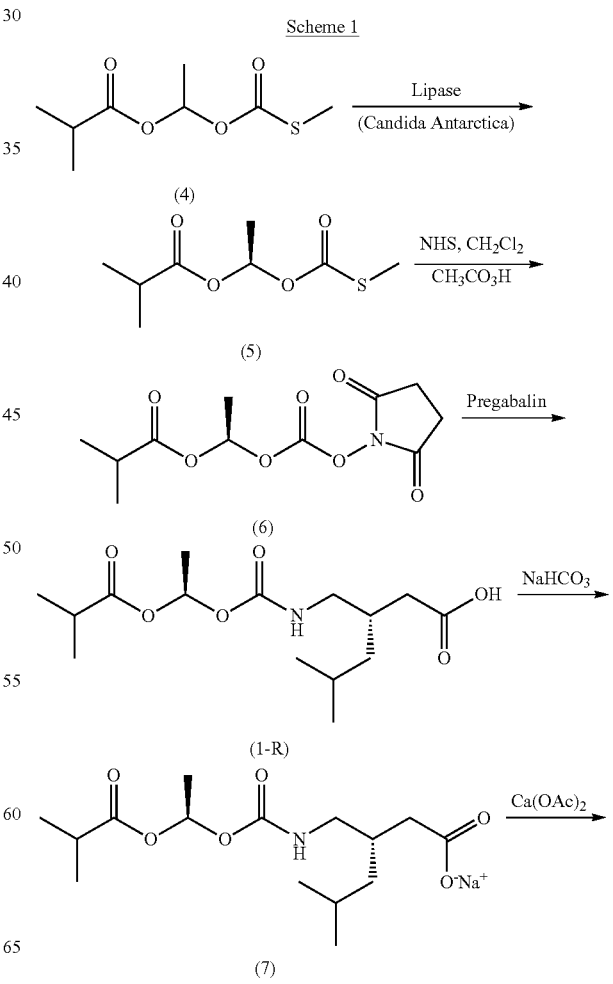

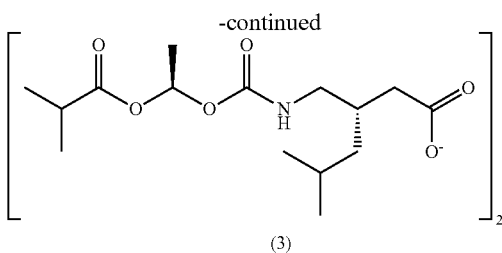

(3)

O-(1-Isobutanoyloxyethyl) S-methyl thiocarbonate (4), prepared as a racemic mixture according to procedures disclosed in Gallop et al., U.S. Pat. No. 7,227,028, can be treated with an appropriate esterase or lipase (e.g., lipase from *Candida antarctica*) in aqueous media (optionally buffered at about pH 7) to selectively degrade the S-enantiomer and provide the desired R-enantiomer (5) with high enantioselectivity and good yield. Conversion of (5) to [((1R)-isobutanoyloxyethoxy)carbonyloxy]succinimide (6) and coupling with pregabalin following the protocols described in Gallop et al., U.S. Pat. No. 7,227,028 provides the free acid form of pregabalin prodrug (1-R). Treatment of (1-R) in an aqueous/organic solvent mixture with 1 molar equivalent of a suitable sodium base (e.g., sodium bicarbonate, sodium carbonate, sodium hydroxide, sodium alkoxide) affords the sodium salt (7) which, optionally, may be isolated as a hygroscopic solid after solvent removal in vacuo. Treatment of an aqueous solution of (7) with a water-soluble calcium salt (e.g., calcium acetate, or calcium chloride) provides compound (3) as a white solid that precipitates from solution and isolated by filtration or centrifugation.

Crystallization of (3) from an aqueous solvent mixture affords calcium (3S)-{[(1R)-isobutanoyloxyethoxy]carbonylaminomethyl}-5-methyl-hexanoate hydrate (3a) as a white crystalline solid. In certain embodiments, the solvent mixture comprises water and a water-miscible alcohol and compound (3) can be isolated as a white, crystalline hydrate salt (3a). In certain embodiments, the water-miscible alcohol is chosen from methanol, ethanol, n-propanol, n-butanol, and isopropanol. In certain embodiments, the water-miscible alcohol is chosen from methanol and isopropanol. In certain embodiments, the aqueous solvent mixture comprises water and ethanol and compound (3) is isolated as a white, crystalline hydrate salt (3a). In certain embodiments, the aqueous solvent mixture comprises water and isopropanol and compound (3) is isolated as a white, crystalline hydrate salt (3a).

In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.0°±0.2°, 7.4°±0.2°, 7.9°±0.2°, 11.6°±0.2°, 15.5°±0.2°, 17.2°±0.2°, and 19.0°±0.2° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.0°±0.2°, 7.4°±0.2°, 7.9°±0.2°, 11.6°±0.2°, 15.5°±0.2°, 16.3°±0.2°, 16.6°±0.2°, 17.2°±0.2°, 19.0°±0.2°, 22.2°±0.2°, and 24.9°±0.2° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.0°±0.2°, 7.0°±0.2°, 7.4°±0.2°, 7.9°±0.2°, 11.1°±0.2°, 11.6°±0.2°, 12.8°±0.2°, 13.7°±0.2°, 14.1°±0.2°, 15.1°±0.2°, 15.5°±0.2°, 16.3°±0.2°, 16.6°±0.2°, 17.1°±0.2°, 17.5°±0.2°, 17.8°±0.2°, 18.1°±0.2°, 18.4°±0.2°, 18.6°±0.2°, 19.0°±0.2°, 19.6°±0.2°, 19.8°±0.2°, 20.7°±0.2°, 21.0°±0.2°, 22.2°±0.2°, 23.1°±0.2°, 24.9°±0.2°, 26.1°±0.2°, 26.8°±0.2°, 27.8°±0.2°, 28.0°±0.2°, 28.8°±0.2°, 29.7°±0.2° and 30.5°±0.2° in an X-ray powder diffractogram measured using Cu—K$_\alpha$ radiation.

In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.0°±0.1°, 7.4°±0.1°, 7.9°±0.1°, 11.6°±0.1°, 15.5°±0.1°, 17.2°±0.1°, and 19.0°±0.1° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.0°±0.1°, 7.4°±0.1°, 7.9°±0.1°, 11.6°±0.1°, 15.5°±0.1°, 16.3°±0.1°, 16.6°±0.1°, 17.2°±0.1°, 19.0°±0.1°, 22.2°±0.1°, and 24.9°±0.1° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.0°±0.1°, 7.0°±0.1°, 7.4°±0.1°, 7.9°±0.1°, 11.1°±0.1°, 11.6°±0.1°, 12.8°±0.1°, 13.7°±0.1°, 14.1°±0.1°, 15.1°±0.1°, 15.5°±0.1°, 16.3°±0.1°, 16.6°±0.1°, 17.1°±0.1°, 17.5°±0.1°, 17.8°±0.1°, 18.1°±0.1°, 18.4°±0.1°, 18.6°±0.1°, 19.0°±0.1°, 19.6°±0.1°, 19.8°±0.1°, 20.7°±0.1°, 21.0°±0.1°, 22.2°±0.1°, 23.1°±0.1°, 24.9°±0.1°, 26.1°±0.1°, 26.8°±0.1°, 27.8°±0.1°, 28.0°±0.1°, 28.8°±0.1°, 29.7°±0.1° and 30.5°±0.1° in an X-ray powder diffractogram measured using Cu—K$_\alpha$ radiation.

In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.2°, 8.0°±0.2°, 11.6°±0.2°, and 19.2°±0.2° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.2°, 8.0°±0.2°, 11.6°±0.2°, 16.3°±0.2°, and 19.2°±0.2° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.2°, 7.3°±0.2°, 8.0°±0.2°, 11.6°±0.2°, 16.3°±0.2°, 17.3°±0.2°, and 19.2°±0.2° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.2°, 7.3°±0.2°, 8.0°±0.2°, 11.6°±0.2°, 15.5°±0.2°, 16.3°±0.2°, 16.7°±0.2°, 17.3°±0.2°, 19.2°±0.2°, 22.4°±0.2°, and 25.0°±0.2° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.2°, 7.3°±0.2°, 8.0°±0.2°, 11.3°±0.2°, 11.6°±0.2°, 12.9°±0.2°, 13.0°±0.2°, 15.5°±0.2°, 16.3°±0.2°, 16.7°±0.2°, 17.3°±0.2°, 17.5°±0.2°, 18.1°±0.2°, 18.6°±0.2°, 19.7°±0.2°, 20.9°±0.2°, 21.3°±0.2°, 22.4°±0.2°, 25.1°±0.2° and 26.0°±0.2° in an X-ray powder diffractogram measured using Cu—K$_\alpha$ radiation.

In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.1°, 8.0°±0.1°, 11.6°±0.1°, and 19.2°±0.1° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.1°, 8.0°±0.1°, 11.6°±0.1°, 16.3°±0.1°, and 19.2°±0.1° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.1°, 7.3°±0.1°, 8.0°±0.1°, 11.6°±0.1°, 16.3°±0.1°, 17.3°±0.1°, and 19.2°±0.1° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.1°, 7.3°±0.1°, 8.0°±0.1°, 11.6°±0.1°, 15.5°±0.1°, 16.3°±0.1°, 16.7°±0.1°, 17.3°±0.1°, 19.2°±0.1°, 22.4°±0.1°, and 25.0°±0.1° in an X-ray powder diffractogram measured using Cu—K$_\alpha$ radiation. In certain embodiments, crystalline calcium (3S)-{[(1R)-isobutanoyloxyethoxy]carbonylaminomethyl}-5-methyl-hexanoate hydrate exhibits characteristic scattering angles (2θ) at least at 5.1°±0.1°, 7.3°±0.1°, 8.0°±0.1°, 11.3°±0.1°, 11.6°±0.1°, 12.9°±0.1°, 13.0°±0.1°, 15.5°±0.1°, 16.3°±0.1°, 16.7°±0.1°, 17.3°±0.1°, 17.5°±0.1°, 18.1°±0.1°, 18.6°±0.1°, 19.7°±0.1°, 20.9°±0.1°, 21.3°±0.1°, 22.4°±0.1°, 25.1°±0.1° and 26.0°±0.1° in an X-ray powder diffractogram measured using Cu—K$_\alpha$ radiation.

In certain embodiments, crystalline calcium (3S)-{[(1R)-isobutanoyloxyethoxy]carbonylaminomethyl}-5-methyl-hexanoate hydrate comprises from about 1 mole water per mole calcium (3S)-{[(1R)-isobutanoyloxyethoxy]carbonylaminomethyl}-5-methyl-hexanoate to about 3 moles water per mole calcium (3S)-{[(1R)-isobutanoyloxyethoxy]carbonylaminomethyl}-5-methyl-hexanoate. In certain embodiments, crystalline calcium (3S)-{[(1R)-isobutanoyloxyethoxy]carbonylaminomethyl}-5-methyl-hexanoate hydrate comprises about 1 mole water per mole calcium (3S)-{[(1R)-isobutanoyloxyethoxy]carbonylaminomethyl}-5-methyl-hexanoate. In certain embodiments, crystalline calcium (3S)-{[(1R)-isobutanoyloxyethoxy]carbonylaminomethyl}-5-methyl-hexanoate hydrate comprises from about 2 wt % water to about 5 wt % water. In certain embodiments, crystalline calcium (3S)-{[(1R)-isobutanoyloxyethoxy]carbonylaminomethyl}-5-methyl-hexanoate hydrate comprises about 2.6 wt % water. In certain embodiments, crystalline calcium (3S)-{[(1R)-isobutanoyloxyethoxy]carbonylaminomethyl}-5-methyl-hexanoate hydrate undergoes a melt/phase transition between about 105° C. and about 120° C. In certain embodiments, crystalline calcium (3S)-{[(1R)-isobutanoyloxyethoxy]carbonylaminomethyl}-5-methyl-hexanoate hydrate undergoes a melt/phase transition between about 107° C. and about 115° C. In certain embodiments, crystalline calcium (3S)-{[(1R)-isobutanoyloxyethoxy]carbonylaminomethyl}-5-methyl-hexanoate hydrate undergoes a melt/phase transition between about 107° C. and about 111° C. In certain embodiments, crystalline calcium (3S)-{[(1R)-isobutanoyloxyethoxy]carbonylaminomethyl}-5-methyl-hexanoate hydrate undergoes a melt/phase transition between about 91° C. to about 129° C.

In certain embodiments, crystalline calcium (3S)-{[(1R)-isobutanoyloxyethoxy]carbonylaminomethyl}-5-methyl-hexanoate may be prepared by first adding calcium (3S)-{[(1R)-isobutanoyloxyethoxy]carbonylaminomethyl}-5-methyl-hexanoate to a solvent mixture to form a solution or suspension. As used herein, the terms solution and suspension are used interchangeably and are meant to include embodiments in which a compound is in a solvent or solvent mixture regardless of solubility. A solvent combination can be such that a compound in solution exhibits temperature-dependent solubility. In general, solvent combinations in which a compound is soluble within a first temperature range, and poorly soluble within a second temperature range, can be used in the crystallization methods disclosed herein. Mixtures of a "good" solvent and an "anti-solvent" can also be used with temperature dependent solubilization, i.e., dissolving at elevated temperature and crystallizing at room temperature. Examples of suitable "good" solvents, i.e., a solvent in which calcium (3S)-{[(1R)-isobutanoyloxyethoxy]carbonylaminomethyl}-5-methyl-hexanoate is soluble, include methanol, ethanol, isopropanol, acetone, methyl isobutyl ketone, tetrahydrofuran, 2-methyl tetrahydrofuran, 1,4-dioxane, 1,2-ethandiol, 1,2-propanediol, 2-methoxyethanol, 2-ethoxyethanol, and a mixture of any of the foregoing. Examples of suitable "anti-solvents", i.e., a solvent in which calcium (3S)-{[(1R)-isobutanoyloxyethoxy]carbonylaminomethyl}-5-methyl-hexanoate exhibits poor solubility, include water, diethyl ether, diisopropyl ether, methyl t-butyl ether, toluene, chlorobenzene, alkanes such as pentane, hexane, heptane, octane, nonane, decane, undecane, dodecane, cis- or trans-decalin, cyclohexane, methylcyclohexane, and a mixture of any of the foregoing.

In certain embodiments, the dissolution process can be carried out at elevated temperature, up to and including the boiling point of the solvent combination. Accordingly, in certain embodiments, calcium (3S)-{[(1R)-isobutanoyloxyethoxy]carbonylaminomethyl}-5-methyl-hexanoate can be dissolved in an aqueous solvent mixture with heating and optionally, with shaking and stirring. The heated solution may be maintained at elevated temperature to ensure complete dissolution of the compound. The heated solution may also be filtered at elevated temperature to remove any undissolved components.

The heated solution can then be slowly cooled to crystallize calcium (3S)-{[(1R)-isobutanoyloxyethoxy]carbonylaminomethyl}-5-methyl-hexanoate hydrate, which may be separated from residual solvent by filtration and/or drying under reduced pressure. In certain embodiments, the solution can be cooled to between about 0° C. and about 25° C. Other methods known to those of skill in the crystallization arts, (e.g., solvent evaporation, drowning, chemical reaction, seeding with a small quantity of the desired crystal form, etc.) may also be employed to crystallize calcium (3S)-{[(1R)-isobutanoyloxyethoxy]carbonylaminomethyl}-5-methyl-hexanoate hydrate.

Calcium (3S)-{[(1R)-isobutanoyloxyethoxy]carbonylaminomethyl}-5-methyl-hexanoate hydrate can be prepared by steps comprising providing a solution comprising calcium (3S)-{[(1R)-isobutanoyloxyethoxy]carbonylaminomethyl}-5-methyl-hexanoate, water, and a water-miscible solvent; and adjusting the temperature of the solution to provide crystalline calcium (3S)-{[(1R)-isobutanoyloxyethoxy]carbonylaminomethyl}-5-methyl-hexanoate hydrate. In certain embodiments, the water miscible solvent is chosen from ethanol and isopropanol. In certain embodiments, the solution comprises water in an amount ranging from about 40 v/v % to about 75 v/v %.

Calcium (3S)-{[(1R)-isobutanoyloxyethoxy]carbonylaminomethyl}-5-methyl-hexanoate hydrate can be prepared by steps comprising providing a first solution comprising calcium (3S)-{[(1R)-isobutanoyloxyethoxy]carbonylaminomethyl}-5-methyl-hexanoate and absolute ethanol; adding de-ionized water to the first solution to provide a mixture; adjusting the temperature of the mixture to provide a second solution; and adjusting the temperature of the second solution to provide crystalline calcium (3S)-{[(1R)-isobutanoyloxyethoxy]carbonylaminomethyl}-5-methyl-hexanoate hydrate. In certain embodiments, crystalline calcium (3S)-{[(1R)-isobutanoyloxyethoxy]carbonylaminomethyl}-5-methyl-hexanoate hydrate prepared using this method exhibits a melting point range from about 107° C. to about 111° C. In certain of the foregoing embodiments, de-ionized water can be added to the first solution to provide a turbid mixture.

Crystalline calcium (3S)-{[(1R)-isobutanoyloxyethoxy]carbonylaminomethyl}-5-methyl-hexanoate hydrate can be prepared by steps comprising providing a first solution of calcium (3S)-{[(1R)-isobutanoyloxyethoxy]carbonylaminomethyl}-5-methyl-hexanoate and isopropanol; adding de-ionized water to the first solution to form a mixture; adjusting the temperature of the mixture to provide a second solution; adjusting the temperature of the second solution to about room temperature to provide a third solution; and adjusting the temperature of the third solution to provide crystalline calcium (3S)-{[(1R)-isobutanoyloxyethoxy]carbonylaminomethyl}-5-methyl-hexanoate hydrate. In certain embodiments, crystalline calcium (3S)-{[(1R)-isobutanoyloxyethoxy]carbonylaminomethyl}-5-methyl-hexanoate hydrate prepared using this method exhibits a melting point range from about 112° C. to about 117° C. In certain of the foregoing embodiments, de-ionized water can be added to the first solution to provide a turbid mixture.

Therapeutic Uses

The pharmacological activity of (3S)-aminomethyl-5-hexanoic acid is believed to be effected through binding to the α2δ subunit of voltage-gated calcium channels and the concomitant reduction in the synaptic release of neurotransmitters such as noradrenaline, glutamate, and substance P (see, e.g., Taylor et al., *Epilepsy Res* 2007, 73, 137-50). Accordingly, administering crystalline calcium (3S)-{[(1R)-isobutanoyloxyethoxy]carbonylaminomethyl}-5-methyl-hexanoate hydrate to a patient can be expected to be useful in treating diseases and disorders associated with α2δ subunit of voltage-gated calcium channels. In clinical trials, (3S)-aminomethyl-5-hexanoic acid has been shown to be effective in treating diseases and disorders including, for example, postoperative pain (Dahl et al., *Acta Anaesthesiol Scand* 2004, 48, 1130-1136); neuropathic pain (Zareba, *Drugs Today* 2005, 41(8), 509-16; and Blommel and Blommel, *Am J Health Syst Pharm* 2007, 64(14), 1475-82); chemotherapy-induced pain (Rao et al., *Cancer* 2007, 110(9), 2110-8; and Saif and Hashmi, *Cancer Chemother Pharmacol* 2008, 61, 349-354); general anxiety disorder (Rickels et al., *Arch Gen Psychiatry* 2005, 62, 1022-1030); anxiety (Pohl et al., *J Clin Psychopharmacol* 2005, 25, 151-8); poster-herpetic neuralgia and painful diabetic peripheral neuropathy (Freynhagen et al., *Pain* 2005, 115, 254-63); sleep disorders (Sabatowski et al., *Pain* 2004, 109, 26-35; and Hindmarch et al., *Sleep* 2005, 28(2), 187-93); ethanol withdrawal syndrome (Becker et al., *Alcohol & Alcoholism* 2006, 41(4), 399-406); fibromyalgia (Crofford et al., *Arthritis and Rheumatism* 2005, 52, 1264-73); restless legs syndrome (Sommer et al., *Acta Neruol Scand* 2007, 115(5), 347-50); pain associated with spinal cord injury (Siddall et al., *Neurology* 2006, 67(10), 1792-800); social phobia (Pande et al., *J Clin Psychopharmacol* 2004, 24(2), 141-149); and others. A number of studies have shown that gabapentin, another GABA analog with affinity for the α2δ subunit, is useful for preventing migraine (see, e.g., Mathew et al., *Headache* 2001, 41, 119-128; Mathew, *Cephalalgia* 1996, 16, 367; and Wessely et al., *Cephalalgia* 1987, 7 (Suppl 6), 477-478).

Crystalline calcium (3S)-{[(1R)-isobutanoyloxyethoxy]carbonylaminomethyl}-5-methyl-hexanoate hydrate or a pharmaceutical composition thereof may be administered to a patient, such as a human, suffering from treating a disease chosen from a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation. Further, in certain embodiments, crystalline calcium (3S)-{[(1R)-isobutanoyloxyethoxy]carbonylaminomethyl}-5-methyl-hexanoate hydrate or pharmaceutical composition thereof can be administered to a patient, such as a human, as a preventative measure against various diseases or disorders. Crystalline calcium (3S)-{[(1R)-isobutanoyloxyethoxy]carbonylaminomethyl}-5-methyl-hexanoate hydrate or a pharmaceutical composition thereof may be administered as a preventative measure to a patient having a predisposition for a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation. Accordingly, crystalline calcium (3S)-{[(1R)-isobutanoyloxyethoxy]carbonylaminomethyl}-5-methyl-hexanoate hydrate or a pharmaceutical composition thereof may be used for the prevention of one disease or disorder and concurrently for the treatment of another (e.g., prevention of psychosis while treating a gastrointestinal disorder; prevention of neuropathic pain while treating ethanol withdrawal syndrome).

The efficacy of administering calcium (3S)-{[(1R)-isobutanoyloxyethoxy]carbonylaminomethyl}-5-methyl-hexanoate hydrate for treating a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation may be assessed using animal and human models of fibromyalgia and on clinical results using methods known in the art.

Crystalline calcium (3S)-{[(1R)-isobutanoyloxyethoxy]carbonylaminomethyl}-5-methyl-hexanoate hydrate or a pharmaceutical composition thereof may be used to treat movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation using known procedures described in the art.

Calcium (3S)-{[(1R)-isobutanoyloxyethoxy]carbonylaminomethyl}-5-methyl-hexanoate hydrate may be more efficacious than the parent drug molecule (i.e. pregabalin) in treating a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation because when administered orally the compound provides for sustained therapeutically effective blood concentrations of (3S)-aminomethyl-5-hexanoic acid. It is believed that metabolites of crystalline calcium (3S)-{[(1R)-isobutanoyloxyethoxy]carbonylaminomethyl}-5-methyl-hexanoate hydrate such as the (3S)-{[(1R)-isobutanoyloxyethoxy]carbonylaminomethyl}-5-methyl-hexanoate anion or protonated form thereof are absorbed from the gastrointestinal lumen into the blood by a different mechanism than that by which pregabalin and other known GABA analogs are absorbed. For example, pregabalin is believed to be actively transported across the gut wall by a carrier transporter localized in the human small intestine. In comparison to pregabalin, the compounds disclosed herein, are believed to be absorbed across the gut wall along a greater portion of the gastrointestinal tract, including the colon.

Because metabolites of crystalline calcium (3S)-{[(1R)-isobutanoyloxyethoxy]carbonylaminomethyl}-5-methyl-hexanoate hydrate, such as the (3S)-{[(1R)-isobutanoyloxyethoxy]carbonylaminomethyl}-5-methyl-hexanoate anion or protonated form thereof can be absorbed throughout the gastrointestinal tract, including the colon, the compound can be advantageously formulated in sustained release oral formulations that provide for sustained release of the compound over a period of hours into the gastrointestinal tract and in particular, release within the colon, crystalline calcium (3S)-{[(1R)-isobutanoyloxyethoxy]carbonylaminomethyl}-5-methyl-hexanoate hydrate may also be more efficacious than pregabalin in treating a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation. The ability of crystalline calcium (3S)-{[(1R)-isobutanoyloxyethoxy]carbonylaminomethyl}-5-methyl-hexanoate hydrate to be used in sustained release oral dosage forms can facilitate therapeutic regimens having a reduced dosing frequency necessary to maintain a therapeutically effective pregabalin concentration in the blood.

In certain embodiments, crystalline calcium (3S)-{[(1R)-isobutanoyloxyethoxy]carbonylaminomethyl}-5-methyl-hexanoate hydrate or a pharmaceutical composition thereof can be administered to a patient for treating a movement disorder such as epilepsy, hypokinesia, spasticity, and restless legs syndrome. In certain embodiments, crystalline calcium (3S)-{[(1R)-isobutanoyloxyethoxy]carbonylaminomethyl}-5-methyl-hexanoate hydrate can be administered to a patient to treat restless legs syndrome, and for example, patients with severe symptoms such as daytime symptoms.

In certain embodiments, crystalline calcium (3S)-{[(1R)-isobutanoyloxyethoxy]carbonylaminomethyl}-5-methyl-hexanoate hydrate can be administered to a patient for treating a gastrointestinal disorder such as irritable bowel syndrome.

In certain embodiments, crystalline calcium (3S)-{[(1R)-isobutanoyloxyethoxy]carbonylaminomethyl}-5-methyl-hexanoate hydrate can be administered to a patient for treating a psychotic disorder such as schizophrenia.

In certain embodiments, crystalline calcium (3S)-{[(1R)-isobutanoyloxyethoxy]carbonylaminomethyl}-5-methyl-hexanoate hydrate can be administered to a patient for treating a mood disorder such as depressive disorder, dysthymic disorder, bipolar I disorder, bipolar II disorder, cyclothymic disorder, and mood disorder. In certain embodiments, crystalline calcium (3S)-{[(1R)-isobutanoyloxyethoxy]carbonylaminomethyl}-5-methyl-hexanoate hydrate or pharmaceutical composition thereof can be administered to a patient for treating bipolar I disorder and bipolar II disorder.

In certain embodiments, crystalline calcium (3S)-{[(1R)-isobutanoyloxyethoxy]carbonylaminomethyl}-5-methyl-hexanoate hydrate can be administered to a patient for treating an anxiety disorder such as generalized anxiety disorder, anxiety induced by drugs or medical problems, panic attacks, panic disorder, phobic disorders such as agoraphobia social phobia, and specific phobia, obsessive-compulsive disorder, posttraumatic stress disorder, and acute stress disorder.

In certain embodiments, crystalline calcium (3S)-{[(1R)-isobutanoyloxyethoxy]carbonylaminomethyl}-5-methyl-hexanoate hydrate can be administered to a patient for treating a sleep disorder such as primary insomnia, primary hypersomnia, narcolepsy, breathing-related sleep disorder, circadian rhythm sleep disorder, a parasomnia, a sleep disorder due to a general medical condition, and substance-induced sleep disorder.

In certain embodiments, crystalline calcium (3S)-{[(1R)-isobutanoyloxyethoxy]carbonylaminomethyl}-5-methyl-hexanoate hydrate can be administered to a patient for treating a pulmonary disorder such as asthma, cough, and chronic obstructive pulmonary disease.

In certain embodiments, crystalline calcium (3S)-{[(1R)-isobutanoyloxyethoxy]carbonylaminomethyl}-5-methyl-hexanoate hydrate can be administered to a patient for treating a neurodegenerative disorder such as Alzheimer's disease, Huntington's disease, Parkinson's disease, and amyotrophic lateral sclerosis.

In certain embodiments, crystalline calcium (3S)-{[(1R)-isobutanoyloxyethoxy]carbonylaminomethyl}-5-methyl-hexanoate hydrate can be administered to a patient for treating an inflammatory disease such as a chronic inflammatory airway disorder including asthma, exercise-induced bronchospasm (EIB), and chronic obstructive pulmonary disease; a chronic inflammatory bowel disease including ulcerative colitis, and Crohn's disease; a chronic inflammatory connective tissue disease including lupus erythematosus, scleroderma, Sjogren's syndrome, poly- and dermatomyositis, vasculitis, and MCTD; a chronic inflammatory joint disease including rheumatoid arthritis, juvenile chronic arthritis (Still's disease), rheumatoid spondylitis, lupus erythematosus, ankylosing spondylitis, psoriatic arthritis, and reactive arthritis; a chronic inflammatory skin disease including psoriasis, diskoid lupus erythematosus, scleroderma, hives, rosacea, dermatitis, and atopic dermatitis; and other diseases associated with inflammation including spondyloarthropies, cardiomyopathy, atherosclerosis vasculitis, acute renal disease, chronic renal disease, glomerulonephritis, inflammatory eye disorders, tuberculosis, chronic cholecystitis, bronchiectasis, Hashimoto's thyroidiitis, silicosis and other pneumoconioses, and hyper-IgG4 disease.

In certain embodiments, crystalline calcium (3S)-{[(1R)-isobutanoyloxyethoxy]carbonylaminomethyl}-5-methyl-hexanoate hydrate can be administered to a patient for treating pain. Pain includes nociceptive pain caused by injury to bodily tissues and neuropathic pain caused by abnormalities in nerves, spinal cord, and/or brain. Pain includes mechanical allodynia, thermal allodynia, hyperplasia, central pain, peripheral neuropathic pain, diabetic neuropathy, breakthrough pain, cancer pain, deafferentation pain, dysesthesia, fibromyalgia syndrome, hyperpathia, incident pain, movement-related pain, myofacial pain, and paresthesia.

In certain embodiments, crystalline calcium (3S)-{[(1R)-isobutanoyloxyethoxy]carbonylaminomethyl}-5-methyl-hexanoate hydrate can be administered to a patient for treating neuropathic pain. There are several types of neuropathic pain. A classification that relates to the type of damage or related pathophysiology causing a painful neuropathy includes neuropathies associated with mechanical nerve injury such as carpal tunnel syndrome, vertebral disk herniation, entrapment neuropathies, ulnar neuropathy, and neurogenetic thoracic outlet syndrome; metabolic disease associated neuropathies such as diabetic polyneuropathy; neuropathies associated with neurotropic viral disease such as herpes zoster and human immunodeficiency virus (HIV) disease; neuropathies associated with neurotoxicity such as chemotherapy of cancer or tuberculosis, radiation therapy, drug-induced neuropathy, and alcoholic neuropathy; neuropathies associated with inflammatory and/or immunologic mechanisms such as multiple sclerosis, anti-sulfatide antibody neuropathies, neuropathy associated with monoclonal gammopathy, Sjogren's disease, lupus, vasculitic neuropathy, polyclonal inflammatory neuropathies, Guillain-Barre syndrome, chronic inflammatory demyelinating neuropathy, multifocal motor neuropathy, paraneoplastic autonomic neuropathy, ganglinoic acetylcholine receptor antibody autonomic neuropathy, Lambert-Eaton myasthenic syndrome and myasthenia gravis; neuropathies associated with nervous system focal ischemia such as thalamic syndrome (anesthesia dolorosa); neuropathies associated with multiple neurotransmitter system dysfunction such as complex regional pain syndrome (CRPS); neuropathies associated with chronic/neuropathic pain such as osteoarthritis, low back pain, fibromyalgia, cancer bone pain, chronic stump pain, phantom limb pain, and paraneoplastic neuropathies; toxic neuropathies (e.g., exposure to chemicals such as exposure to acrylamide, 3-chlorophene, carbamates, carbon disulfide, ethylene oxide, n-hexane, methyl n-butylketone, methyl bromide, organophosphates, polychlorinated biphenyls, pyriminil, trichlorethylene, or dichloroacetylene), focal traumatic neuropathies, phantom and stump pain, monoradiculopathy, and trigeminal neuralgia; and central neuropathies including ischemic cerebrovascular injury (stroke), multiple sclerosis, spinal cord injury, Parkinson's disease, amyotrophic lateral sclerosis, syringomyelia, neoplasms, arachnoiditis, and post-operative/post-surgical pain (perioperative pain); mixed neuropathies such as diabetic neuropathies (including symmetric polyneuropathies such as sensory or sensorimotor polyneuropathy, selective small-fiber polyneuropathy, and autonomic neuropathy; focal and multifocal neuropathies such as cranial neuropathy, limb mononeuropathy, trunk mononeuropathy, mononeuropathy multiplex, and asymmetric lower limb motor neuropathy) and sympathetically maintained pain. Other neuropathies include focal neuropathy; glosopharyngeal neuralgia; ischemic pain; trigeminal neuralgia; atypical facial pain associated with Fabry's disease, Celiac disease, hereditary sensory neuropathy, or $B_{12}$-deficiency; mono-neuropathies; polyneuropathies; hereditary peripheral neuropathies such as Carcot-Marie-Tooth disease, Refsum's disease, Strumpell-Lorrain disease, and retinitis pigmentosa; acute polyradiculoneuropathy; and chronic polyradiculoneuropathy. Paraneoplastic neuropathies include paraneoplastic subacute sensory neuropathy, paraneoplastic motor neuron disease, paraneoplastic neuromyotonia, paraneoplastic demyelinating neuropathies, paraneoplastic vasculitic neuropathy, and paraneoplastic autonomic insufficiency. Crystalline calcium (3S)-{[(1R)-isobutanoyloxyethoxy]carbonylaminomethyl}-5-methyl-hexanoate hydrate can be used to treat any of the foregoing types of neuropathic pain. In certain embodiments, the neuropathic pain is chosen from post-operative/post-surgical pain (perioperative pain), post-herpetic neuralgia, peripheral neuropathy, HIV-related neuropathic pain, cancer-related pain, and chemotherapy-induced pain.

In certain embodiments, crystalline calcium (3S)-{[(1R)-isobutanoyloxyethoxy]carbonylaminomethyl}-5-methyl-hexanoate hydrate or a pharmaceutical composition thereof can be administered to a patient to treat chemotherapy-induced arthralgias, myalgias, and/or neuropathic pain. In certain embodiments, crystalline calcium (3S)-{[(1R)-isobutanoyloxyethoxy]carbonylaminomethyl}-5-methyl-hexanoate hydrate or a pharmaceutical composition thereof can be administered to a patient to treat HIV-induced neuropathy. In certain embodiments, crystalline calcium (3S)-{[(1R)-isobutanoyloxyethoxy]carbonylaminomethyl}-5-methyl-hexanoate hydrate can be administered to a patient to treat post-herpetic neuropathy. In certain embodiments, crystalline calcium (3S)-{[(1R)-isobutanoyloxyethoxy]carbonylaminomethyl}-5-methyl-hexanoate hydrate or a pharmaceutical composition thereof can be administered to a patient to treat painful diabetic neuropathy. In certain embodiments, crystalline calcium (3S)-{[(1R)-isobutanoyloxyethoxy]carbonylaminomethyl}-5-methyl-hexanoate hydrate or a pharmaceutical composition thereof can be administered to a patient to treat fibromyalgia.

In certain embodiments, crystalline calcium (3S)-{[(1R)-isobutanoyloxyethoxy]carbonylaminomethyl}-5-methyl-hexanoate hydrate can be administered to a patient for treating musculoskeletal pain. Musculoskeletal conditions causing tenderness and muscle spasms include fibromyalgia, tension headaches, myofascial pain syndrome, facet joint pain, internal disk disruption, somatic dysfunction, spinal fractures, vertebral osteomyelitis, polymyalgia rheumatica, atlantoaxial instability, atlanto-occipital joint pain, osteoporotic vertebral compression fracture, Scheuermann's disease, spondylosis, spondylolisthesis, kissing spines, sacroiliac joint pain, sacral stress fracture, coccygodynia, failed back syndrome, and mechanical low back or neck pain. In these conditions, muscle spasm is related to local factors involving the affected muscle groups without the increased tone or reflex characteristic of spasticity. Muscle, tendon, ligament, intervertebral disc, articular cartilage, and bone can be involved in musculoskeletal pain. Disorders that can produce neck and back pain include muscle strain, ligament sprain, myofascial pain, fibromyalgia, facet joint pain, internal disc disruption, somatic dysfunction, spinal fracture, verterbral osteomyelitis, and polymyalgia rheumatica, atlanto-axial instability and atlanto-occipital joint pain. Crystalline calcium (3S)-{[(1R)-isobutanoyloxyethoxy]carbonylaminomethyl}-5-methyl-hexanoate hydrate can be used to treat any of the foregoing types of musculoskeletal pain. In certain embodiments, musculoskeletal pain is fibromyalgia.

In certain embodiments, crystalline calcium (3S)-{[(1R)-isobutanoyloxyethoxy]carbonylaminomethyl}-5-methyl-hexanoate hydrate can be administered to a patient for treating migraine, including the prevention of migraine in patients in patients having a predisposition for or history of migraine.

In certain embodiments, crystalline calcium (3S)-{[(1R)-isobutanoyloxyethoxy]carbonylaminomethyl}-5-methyl-hexanoate hydrate can be administered to a patient for treating a disease chosen from hot flashes, faintness attacks, urinary incontinence, ethanol withdrawal syndrome, and premature ejaculation.

In certain embodiments, methods of treatment comprise administering to a patient crystalline calcium (3S)-{[(1R)-isobutanoyloxyethoxy]carbonylaminomethyl}-5-methyl-hexanoate hydrate in an oral dosage formulation. In certain embodiments, methods of treatment comprise administering to a patient crystalline calcium (3S)-{[(1R)-isobutanoyloxyethoxy]carbonylaminomethyl}-5-methyl-hexanoate hydrate in a sustained release oral dosage formulation. In certain embodiments, methods of treatment comprise administering to a patient crystalline calcium (3S)-{[(1R)-isobutanoyloxyethoxy]carbonylaminomethyl}-5-methyl-hexanoate hydrate in an oral dosage formulation in which crystalline calcium (3S)-{[(1R)-isobutanoyloxyethoxy]carbonylaminomethyl}-5-methyl-hexanoate hydrate is released throughout the gastrointestinal tract, including the colon, to provide a sustained concentration of (3S)-aminomethyl-5-hexanoic acid in the systemic circulation of the patient. In such embodiments, the sustained concentration of (3S)-aminomethyl-5-hexanoic acid can be maintained for at least 6 hours, at least 12 hours, at least 18 hours, or at least 24 hours following administration of a dose of crystalline calcium (3S)-{[(1R)-isobutanoyloxyethoxy]carbonylaminomethyl}-5-methyl-hexanoate hydrate to the patient.

Modes of Administration

Crystalline calcium (3S)-{[(1R)-isobutanoyloxyethoxy]carbonylaminomethyl}-5-methyl-hexanoate hydrate or a pharmaceutical composition thereof may be advantageously used in human medicine. As disclosed herein, crystalline calcium (3S)-{[(1R)-isobutanoyloxyethoxy]carbonylaminomethyl}-5-methyl-hexanoate hydrate or a pharmaceutical composition thereof are useful for the treatment of a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation.

When used to treat the above diseases, crystalline calcium (3S)-{[(1R)-isobutanoyloxyethoxy]carbonylaminomethyl}-5-methyl-hexanoate hydrate or a pharmaceutical composition thereof may be administered or applied singly, or in combination with other agents. Crystalline calcium (3S)-{[(1R)-isobutanoyloxyethoxy]carbonylaminomethyl}-5-methyl-hexanoate hydrate, or a pharmaceutical composition thereof may also be administered or applied singly or in combination with other pharmaceutically active agents, including other GABA analogs.

Methods of treatment include administering to a patient in need of such treatment a therapeutically effective amount of crystalline calcium (3S)-{[(1R)-isobutanoyloxyethoxy]carbonylaminomethyl}-5-methyl-hexanoate hydrate or a pharmaceutical composition thereof. The patient may be an animal, such as a mammal, for example, a human.

Crystalline calcium (3S)-{[(1R)-isobutanoyloxyethoxy]carbonylaminomethyl}-5-methyl-hexanoate hydrate or a pharmaceutical composition thereof can be administered orally. Crystalline calcium (3S)-{[(1R)-isobutanoyloxyethoxy]carbonylaminomethyl}-5-methyl-hexanoate hydrate or a pharmaceutical composition thereof may be administered by any other convenient route, for example, by infusion or bolus injection, or by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer crystalline calcium (3S)-{[(1R)-isobutanoyloxyethoxy]carbonylaminomethyl}-5-methyl-hexanoate hydrate or a pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes or skin.

In certain embodiments, crystalline calcium (3S)-{[(1R)-isobutanoyloxyethoxy]carbonylaminomethyl}-5-methyl-hexanoate hydrate or a pharmaceutical composition thereof may be delivered via sustained release systems, such as an oral sustained release system.

Crystalline calcium (3S)-{[(1R)-isobutanoyloxyethoxy]carbonylaminomethyl}-5-methyl-hexanoate hydrate or a pharmaceutical composition thereof provides pregabalin upon in vivo administration to a patient. Crystalline calcium (3S)-{[(1R)-isobutanoyloxyethoxy]carbonylaminomethyl}-5-methyl-hexanoate hydrate or a metabolite thereof including calcium (3S)-{[(1R)-isobutanoyloxyethoxy]carbonylaminomethyl}-5-methyl-hexanoate, (3S)-{[(1R)-isobutanoyloxyethoxy]carbonylaminomethyl}-5-methyl-hexanoate, and/or (3S)-aminomethyl-5-methyl-hexanoic acid may be absorbed into the systemic circulation from the gastrointestinal tract either by passive diffusion, active transport or by both passive and active processes.

The promoiety of (3S)-{[(1R)-isobutanoyloxyethoxy]carbonylaminomethyl}-5-methyl-hexanoate may be cleaved either chemically and/or enzymatically. One or more enzymes present in the stomach, intestinal lumen, intestinal tissue, blood, liver, brain or any other tissue of a mammal may cleave the promoiety of (3S)-{[(1R)-isobutanoyloxyethoxy]carbonylaminomethyl}-5-methyl-hexanoate. The promoiety of (3S)-{[(1R)-isobutanoyloxyethoxy]carbonylaminomethyl}-5-methyl-hexanoate may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). When the promoiety of (3S)-{[(1R)-isobutanoyloxyethoxy]carbonylaminomethyl}-5-methyl-hexanoate is cleaved prior to absorption by the gastrointestinal tract, pregabalin may be absorbed into the systemic circulation conventionally (e.g., mediated, in part, via the large neutral amino acid transporter located in the small intestine). When the promoiety of (3S)-{[(1R)-isobutanoyloxyethoxy]carbonylaminomethyl}-5-methyl-hexanoate is cleaved after absorption by the gastrointestinal tract, this pregabalin prodrug may be absorbed into the systemic circulation either by passive diffusion, active transport, or by both passive and active processes.

When the promoiety of (3S)-{[(1R)-isobutanoyloxyethoxy]carbonylaminomethyl}-5-methyl-hexanoate is cleaved after absorption by the gastrointestinal tract, this pregabalin prodrug may be absorbed into the systemic circulation from the large intestine. When the pregabalin prodrug is absorbed by the large intestine, crystalline (3S)-{[(1R)-isobutanoyloxyethoxy]carbonylaminomethyl}-5-methyl-hexanoate hydrate or a pharmaceutical composition thereof can be advantageously administered as a sustained release system. In certain embodiments, crystalline calcium (3S)-{[(1R)-isobutanoyloxyethoxy]carbonylaminomethyl}-5-methyl-hexanoate hydrate or pharmaceutical composition thereof can be delivered by oral sustained release administration. When administered using a sustained release formulation, crystalline calcium (3S)-{[(1R)-isobutanoyloxyethoxy]carbonylaminomethyl}-5-methyl-hexanoate hydrate or a pharmaceutical composition thereof can be administered twice per day or once per day.

In certain embodiments, oral administration of an oral sustained release dosage form comprising crystalline calcium (3S)-{[(1R)-isobutanoyloxyethoxy]carbonylaminomethyl}-5-methyl-hexanoate hydrate can provide a therapeutically effective concentration of (3S)-aminomethyl-5-hexanoic acid in the blood plasma of a patient for a time period of at least about 4 hours after administration of the dosage form, in certain embodiments, for a time period of at least about 8 hours, and in certain embodiments, for a time period of at least about 12 hours, and in certain embodiments, for a time period of at least about 24 hours.

Pharmaceutical Compositions

Pharmaceutical compositions provided by the present disclosure contain crystalline calcium (3S)-{[(1R)-isobutanoyloxyethoxy]carbonylaminomethyl}-5-methyl-hexanoate hydrate together with a suitable amount of a pharmaceutically acceptable vehicle so as to provide a form for proper oral administration to a patient. In certain embodiments, pharmaceutical compositions provided by the present disclosure contain a therapeutically effective amount of crystalline calcium (3S)-{[(1R)-isobutanoyloxyethoxy]carbonylaminomethyl}-5-methyl-hexanoate hydrate together with a suitable amount of a pharmaceutically acceptable vehicle so as to provide a form for proper oral administration to a patient. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. Pharmaceutical compositions provided by the present disclosure may also contain minor amounts of wetting or emulsifying agents or pH buffering agents. In addition, auxiliary, stabilizing, thickening, lubricating and coloring agents may be used.

Pharmaceutical compositions comprising crystalline calcium (3S)-{[(1R)-isobutanoyloxyethoxy]carbonylaminomethyl}-5-methyl-hexanoate hydrate may be manufactured by means of mixing, dissolving, granulating, dragee-making, levigating, emulsifying, encapsulating, entrapping, lyophilizing, or other process known to those skilled in the art of pharmaceutical formulation. Pharmaceutical compositions may be formulated using one or more pharmaceutically acceptable vehicles that facilitate processing crystalline calcium (3S)-{[(1R)-isobutanoyloxyethoxy]carbonylaminomethyl}-5-methyl-hexanoate hydrate into oral dosage formulations, such as a sustained release oral dosage formulation.

Pharmaceutical compositions provided by the present disclosure can take the form of solutions, aqueous or oily suspensions, emulsion, tablets, pills, pellets, capsules, capsules containing liquids, granules, powders, sustained-release formulations, suppositories, emulsions, syrups, elixirs or any other form suitable for oral administration. Orally administered pharmaceutical compositions may contain one or more optional agents, for example, sweetening agents such as fructose, aspartame or saccharin, flavoring agents such as peppermint, oil of wintergreen or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administering the compounds and compositions disclosed herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions can include pharmaceutically acceptable vehicles such as mannitol, lactose, starch, magnesium stearate, sodium saccharine, cellulose, magnesium carbonate, and the like.

For oral liquid preparations such as, for example, suspensions, elixirs and solutions, suitable vehicles include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Crystalline calcium (3S)-{[(1R)-isobutanoyloxyethoxy]carbonylaminomethyl}-5-methyl-hexanoate hydrate may be formulated in rectal or vaginal compositions such as suppositories or retention enemas, e.g., containing conventional suppository bases such as cocoa butter or other glycerides.

In certain embodiments, crystalline calcium (3S)-{[(1R)-isobutanoyloxyethoxy]carbonylaminomethyl}-5-methyl-hexanoate hydrate can be formulated as a single active agent. In certain embodiments, crystalline calcium (3S)-{[(1R)-isobutanoyloxyethoxy]carbonylaminomethyl}-5-methyl-hexanoate hydrate can be formulated as a mixture with one or more other pregabalin prodrugs or salts thereof such as (3S)-{[(1R)-isobutanoyloxyethoxy]carbonylaminomethyl}-5-methyl-hexanoate, (3S)-{[(1S)-isobutanoyloxyisobutoxy]carbonylaminomethyl}-5-methyl-hexanoate, (3S)-{[(1R)-benzoyloxyethoxy]carbonylaminomethyl}-5-methyl-hexanoate, calcium (3S)-{[(1R)-isobutanoyloxyethoxy]carbonylaminomethyl}-5-methyl-hexanoate, calcium (3S)-{[(1S)-isobutanoyloxyisobutoxy]carbonylaminomethyl}-5-methyl-hexanoate, and/or calcium (3S)-{[(1R)-benzoyloxyethoxy]carbonylaminomethyl}-5-methyl-hexanoate.

Dissolution Profiles of Dosage Forms

Dosage forms provided by the present disclosure comprising crystalline calcium (3S)-{[(1R)-isobutanoyloxyethoxy]carbonylaminomethyl}-5-methyl-hexanoate hydrate may be characterized, in part, by the in vitro dissolution profile. Methods for determining dissolution profiles of dosage forms are well known to those skilled in the pharmaceutical arts. Standard methodologies set forth in the U.S. Pharmacopeia may be used. For example, a dissolution profile may be measured in either U.S. Pharmacopeia Type I Apparatus (baskets) or a U.S. Pharmacopeia Type II Apparatus (paddles). Procedures for determining the dissolution profile for dosage forms provided by the present disclosure are described in Example 15.

In certain embodiments, release of crystalline calcium (3S)-{[(1R)-isobutanoyloxyethoxy]carbonylaminomethyl}-5-methyl-hexanoate hydrate from dosage forms provided by the present disclosure exhibits an in vitro dissolution profile in 50 mM sodium phosphate monobasic buffer at pH 6.8 and 37° C. stirred at 100 rpm (USP, Type II) in which about 27% of crystalline calcium (3S)-{[(1R)-isobutanoyloxyethoxy]carbonylaminomethyl}-5-methyl-hexanoate hydrate is released within about 3 hours; about 49% of crystalline calcium (3S)-{[(1R)-isobutanoyloxyethoxy]carbonylaminomethyl}-5-methyl-hexanoate hydrate is released within about 6 hours; about 75% of crystalline calcium (3S)-{[(1R)-isobutanoyloxyethoxy]carbonylaminomethyl}-5-methyl-hexanoate hydrate is released within about 12 hours; and about 100% of crystalline calcium (3S)-{[(1R)-isobutanoyloxyethoxy]carbonylaminomethyl}-5-methyl-hexanoate hydrate is released within about 18 hours.

In certain embodiments, release of crystalline calcium (3S)-{[(1R)-isobutanoyloxyethoxy]carbonylaminomethyl}-5-methyl-hexanoate hydrate from dosage forms provided by the present disclosure exhibits an in vitro dissolution profile in 50 mM sodium phosphate monobasic buffer at pH 6.8 and 37° C. stirred at 100 rpm (USP, Type II) in which about 46% of crystalline calcium (3S)-{[(1R)-isobutanoyloxyethoxy]carbonylaminomethyl}-5-methyl-hexanoate hydrate is released within about 3 hours; about 72% of crystalline calcium (3S)-{[(1R)-isobutanoyloxyethoxy]carbonylaminomethyl}-5-methyl-hexanoate hydrate is released within about 6 hours; and about 100% of crystalline calcium (3S)-{[(1R)-isobutanoyloxyethoxy]carbonylaminomethyl}-5-methyl-hexanoate hydrate is released within about 12 hours.

In certain embodiments, release of crystalline calcium (3S)-{[(1R)-isobutanoyloxyethoxy]carbonylaminomethyl}-5-methyl-hexanoate hydrate from dosage forms provided by the present disclosure exhibits an in vitro dissolution profile in 50 mM sodium phosphate monobasic buffer at pH 6.8 and 37° C. stirred at 100 rpm (USP, Type II) in which about 83% of crystalline calcium (3S)-{[(1R)-isobutanoyloxyethoxy]carbonylaminomethyl}-5-methyl-hexanoate hydrate is released within about 3 hours; and about 100% of crystalline calcium (3S)-{[(1R)-isobutanoyloxyethoxy]carbonylaminomethyl}-5-methyl-hexanoate hydrate is released within about 6 hours. In certain of such embodiments, a tablet dosage form weighs about 500 mg and comprises about 32.7 wt-% (about 163.5 mg) crystalline calcium (3S)-{[(1R)-isobutanoyloxyethoxy]carbonylaminomethyl}-5-methyl-hexanoate hydrate. In certain embodiments, a tablet dosage form is prepared according to Example 13.

Kits

Crystalline calcium (3S)-{[(1R)-isobutanoyloxyethoxy]carbonylaminomethyl}-5-methyl-hexanoate hydrate or a pharmaceutical composition thereof may be included in a kit that may be used to administer the compound to a patient for treating a disease. A kit can include a pharmaceutical composition comprising crystalline calcium (3S)-{[(1R)-isobutanoyloxyethoxy]carbonylaminomethyl}-5-methyl-hexanoate hydrate suitable for administration to a patient and instructions for administering the pharmaceutical composition to a patient. A kit can include one or more containers for containing one or more pharmaceutical compositions and may include divided containers such as a divided bottle or a divided foil packet. A container can be any appropriate shape or form made of a pharmaceutically acceptable material. A particular container can depend on the dosage form and the number of dosage forms provided. Instructions provided with a kit can include directions for administration and may include a memory aid. Instructions supplied with a kit may be printed and/or supplied, for example, as an electronic-readable medium, a video cassette, an audiotape, a flash memory device, or may be published on an internet web site or distributed to a patient as an electronic mail. A memory aid may be a written memory aid, which contains information and/or instructions for the physician, pharmacist, and/or patient to facilitate compliance with a dosing regimen. A memory aid may also be mechanical or electronic. When a therapeutic regimen includes administration of crystalline calcium (3S)-{[(1R)-isobutanoyloxyethoxy]carbonylaminomethyl}-5-methyl-hexanoate hydrate and at least one other therapeutic agent, a kit can include the at least one other therapeutic agent in the same or separate container as the crystalline calcium (3S)-{[(1R)-isobutanoyloxyethoxy]carbonylaminomethyl}-5-methyl-hexanoate hydrate.

In certain embodiments, a kit comprises a pharmaceutical composition comprising crystalline calcium (3S)-{[(1R)-isobutanoyloxyethoxy]carbonylaminomethyl}-5-methyl-hexanoate hydrate and instructions for administering the pharmaceutical composition to a patient in need thereof for treating a disease chosen from a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation.

In certain embodiments, a kit comprises a pharmaceutical composition of crystalline calcium (3S)-{[(1R)-isobutanoyloxyethoxy]carbonylaminomethyl}-5-methyl-hexanoate hydrate and instructions for administering the pharmaceutical composition to a patient in need thereof for managing chronic pain. In certain embodiments, a kit comprises a pharmaceutical composition comprising (3S)-{[(1R)-isobutanoyloxyethoxy]carbonylaminomethyl}-5-methyl-hexanoate hydrate and an opioid agonist, and instructions for administering the pharmaceutical composition to a patient in need thereof for managing chronic pain. In certain embodiments, a kit comprises a pharmaceutical composition comprising (3S)-{[(1R)-isobutanoyloxyethoxy]carbonylaminomethyl}-5-methyl-hexanoate hydrate and an opioid agonist, and instructions for administering the pharmaceutical composition to a patient in need thereof for managing low back pain, muscle pain, cancer pain, arthritis pain, osteoarthritis pain, osteoporosis pain, fibromyalgia, pain associated with inflammatory bowel disease, pain associated with irritable bowel syndrome, or pain associated with rheumatoid arthritis.

Methods provided by the present disclosure include a method of increasing the storage lifetime of (3S)-{[(1R)-isobutanoyloxyethoxy]carbonylaminomethyl}-5-methyl-hexanoate, comprising forming crystalline calcium (3S)-{[(1R)-isobutanoyloxyethoxy]carbonylaminomethyl}-5-methyl-hexanoate hydrate. In certain embodiments, a method of increasing the storage lifetime of (3S)-{[(1R)-isobutanoyloxyethoxy]carbonylaminomethyl}-5-methyl-hexanoate, comprises forming crystalline calcium (3S)-{[(1R)-isobutanoyloxyethoxy]carbonylaminomethyl}-5-methyl-hexanoate hydrate, which exhibits characteristic scattering angles (2θ) at least at 5.1°±0.2°, 7.3°±0.2°, 8.0°±0.2°, 11.6°±0.2°, 16.3°±0.2°, 17.3°±0.2°, and 19.2°±0.2° in an X-ray powder diffractogram measured using Cu—$K_\alpha$ radiation.

Dose

Crystalline calcium (3S)-{[(1R)-isobutanoyloxyethoxy]carbonylaminomethyl}-5-methyl-hexanoate hydrate or a pharmaceutical composition thereof, can generally be used in an amount effective to achieve the intended purpose such as for use to treat diseases or disorders such as a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation. Crystalline calcium (3S)-{[(1R)-isobutanoyloxyethoxy]carbonylaminomethyl}-5-methyl-hexanoate hydrate, or a pharmaceutical composition thereof can be administered in a therapeutically effective amount.

The amount of crystalline calcium (3S)-{[(1R)-isobutanoyloxyethoxy]carbonylaminomethyl}-5-methyl-hexanoate hydrate or a pharmaceutical composition thereof that will be effective in the treatment of a particular disease or disorder will depend on the nature of the disorder or condition, and can be determined by standard clinical techniques known in the art as previously described. In addition, in vitro or in vivo assays may optionally be employed to help identify optimal dosage ranges. The amount of crystalline calcium (3S)-{[(1R)-isobutanoyloxyethoxy]carbonylaminomethyl}-5-methyl-hexanoate hydrate or a pharmaceutical composition thereof administered will depend on, among other factors, the subject being treated, the weight of the subject, the severity of the affliction, the manner of administration and the judgment of the prescribing physician.

A dose may be delivered in a pharmaceutical composition by a single administration or by multiple applications of one or more dosage forms. In certain embodiments, crystalline calcium (3S)-{[(1R)-isobutanoyloxyethoxy]carbonylaminomethyl}-5-methyl-hexanoate hydrate or a pharmaceutical composition thereof can be delivered by oral sustained release administration. A sustained release formulation comprising crystalline calcium (3S)-{[(1R)-isobutanoyloxyethoxy]carbonylaminomethyl}-5-methyl-hexanoate hydrate or a pharmaceutical composition thereof can be administered twice per day or once per day. Dosing may be repeated intermittently, may be provided alone or in combination with other drugs, and may continue as long as required for effective treatment of the disease or disorder.

In certain embodiments, a dose or multiple doses of crystalline calcium (3S)-{[(1R)-isobutanoyloxyethoxy]carbonylaminomethyl}-5-methyl-hexanoate hydrate or a pharmaceutical composition thereof can provide between about 10 mg/day and about 2,000 mg/day of (3S)-aminomethyl-5-methyl-hexanoic acid, in certain embodiments between about 50 mg/day and about 1,000 mg/day of (3S)-aminomethyl-5-methyl-hexanoic acid, and in certain embodiments, between about 100 mg/day and about 600 mg/day of (3S)-aminomethyl-5-methyl-hexanoic acid. Appropriate dosage ranges for treating a particular disease may be readily determined by methods known to the skilled artisan.

Crystalline calcium (3S)-{[(1R)-isobutanoyloxyethoxy]carbonylaminomethyl}-5-methyl-hexanoate hydrate or a pharmaceutical composition thereof can be assayed in vitro and in vivo, for the desired therapeutic or prophylactic activity, prior to use in humans. A therapeutically effective dose of crystalline calcium (3S)-{[(1R)-isobutanoyloxyethoxy]carbonylaminomethyl}-5-methyl-hexanoate hydrate or a pharmaceutical composition thereof can provide therapeutic benefit without causing substantial toxicity and adverse side effects. Toxicity and adverse side effects of crystalline calcium (3S)-{[(1R)-isobutanoyloxyethoxy]carbonylaminomethyl}-5-methyl-hexanoate hydrate or a pharmaceutical composition thereof may be determined using standard pharmaceutical procedures and may be readily ascertained by the skilled artisan. The dose ratio between toxic and adverse side effects and therapeutic effect is the therapeutic index. A dose of crystalline calcium (3S)-{[(1R)-isobutanoyloxyethoxy]carbonylaminomethyl}-5-methyl-hexanoate hydrate or a pharmaceutical composition thereof can provide a circulating concentration of (3S)-aminomethyl-5-methyl-hexanoic acid that is within a therapeutically effective concentration with little or no toxicity or adverse side effects.

Combination Therapy

In certain embodiments, crystalline calcium (3S)-{[(1R)-isobutanoyloxyethoxy]carbonylaminomethyl}-5-methyl-hexanoate hydrate or a pharmaceutical composition thereof can be used in combination therapy with at least one other therapeutic agent. Crystalline calcium (3S)-{[(1R)-isobutanoyloxyethoxy]carbonylaminomethyl}-5-methyl-hexanoate hydrate or a pharmaceutical composition thereof and the at least one other therapeutic agent can act additively or synergistically. In certain embodiments, a pharmaceutical composition comprising crystalline calcium (3S)-{[(1R)-isobutanoyloxyethoxy]carbonylaminomethyl}-5-methyl-hexanoate hydrate can be administered concurrently with the administration of another therapeutic agent, which can be part of the same pharmaceutical composition as crystalline calcium (3S)-{[(1R)-isobutanoyloxyethoxy]carbonylaminomethyl}-5-methyl-hexanoate hydrate or the other therapeutic agent can be in a different pharmaceutical composition. In certain embodiments, a pharmaceutical composition comprising crystalline calcium (3S)-{[(1R)-isobutanoyloxyethoxy]carbonylaminomethyl}-5-methyl-hexanoate hydrate can be administered prior to or subsequent to administration of another therapeutic agent.

In certain embodiments, crystalline calcium (3S)-{[(1R)-isobutanoyloxyethoxy]carbonylaminomethyl}-5-methyl-hexanoate hydrate may be administered in combination with an amorphous form of calcium (3S)-{[(1R)-isobutanoyloxyethoxy]carbonylaminomethyl}-5-methyl-hexanoate, calcium (3S)-{[(1S)-isobutanoyloxyisobutoxy]carbonylaminomethyl}-5-methyl-hexanoate, or calcium (3S)-{[(1R)-benzoyloxyethoxy]carbonylaminomethyl}-5-methyl-hexanoate; another crystalline form of calcium (3S)-{[(1R)-isobutanoyloxyethoxy]carbonylaminomethyl}-5-methyl-hexanoate, calcium (3S)-{[(1S)-isobutanoyloxyisobutoxy]carbonylaminomethyl}-5-methyl-hexanoate, or calcium (3S)-{[(1R)-benzoyloxyethoxy]carbonylaminomethyl}-5-methyl-hexanoate; pregabalin; gabapentin; or a combination of any of the foregoing.

The additional therapeutic agent may be effective for treating a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation; or may be effective for treating a disease other than a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation. In certain embodiments in which crystalline calcium (3S)-{[(1R)-isobutanoyloxyethoxy]carbonylaminomethyl}-5-methyl-hexanoate hydrate is administered together with an additional therapeutic agent for treating a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation, each of the active agents may be used at lower doses than when used singly.

The weight ratio of crystalline calcium (3S)-{[(1R)-isobutanoyloxyethoxy]carbonylaminomethyl}-5-methyl-hexanoate hydrate to a second therapeutic agent may be varied and may depend upon the effective dose of each agent. A therapeutically effective dose of each compound can be used. Thus, for example, when crystalline calcium (3S)-{[(1R)-isobutanoyloxyethoxy]carbonylaminomethyl}-5-methyl-hexanoate hydrate is combined with another therapeutic agent, the weight ratio of the compound provided by the present disclosure to the second therapeutic agent can be from about 1000:1 to about 1:1000, from about 200:1 to about 1:200, from about 20:1 to about 1:20, and in certain embodiments, from about 50:1 to about 1:5.

Combinations of crystalline calcium (3S)-{[(1R)-isobutanoyloxyethoxy]carbonylaminomethyl}-5-methyl-hexanoate hydrate and a second therapeutic agent may also be within the aforementioned range, but in each case, an effective dose of each active compound can be used. In such combinations crystalline calcium (3S)-{[(1R)-isobutanoyloxyethoxy]carbonylaminomethyl}-5-methyl-hexanoate hydrate and second therapeutic agent may be administered separately or in conjunction. In addition, the administration of one element may be prior to, concurrent with, or subsequent to the administration of another therapeutic agent(s). Accordingly, crystalline calcium (3S)-{[(1R)-isobutanoyloxyethoxy]carbonylaminomethyl}-5-methyl-hexanoate hydrate may be used alone or in combination with other therapeutic agents that are known to be beneficial in treating a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation, or other therapeutic agents that affect receptors or enzymes that either increase the efficacy, safety, convenience, or reduce unwanted side effects or toxicity of crystalline calcium (3S)-{[(1R)-isobutanoyloxyethoxy]carbonylaminomethyl}-5-methyl-hexanoate hydrate and/or metabolites thereof. Crystalline calcium (3S)-{[(1R)-isobutanoyloxyethoxy]carbonylaminomethyl}-5-methyl-hexanoate hydrate and the other therapeutic agent may be co-administered, either in concomitant therapy or in a fixed combination. The additional therapeutic agent may be administered by the same or different route than the route used to administer crystalline calcium (3S)-{[(1R)-isobutanoyloxyethoxy]carbonylaminomethyl}-5-methyl-hexanoate hydrate or pharmaceutical composition thereof.

In certain embodiments, crystalline calcium (3S)-{[(1R)-isobutanoyloxyethoxy]carbonylaminomethyl}-5-methyl-hexanoate hydrate or a pharmaceutical compositions thereof may be administered to a patient for the treatment of a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation in combination with a therapy or therapeutic agent known or believed to be effective in the treatment of a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, and premature ejaculation, respectively, or in certain embodiments, a disease, disorder, or condition associated with a movement disorder, a gastrointestinal disorder, a psychotic disorder, a mood disorder, an anxiety disorder, a sleep disorder, a pulmonary disorder, a neurodegenerative disorder, an inflammatory disease, neuropathic pain, musculoskeletal pain, chronic pain, migraine, hot flashes, faintness attacks, urinary incontinence, ethanol withdrawal syndrome, or premature ejaculation, respectively.

In certain embodiments, crystalline calcium (3S)-{[(1R)-isobutanoyloxyethoxy]carbonylaminomethyl}-5-methyl-hexanoate hydrate or a pharmaceutical composition thereof may be administered to a patient for treating migraine in combination with a therapy or another therapeutic agent known or believed to be effective in treating migraine. Drugs useful for treating migraine can prevent a migraine from occurring, abort a migraine that is beginning, or relieve pain during the migraine episode.

Prophylactic migraine treatments reduce the frequency of migraines and include non-steroidal anti-inflammatory agents (NSAIDs), adrenergic beta-blockers, calcium channel blockers, tricyclic antidepressants, selective serotonin reuptake inhibitors, anticonvulsants, NMDA receptor antagonists, angiotensin converting enzyme (ACE) inhibitors, angiotensin-receptor blockers (ARBs), leukotriene-antagonists, dopamine agonists, selective 5HT-1D agonists, selective 5HT-1F agonists, AMPA/KA antagonists, CGRP (calcitonin gene related peptide) antagonists, NOS (nitric oxide synthase) inhibitors, blockers of spreading cortical depression, and other therapy. Examples of NSAIDs useful for preventing migraine include aspirin, ibuprofen, fenoprofen, flurbiprofen, ketoprofen, mefenamic acid, and naproxen. Examples of adrenergic beta-blockers useful for preventing migraine include acebutolol, atenolol, imilol, metoprolol, nadolol, pindolol, propranolol, and timolol. Examples of calcium channel blockers useful for preventing migraine include amlodipine, diltiazem, dotarizine, felodipine, flunarizine, nicardipine, nifedipine, nimodipine, nisoldipine, and verapamil. Examples of tricyclic antidepressants useful for preventing migraine include amitriptyline, desipramine, doxepin, imipramine, nortriptyline, and protriptyline. Examples of selective serotonin reuptake inhibitors (SSRIs) useful for preventing migraine include fluoxetine, methysergide, nefazodone, paroxetine, sertraline, and venlafaxine. Examples of other antidepressants useful for preventing migraine include bupropion, nefazodone, norepinephrine, and trazodone.

Examples of anticonvulsants (antiepileptics) useful for preventing migraine include divalproex sodium, felbamate, gabapentin, lamotrigine, levetiracetam, oxcarbazepine, tiagabine, topiramate, valproate, and zonisamide. Examples of NMDA receptor antagonists useful for preventing migraine include dextromethorphan, magnesium, and ketamine. Examples of angiotensin converting enzyme (ACE) inhibitors useful for preventing migraine include lisinopril. Examples of angiotensin-receptor blockers (ARBs) useful for preventing migraine include candesartan. Examples of leukotriene-antagonists useful for preventing migraine include zileuton, zafirlukast, montelukast, and pranlukast. Examples of dopamine agonists useful for preventing migraine include α-dihydroergocryptine. Examples of other therapy useful for preventing migraine include botulinum toxin, magnesium, hormone therapy, riboflavin, methylergonovine, cyproheptadine, and phenelzine, and complementary therapies such as counseling/psychotherapy, relaxation training, progressive muscle relaxation, guided imagery, diaphragmatic breathing, biofeedback, acupuncture, and physical and massage therapy.

Acute migraine treatments intended to eliminate or reduce the severity of the headache and any associated symptoms after a migraine has begun include serotonin receptor agonists, such as triptans (5-hydroxytryptophan (5-HT) agonists) such as almotriptan, eletriptan, frovatriptan, naratriptan, rizatriptan, sumatriptan, and zolmitriptan; ergotamine-based compounds such as dihydroergotamine and ergotamine; antiemetics such as metoclopramide and prochlorperazine; and compounds that provide analgesic effects.

Other examples of drugs used to treat migraine once started include, acetaminophen-aspirin, caffeine, cyproheptadine, methysergide, valproic acid, NSAIDs such as diclofenac, flurbiprofen, ketaprofen, ketorolac, ibuprofen, indomethacin, meclofenamate, and naproxen sodium, opioids such as codeine, meperidine, and oxycodone, and glucocorticoids including dexamethasone, prednisone and methylprednisolone.

Crystalline calcium (3S)-{[(1R)-isobutanoyloxyethoxy]carbonylaminomethyl}-5-methyl-hexanoate hydrate may also be administered in conjunction with drugs that are useful for treating symptoms associated with migraine such as nausea and vomiting, and depression. Examples of useful therapeutic agents for treating or preventing vomiting include, but are not limited to, 5-HT$_3$ receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam. Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as fluoxetine, fluvoxamine, paroxetine, and setraline; monoamine oxidase inhibitors such as isocarboxazid, pargyline, phenizine, and tranylcypromine; and psychostimulants such as dextroamphetamine and methylphenidate.

In certain embodiments, crystalline calcium (3S)-{[(1R)-isobutanoyloxyethoxy]carbonylaminomethyl}-5-methyl-hexanoate hydrate or a pharmaceutical composition thereof may be administered to a patient for treating neuropathic pain in combination with a therapy or another therapeutic agent known or believed to be effective in treating neuropathic pain. Examples of drugs useful for treating pain include opioid analgesics such as morphine, codeine, fentanyl, meperidine, methadone, propoxyphene, levorphanol, hydromorphone, oxycodone, oxymorphone, tramadol and pentazocine; non-opioid analgesics such as aspirin, ibuprofen, ketoprofen, naproxen, and acetaminophen; non-steroidal anti-inflammatory drugs such as aspirin, choline magnesium trisalicylate, diflunisal, salsalate, celecoxib, rofecoxib, valdecoxib, diclofenac, etodolac, fenoprofen, flubiprofen, ibuprofen, indomethacin, ketoprofen, ketorolac, meclofanamate, mefenamic acid, meloxicam, nabumetone, naproxen, oxaprozin, piroxicam, sulindac, and tometin; antiepileptics such as gabapentin, pregabalin, carbamazepine, phenyloin, lamotrigine, and topiramate; antidepressants such as duloxetine, amitriptyline, venlafaxine, nortryptyline, imipramine, and desipramine; local anesthetics such as lidocaine, and mexiletine; NMDA receptor antagonists such as dextropethorphan, memantine, and ketamine; N-type calcium-channel blockers such as ziconotide; vanilloid receptor-1 modulators such as capsaicin; cannabinoid receptor modulators such as sativex; neurokinin receptor antagonists such as lanepitant; other analgesics such as neurotropin; and other drugs such as desipramine, clonazepam, divalproex, oxcarbazepine, divalproex, butorphanol, valdecoxib, vicoprofen, pentazocine, propoxyhene, fenoprofen, piroxicam, indometnacin, hydroxyzine, buprenorphine, benzocaine, clonidine, flurbiprofen, meperidine, lacosamide, desvenlafaxine, and bicifadine.

In certain embodiments, a drug useful for treating neuropathic pain is chosen from propoxyphene, meperidine, hydromorphone, hydrocodone, morphine, codeine, 2-piperidinol-1-alkanol, eliprodil, ifenprodil, rofecoxib, celecoxib, salicylic acid, diclofenac, piroxicam indomethacin, ibuprofen, naproxen, gabapentin, carbemazepine, pregabalin, topiramate, valproic acid, sumatriptan, elitriptan, rizatriptan, zolmitriptan, naratriptan, flexeril, carisoprodol, robaxisal, norgesic, dantrium, diazepam, chlordiazepoxide, alprazolam, lorazepam, acetaminophen, nitrous oxide, halothane, lidocaine, etidocaine, ropivacaine, chloroprocaine, sarapin, bupivacaine, capsicin, desipramine, amitriptyline, doxepin, perphenazine, protriptyline, tranylcypromine, baclofen, clonidine, mexelitine, diphenhydramine, hydroxyzine, caffeine, prednisone, methyl-prednisone, decadron, sertraline, paroxetine, fluoxetine, tramadol, levodopa, dextromethorphan, substance P antagonists, and botulinum toxin. In certain embodiments, a drug useful for treating neuropathic pain can be chosen from a nicotine receptor partial agonist. Non-pharmacological therapies for treating neuropathic pain include transcutaneous electrical nerve stimulation, percutaneous electrical nerve stimulation, and acupuncture.

In certain embodiments, crystalline calcium (3S)-{[(1R)-isobutanoyloxyethoxy]carbonylaminomethyl}-5-methyl-hexanoate hydrate or a pharmaceutical composition thereof may be administered to a patient for treating post-herpetic neuralgia in combination with a therapy or another therapeutic agent known or believed to be effective in treating post-herpetic neuralgia. Examples of drugs useful for treating post-herpetic neuralgia include antiviral agents such as amantadine, acyclovir, cidofovir, desciclovir, deoxyacyclovir, famciclovir, foscamet, ganciclovir, penciclovir, azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, edoxuidine, enviroxime, fiacitabine, foscamet, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine 3-azido-3-deoxythymidine, 2',3"-dideoxyadenosine (ddA), 2',3'-dideoxyguanosine (ddG), 2',3'-dideoxycytidine (ddC), 2',3'-dideoxythymidine (ddT), 2',3'-dideoxy-dideoxythymidine (d4T), 2'-deoxy-3'-thia-cytosine (3TC or lamivudime), 2',3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2',3'-dideoxy-2',3'-didehydro-2'-fluorothymidine (Fd4T), 2',3'-dideoxy-2'-beta-fluoroadenosine (F-ddA), 2',3'-dideoxy-2'-beta-fluoro-inosine (F-ddI), and 2',3'-dideoxy-2'-beta-fluorocytosine (F-ddC), trisodium phosphomonoformate, trifluorothymidine, 3' azido-3' thymidine (AZT), dideoxyinosine (ddI), and idoxuridine.

In certain embodiments, crystalline calcium (3S)-{[(1R)-isobutanoyloxyethoxy]carbonylaminomethyl}-5-methyl-hexanoate hydrate or a pharmaceutical composition thereof may be used to treat or manage perioperative and acute post surgical pain. Perioperative pain management generally refers to the 3 phases of surgery: preoperative, intraoperative, and postoperative, and the steps or measures instituted to prevent and alleviate the acute pain associated with surgery. Post-surgical pain, itself, is a complex response to tissue trauma during surgery that stimulates hypersensitivity of the central nervous system. The result is pain in areas not directly affected by the surgical procedure. When a patient undergoes surgery, tissues and nerve endings are traumatized, resulting in surgical incisional pain. This trauma overloads the pain receptors that send messages to the spinal cord, which becomes over stimulated. There is an initial afferent barrage of pain signals and a secondary inflammatory response. This combination contributes significantly to post-surgical pain. The resultant central sensitization is a type of post-traumatic stress to the spinal cord, which interprets any stimulation as painful and unpleasant. There is what is believed to be peripheral sensitization and central sensitization (increase in excitability of spinal neurons). These two process cause what is now referred to as a spinal "wind up," which is responsible for a decrease in pain threshold at the site of injury (surgical site) and in surrounding uninjured tissue. An optimal form of pain treatment is to provide treatment pre-, intra-, and postoperatively to prevent pain hypersensitivity development. It is not unusual for a patient to feel pain in movement or physical touch in locations far from the surgical site. Given that pain signals the presence of damage or disease within the body, the goal of perioperative pain management is to prevent, reduce, or eliminate pain and discomfort associated with surgery, while minimizing potential side effects and maximizing patient convenience. Poor perioperative pain management increases the possibility of post-surgical complications and interferes with patient recovery and return to normal activities of daily living. Acute pain in the perioperative setting can also be defined as pain that is present in a surgical patient because of preexisting disease, the surgical procedure, or a combination of disease-related and procedure-related sources.

It is expected that the optimal exposure to pregabalin for the perioperative management of acute post-surgical pain may be a stable therapeutic plasma concentration with less peak/trough variability. By maintaining sustained pregabalin exposure within a narrow therapeutic range, particularly during surgery and the first 24 hours post surgery, it is anticipated that crystalline calcium (3S)-{[(1R)-isobutanoyloxyethoxy]carbonylaminomethyl}-5-methyl-hexanoate hydrate may result in improved efficacy in reducing pain and opioid use in the target population. Crystalline calcium (3S)-{[(1R)-isobutanoyloxyethoxy]carbonylaminomethyl}-5-methyl-hexanoate hydrate may be formulated as immediate release (IR) and sustained release (SR) formulations. Crystalline calcium (3S)-{[(1R)-isobutanoyloxyethoxy]carbonylaminomethyl}-5-methyl-hexanoate hydrate may be formulated to have both IR and SR components in a single tablet. The IR component may be included to generate an immediate release in blood pregabalin concentrations to provide therapeutic levels of pregabalin during the surgical procedure that may prevent pain hypersensitivity (Woolf, *Anesth Analg* 1993, 77, 362-79; and Dahl et al., *Acta Anesthesiol Scand* 2004, 48(8), 1130-39). The SR formulation is expected to generate sustained blood pregabalin concentrations to provide longer lasting relief from pain.

Pregabalin has been shown to be useful in treating or managing perioperative and acute post-surgical pain (Hill et al., *Eur J Pain* 2001, 5, 119-124; Tiippana et al., *Anesth Analg* 2007, 104, 1545-56; Jokela et al., *Pain* 2008, 134, 106-112; Gilron, *Curr Opin Anaesthesiol* 2007, 20, 456-472; and Freedman and O'Hara, *Aesthetic Surgery J* 2008, 28(4), 421-424). In certain embodiments, crystalline calcium (3S)-{[(1R)-isobutanoyloxyethoxy]carbonylaminomethyl}-5-methyl-hexanoate hydrate may be administered in an amount from about 50 mg/day to about 900 mg/day, and in certain embodiments, from about 150 mg/day to about 600 mg/day, to a patient for the treatment of perioperative pain. In certain embodiments, crystalline calcium (3S)-{[(1R)-isobutanoyloxyethoxy]carbonylaminomethyl}-5-methyl-hexanoate hydrate may be administered in an amount such as to provide from about 25 mg-equivalents pregabalin/day to about 450 mg-equivalents pregabalin/day, and in certain embodiments, from about 75 mg-equivalents pregabalin/day to about 300 mg-equivalents pregabalin/day to a patient for the treatment of perioperative pain. Administration may be prior to surgery, such as for example, one or two days before surgery, on the day of surgery, and/or from about 1 to about 20 days post-surgery or other appropriate time period.

Crystalline calcium (3S)-{[(1R)-isobutanoyloxyethoxy]carbonylaminomethyl}-5-methyl-hexanoate hydrate may be administered together with another therapeutic agent useful for treating perioperative pain, such as for example, an opioid agonist. In certain embodiments, the other therapeutic agent such as an opioid agonist is administered to a patient for treating perioperative pain as a single pharmaceutical composition, which may be as sustained release oral formulation. In certain embodiments, crystalline calcium (3S)-{[(1R)-isobutanoyloxyethoxy]carbonylaminomethyl}-5-methyl-hexanoate hydrate is administered together with an opioid agonist chosen from tramadol, tapentadol, and oxycodone for treating perioperative pain.

Crystalline calcium (3S)-{[(1R)-isobutanoyloxyethoxy]carbonylaminomethyl}-5-methyl-hexanoate hydrate or pharmaceutical composition thereof may be administered singly or in combination with another therapeutic agent used to treat or manage chronic pain in a patient. Chronic pain is pain that persists for three months or more and includes low back pain, muscle pain, cancer pain, arthritis pain, osteoarthritis pain, osteoporosis pain, fibromyalgia, chronic neuropathic pain, chronic postoperative pain, pain associated with inflammatory bowel disease, pain associated with irritable bowel syndrome, and pain associated with rheumatoid arthritis.

Examples of agents used to treat or manage chronic pain include, for example, acetaminophen, amitriptyline, amytriptyline, aspirin, butorphanol, celecoxib, choline salicylate, diclofenac, diflunisal, duloxetine, etodolac, fentanyl, gabapentin, hydromorphone, hydroxyzine, ibuprofen, imipramine, indomethacin, ketoprofen, lidocaine, meperidine, methadone, morphine, nalbuphine, naproxen, oxycodone, oxymorphone, pentazocine, pramoxine, pregabalin, propoxyphene, rofecoxib, tapentadol, tolmetin, tramadol, trolamine salicylate, and valdecoxib.

In certain embodiments, crystalline calcium (3S)-{[(1R)-isobutanoyloxyethoxy]carbonylaminomethyl}-5-methyl-hexanoate hydrate may be administered together with an opioid agonist to treat chronic pain in a patient. Examples of opioid agonists include a phenanthrene such as codeine, morphine, thebaine, oripavine; a semisynthetic derivative such as diacetylmorphine (heroin), dihydrocodeine, hydrocodone, hydromorphone, nicomorphine, oxycodone, and oxymorphone; an anilidopiperidine such as fentanyl, alphamethylfentanyl, alfentanil, sufentanil, remifentanil, carfentanyl, and ohmefentanyl; a phenylpiperidine such as pethidine (meperidine), ketobemidone, MPPP, allylprodine, prodine, and PEPAP; a diphenylpropylamine derivative such as propoxyphene, dextropropoxyphene, dextromoramide, bezitramide, piritramide, methadone, dipipanone, levomethadyl acetate (LAAM), loperamide, and diphenoxylate; a benzomorphan derivative such as dezocine, pentazocine, phenazocine; an oripavine derivative such as buprenorphine, dihydroetorphine; and etorphine; a morphinan derivative such as butorphanol, nalbuphine, levorphanol, and levomethorphan; and others such as lefetamine, meptazinol, tilidine, tramadol, and tapentadol. In certain embodiments, an opioid agonist is chosen from alfentanil, allylprodine, alphaprodine, anileridine, benzylmorphine, bezitramide, brifentanil, buprenorphine, butorphanol, carfentanil, clonitazene, codeine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, mirfentanil, morphine, morphine-6-glucuronide, myrophine, nalbuphine, narceine, nicomorphine, norlevorphanol, normethadone, nociceptin/orphanin FQ (N/OFQ), normorphine, norpipanone, ohmefentanyl, opium, oxycodone, oxymorphone, papavereturn, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, trefentanil, and tilidine. Opioid agonists include compounds exhibiting an agonistic effect at an opioid receptor including a µ-, κ-, δ-, and/or nociceptin receptor. An opioid agonist may also exhibit agonist or antagonist activity at other receptors.

In certain embodiments, crystalline calcium (3S)-{[(1R)-isobutanoyloxyethoxy]carbonylaminomethyl}-5-methyl-hexanoate hydrate may be administered together with an opioid agonist chosen from tramadol, tapentadol, and oxycodone to treat chronic pain in a patient.

Tramadol (1R,2R or 1S,2S)-2-[(dimethylamino)methyl]-1-(3-methoxyphenyl)-cyclohexanol) is a synthetic, centrally acting analgesic that has been widely used for chronic pain management. Its analgesic effect results form two different pharmacologic actions. Tramadol displays a weak agonistic effect at the µ- and δ-opioid receptors and a weaker affinity for κ-opioid receptors (Grond and Sablotzky, *Clin Pharmacokinet* 2004, 43(13), 879-923)). Tramadol is formulated as a racemic mixture consisting of two enantiomers. The main activity of the (−)-enantiomer is the inhibition of the neuronal re-uptake of noradrenaline, whereas the (+)-enantiomer interacts with µ-opioid receptors and increases serotonin synaptic concentrations by blocking serotonin re-uptake. Once daily tramadol formulations are known. (Coluzzi and Mattia, *Therapeutics and Clinical Risk Management* 2007, 3(5), 819-29). Tramadol has been shown to be effective in treating chronic lower back pain (Ruoff et al., *Clinical Ther* 2003, 25(4), 1123-1141). Tramadol includes the compound (1R, 2R)-2-[(dimethylamino)methyl]-1-(3-methoxyphenyl)-cyclohexanol, (1S,2S)-2-[(dimethylamino)methyl]-1-(3-methoxyphenyl)-cyclohexanol, the O-desmethyl derivative of any of the foregoing, pharmaceutically acceptable salts of any of the foregoing, pharmaceutically acceptable N-oxides of any of the foregoing and pharmaceutically acceptable solvates of any of the foregoing. Synergistic effects of tramadol and anticonvulsant drugs such as gabapentin and pregabalin for treating pain have been reported (Codd et al., WO 2001/013904; Codd et al., U.S. Pat. No. 6,562,865; Codd et al., Pain 2008, 134, 254-262; Armenta et al., WO 2007/052999; and Keskinbora et al., *J Pain Symptom Manage* 2007, 34, 183-189).

Tapentadol ((−)-(1R,2R)-3-(3-dimethylamino-1-ethyl-2-methylpropyl)phenol hydrochloride; tapentadol HCl) is an analgesic drug having moderate µ-opioid receptor agonist and norepinephrine reuptake inhibition and is shown to have efficacy in acute and chronic pain models (Tzschentke et al., *J Pharm Expt'l Ther* 2007, 323(1), 265-276).

Advantages of co-administering oxycodone and pregabalin for treating neuropathic pain are recognized (Gatti et al., *Eur Neurol* 2009, 61, 129-137; and Hanna et al., *Eur J Pain* 2008, 12, 804-13).

Crystalline calcium (3S)-{[(1R)-isobutanoyloxyethoxy]carbonylaminomethyl}-5-methyl-hexanoate hydrate and the an opioid agonist may be formulated in the same pharmaceutical composition or separate pharmaceutical compositions. In certain embodiments, a pharmaceutical composition comprising crystalline calcium (3S)-{[(1R)-isobutanoyloxyethoxy]carbonylaminomethyl}-5-methyl-hexanoate hydrate and the an opioid agonist is a sustained release formulation. In certain embodiments, the sustained release formulation may be adapted to be administered to a patient once per day or twice per day. In certain embodiments, a dosage form may comprise about 50 mg to about 1,200 mg of crystalline calcium (3S)-{[(1R)-isobutanoyloxyethoxy]carbonylaminomethyl}-5-methyl-hexanoate hydrate, and about 10 mg to about 400 mg of the opioid agonist. In certain embodiments, the ratio of the amount of crystalline calcium (3S)-{[(1R)-isobutanoyloxyethoxy]carbonylaminomethyl}-5-methyl-hexanoate hydrate to the amount of opioid agonist in a dosage form is from about 1:4 to about 4:1.

In certain embodiments, crystalline calcium (3S)-{[(1R)-isobutanoyloxyethoxy]carbonylaminomethyl}-5-methyl-hexanoate hydrate may be administered together with selective serotonin reuptake inhibitor (SSRI) to treat chronic pain in a patient. In certain embodiments, an SSRI is chosen from cericlamine, citalopram, cyanodothiepin D,L-fenfluramine, dapoxetine, demethylsertraline, desmethylcitalopram, escitalopram, femoxetine, fluoxetine, fluvoxamine, ifoxetine, litoxetine, nefazaodone, norfluoxetine, paroxetine, sertraline, trazodone, and zimelidine. An SSRI functions by inhibiting the reuptake of serotonin by afferent neurons.

In certain embodiments, crystalline calcium (3S)-{[(1R)-isobutanoyloxyethoxy]carbonylaminomethyl}-5-methyl-hexanoate hydrate may be administered together with selective noradrenaline/norepinephrine reuptake inhibitor (SNR1) to treat chronic pain in a patient. In certain embodiments, an SNR1 is chosen from atomoxetine, bicifadine, buprorion, desipramine, fezolamine, hydroxybuproprion, lofepramine, maprotiline, mianserin, sibutramine, mirtazepine, nomifensine, oxaprotiline, reboxetine, and viloxazine.

In certain embodiments, crystalline calcium (3S)-{[(1R)-isobutanoyloxyethoxy]carbonylaminomethyl}-5-methyl-hexanoate hydrate may be administered together with a compound that inhibits the reuptake of both serotonin and norepinephrine to treat chronic pain in a patient. In certain embodiments, a compound that inhibits the reuptake of both serotonin and norepinephrine is chosen from clomipramine, desmethylclomipramine, duloxetine, imipramine, milnacipran, O-desmethylvenlafaxine, and venlafaxine.

Other agents that may be co-administered with crystalline calcium (3S)-{[(1R)-isobutanoyloxyethoxy]carbonylaminomethyl}-5-methyl-hexanoate hydrate or pharmaceutical composition thereof for treating chronic pain include nonsteroidal antiinflammatory drugs (NSAIDs) such as aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, and zomepirac; barbiturate sedatives such as amobarbital, aprobarbital, butabarbital, butabital, mephobarbital, metharbital, methohexital, pentobarbital, phenobartital, secobarbital, talbutal, theamylal, and thiopental; benzodiazepines such as chlordiazepoxide, clorazepate, diazepam, flurazepam, lorazepam, oxazepam, temazepam, and triazolam, $H_1$ antagonists such as diphenhydramine, pyrilamine, promethazine, chlorpheniramine, and chlorcyclizine; other sedatives such as glutethimide, meprobamate, methaqualone, and dichloralphenazone; skeletal muscle relaxants such as baclofen, carisoprodol, chlorzoxazone, cyclobenzaprine, methocarbamol, and orphrenadine; NMDA receptor antagonists such as dextromethorphan ((+)-3-hydroxy-N-methylmorphinan), dextrorphan ((+)-3-hydroxy-N-methylmorphinan), ketamine, memantine, pyrroloquinoline quinine, and cis-4-(phosphonomethyl)-2-piperidinecarboxylic acid; α-adrenergic active compounds such as doxazosin, tamsulosin, clonidine, and 4-amino-6,7-dimethoxy-2-(5-methanesulfonamido-1,2,3,4-tetra-hydroisoquinol-2-yl)-5-(2-pyridyl)quinazoline; tricyclic antidepressants such as amytriptiline, amoxapine, butryiptyline, clomipramine, desipramine, dosulepin hydrochloride, doxepin, imipramine, iprindole, lofepramine, nortriptyline, opipramol, protriptyline, and trimipramine; anticonvulsants such as carbamazepine and valproate; tachykinin (NK) antagonists such as antagonists, (aR,9R)-7-[3,5-bis(trifluoromethyl)benzyl]-8,9,10-,11-tetrahydro-9-methyl-5-(4-methylphenyl)-7H-[1,4]diazocino[2,1-g][1,7]na-phthridine-6-13-dione, 5-[[(2R,3S)-2-[(1R)-1-[3,5-bis(trifluorom-ethyl)phenyl]ethoxy-3-(4-fluorophenyl)-4-morpholinyl]methyl]-1,2-dihydro-3-H-1,2,4-triazol-3-one, lanepitant, dapitant, and 3-[[2-methoxy-5-(trifluoromethoxy)phenyl]methylamino]-2-phenyl-piperidine (2S,3S); muscarinic antagonists such as oxybutin, tolterodine, propiverine, tropsium chloride, and darifenacin; COX-2 inhibitors such as celecoxib, rofecoxib and valdecoxib; non-selective COX inhibitors such as nitroflurbiprofen; coal-tar analgesics such as paracetamol; neuroleptics such as droperidol; vanilloid receptor agonists such as resinferatoxin; β-adrenergic compounds such as propranolol; local anaesthetics such as mexiletine; corticosteriods such as dexamethasone; serotonin receptor agonists and antagonists; cholinergic (nicotinic) analgesics; and PDEV inhibitors, such as sildenafil, vardenafil, and taladafil.

Crystalline calcium (3S)-{[(1R)-isobutanoyloxyethoxy]carbonylaminomethyl}-5-methyl-hexanoate hydrate and the other agent for treating pain such as an SSRI, SNRI, a compound that inhibits the reuptake of both serotonin and norepinephrine, or other agent for treating pain may be formulated in the same pharmaceutical composition or separate pharmaceutical compositions. In certain embodiments, a pharmaceutical composition comprising crystalline calcium (3S)-{[(1R)-isobutanoyloxyethoxy]carbonylaminomethyl}-5-methyl-hexanoate hydrate and the other agent for treating chronic pain is a sustained release formulation. In certain embodiments, the sustained release formulation may be adapted to be administered to a patient once per day or twice per day. In certain embodiments, a dosage form may comprise about 50 mg to about 1,200 mg of crystalline calcium (3S)-{[(1R)-isobutanoyloxyethoxy]carbonylaminomethyl}-5-methyl-hexanoate hydrate, and about 10 mg to about 1,200 mg of the other agent for treating pain. In certain embodiments, the ratio of the amount of crystalline calcium (3S)-{[(1R)-isobutanoyloxyethoxy]carbonylaminomethyl}-5-methyl-hexanoate hydrate to the amount of opioid agonist in a dosage form is from about 1:200 to about 200:1; from about 1:50 to about 50:1, from about 1:10 to about 10:1, and in certain embodiments from about 1:4 to about 4:1.

In certain embodiments, calcium (3S)-{[(1R)-isobutanoyloxyethoxy]carbonylaminomethyl}-5-methyl-hexanoate, calcium (3S)-{[(1S)-isobutanoyloxyisobutoxy]carbonylaminomethyl}-5-methyl-hexanoate, or calcium (3S)-{[(1R)-benzoyloxyethoxy]carbonylaminomethyl}-5-methyl-hexanoate may be coadministered with baclofen or a baclofen prodrug such as (3R)-4-{[(1S)-2-methyl-1-(2-methylpropanoyloxy)propoxy]carbonylamino}-3-(4-chlororphenyl)butanoic acid or other baclofen prodrugs disclosed in Gallop et al., U.S. Pat. No. 7,109,239, which is incorporated by reference in its entirety.

EXAMPLES

The following examples describe in detail the preparation, properties, and uses of calcium (3S)-{[(1R)-isobutanoyloxyethoxy]carbonylaminomethyl}-5-methyl-hexanoate and crystalline calcium (3S)-{[(1R)-isobutanoyloxyethoxy]carbonylaminomethyl}-5-methyl-hexanoate hydrate. It will be apparent to those skilled in the art that many modifications, both to materials and methods, may be practiced without departing from the scope of the disclosure.

Example 1

O-[(1R)-Isobutanoyloxyethyl]S-methyl thiocarbonate (5)

O-(1-Isobutanoyloxyethyl) S-methyl thiocarbonate (180 g), prepared as described in Gallop et al., U.S. Pat. No. 7,227,028, and lipase from *Candida antarctica*, immobilized on acrylic resin, (8.0 g) was stirred in phosphate buffered saline, pH 7.2, (1.6 L) at room temperature. The progress of the reaction was monitored by $^1$H-NMR using the chiral solvating agent [(R)-(+)-2,2,2-trifluoro-1-(9-anthryl)ethanol] and was complete within 16 h. The reaction mixture was diluted with ether and the ether layer separated and filtered through a pad of Celite to remove the enzyme. The ether phase was washed repeatedly with water then brine, and dried over anhydrous $Na_2SO_4$. Removal of the solvent in vacuo afforded a quantitative yield (90 g) of the title compound (5) as a single enantiomer. The absolute configuration was established by: (i) conversion to compound (6) (see Example 2 below); (ii) reaction of (6) with gabapentin to afford 1-{[(α-(R)-isobutanoyloxyethoxy)carbonyl]aminomethyl}-1-cyclohexane acetic acid; and (iii) correlation with the product formed by stereoselective Baeyer-Villiger oxidation of 1-{[(α-(R)-isobutanoylethoxy)carbonyl]aminomethyl}-1-cyclohexane acetic acid as described in Gallop et al., U.S. Pat. No. 6,927,036. $^1$H NMR (CDCl$_3$, 400 MHz): δ 1.16 (3H, d, J=7.6 Hz), 1.18 (3H, d, J=7.0 Hz), 1.50 (3H, d, J=5.6 Hz), 2.34 (3H, s), 2.55 (1H, hept, J=7.2 Hz), 6.92 (1H, q, J=5.6 Hz). $^1$H NMR in presence of chiral solvating agent, (R)-(−)-2,2,2-trifluoro-1-(9-anthryl)ethanol: 1.18 (6H, m), 1.495 (1.5H, d, J=5.2 Hz), 1.498 (1.5H, d, J=5.6 Hz), 2.334 (1.5H, s), 2.337 (1.5H, s), 2.555 (0.5H, sept, J=7.2 Hz), 2.558 (0.5H, sept, J=7.2 Hz), 6.917 (0.5H, q, J=5.6 Hz), 6.921 (0.5H, q, J=5.6 Hz).

Example 2

{[(1R)-Isobutanoyloxyethoxy]carbonyloxy}succinimide (6)

The title compound (6) was prepared from compound (5) by following the method disclosed in Example 9 of Gallop et al., U.S. Pat. No. 7,227,028. For example, to a solution of compound (5) (1 g, 4.8 mmol) in $CH_2Cl_2$ (10 mL) was added N-hydroxysuccinimide (1.1 g, 9.5 mmol) and the reaction mixture cooled to 0° C. A solution of 32% (V/v) peracetic acid (3.4 mL, 1.1 g, 14.4 mmol) was added dropwise over a period of 10 min and the solution stirred at room temperature for 3 h. The reaction mixture was diluted with ether (50 mL) and washed with water (2×10 mL), saturated sodium bicarbonate solution (10 mL) and brine (10 mL), then dried over anhydrous sodium sulfate, filtered and concentrated in vacuo to give the title compound (6) as a colorless oil (1 g, 77%). After trituration with hexane (20 mL) the title compound (6) was obtained as a white solid. $^1$H NMR (CDCl$_3$, 400 MHz): δ 1.17 (d, J=6.8 Hz, 6H), 1.56 (d, J=5.6 Hz, 3H), 2.55 (m, 1H), 2.82 (s, 4H), 6.80 (q, J=5.2 Hz, 1H).

Example 3

(3S)-{[(1R)-Isobutanoyloxyethoxy]carbonylaminomethyl}-5-methyl-hexanoic Acid (1-R)

Compound (6) (52.8 g, 0.193 mol) and pregabalin (31.7 g, 0.199 mol) were stirred in a mixture of acetonitrile and water (200 mL, 4:1) at room temperature for 16 h, and the acetonitrile removed in vacuo. The residue was partitioned between MTBE and water, and the MTBE layer was washed with water then brine, and dried over anhydrous $Na_2SO_4$. Removing the solvent in vacuo afforded the title compound (1-R) (61.3 g, 100% yield) as a colorless oil. $^1H$ NMR ($CDCl_3$, 400 MHz): δ 0.90 (3H, d, J=6.4 Hz), 0.92 (3H, d, J=6.4 Hz), 1.17 (8H, m), 1.47 (2.7H, d, J=5.6 Hz), 1.50 (0.3H, d, J=5.6 Hz), 1.66 (1H, hept, J=6.8 Hz), 2.19 (m, 1H), 2.27 (1H, dd, J=15.2, 7.6 Hz), 2.37 (1H, dd, J=15.2, 5.2 Hz), 2.54 (1H, hept, J=6.8 Hz), 3.08 (1H, m), 3.32 (1H, m), 5.00 (0.9H, br.t, J=6.2 Hz), 5.91 (0.1H, br.t, J=6.2 Hz), 6.76 (1H, q, J=5.6 Hz).

Example 4

Calcium (3S)-{[(1R)-Isobutanoyloxyethoxy]carbonylaminomethyl}-5-methyl-hexanoate (3)

To a stirred solution of compound (1-R) (16.63 g, 52.5 mmol) in acetonitrile at 0° C. was added an aqueous solution of $NaHCO_3$ (4.28 g, 50.9 mmol) dropwise. The resulting mixture was stirred and sonicated for 1 h, then concentrated under reduced pressure to thoroughly remove acetonitrile. To the resulting solution was added dropwise an aqueous solution of $Ca(OAc)_2.H_2O$ (4.48 g, 25.4 mmol) with stirring at 0° C. The title compound (3) precipitated as a white solid, which was filtered, washed with cold water, then dried in vacuo to afford the title compound (3) as a white solid (10.33 g). The supernatant was lyophilized, and the resulting white powder was washed with water to afford a second crop (3.83 g) of the title compound (3). The title compound (3) was further crystallized from a variety of solvent systems as described below. $^1H$ NMR ($CD_3OD$, 400 MHz): δ 0.90 (6H, t, J=6.6 Hz), 1.14 (3H, d, J=7.2 Hz), 1.15 (3H, d, J=6.8 Hz), 1.19 (2H, m), 1.46 (2.7H, d, J=5.6 Hz), 1.48 (0.3H, d, J=5.6 Hz), 1.70 (1H, hept, J=6.8 Hz), 2.08 (2H, m), 2.15 (1H, m), 2.52 (1H, hept, J=6.8 Hz), 3.05 (1H, dd, J=13.6, 5.6 Hz), 3.13 (1H, dd, J=13.6, 5.6 Hz), 6.74 (1H, q, J=5.6 Hz).

In an alternate synthesis of compound (3), to a stirred solution of (1-R) (73 g, 0.23 mol) in 450 mL of absolute ethanol at −5° C. was dropwise added a solution of NaOH (8.83 g, 0.22 mol) in 80 mL of ethanol (addition took ~2 h to complete). The temperature was maintained below −5° C. during the addition of the basic solution. The reaction mixture was stirred for another hour at −5° C. and then gradually warmed to room temperature. To this stirred solution was added a solution of $CaCl_2.2H_2O$ (16.2 g, 0.11 mol) in 100 mL of ethanol. The resulting reaction mixture was stirred for 3 h at room temperature and then cooled in an ice bath without stirring. Crystalline NaCl was removed by filtration and the supernatant was concentrated by rotary evaporation to about one third of the original volume. De-ionized water was added to the solution to form the title compound (3) (70.2 g, in two crops, 91% yield), m.p. 111.4-116.0° C.

Example 5

Crystallization of Calcium (3S)-{[(1R)-Isobutanoyloxyethoxy]carbonylaminomethyl}-5-methyl-hexanoate (3)

From Ethanol-Water:
Compound (3) (4 g) was dissolved in 15 mL of absolute ethanol at 45° C. to form a clear solution. To this solution de-ionized water was slowly added until turbidity appeared (~15.5 mL of water). The mixture was then warmed to 45° C. to form a clear solution. The solution was cooled to room temperature to promote crystallization. The solid was filtered, dried in a vacuum dessicator at room temperature, and then dried at 45° C. in a vacuum oven overnight to afford crystalline (3a) as a hydrate (3.51 g, 87% recovery) as a white crystalline solid, m.p. 107.1-110.9° C. An X-ray powder diffractogram of crystalline hydrate (3a) prepared according to this method, obtained as described in Example 10, is shown in FIG. 1. $^1H$-NMR (400 MHz, $CD_3OD$): δ 6.74 (1H, q, J=5.6 Hz), 3.13 (1H, dd, J=13.6, 5.6 Hz), 3.05 (1H, dd, J=13.6, 5.6 Hz), 2.53 (1H, heptet, J=6.4 Hz), 2.08-2.15 (3H, m), 1.68 (1H, heptet, J=6.8 Hz), 1.48 (0.3H, d, J=5.2 Hz), 1.45 (2.7H, d, J=5.2 Hz), 1.10-1.25 (9H, m), 0.88-0.94 (m, 7H).

From Ethanol-Water (Alternative Conditions):
Compound (3) (2 g) was dissolved in 12 mL of absolute ethanol at 45° C. to form a clear solution. To this solution de-ionized water was slowly added until the solution became turbid (~24 mL of water). The mixture was then warmed to 45° C. to form a clear solution. The solution was slowly cooled to room temperature overnight with the product crystallizing from solution. The solid was filtered, dried in a vacuum dessicator at room temperature, and then dried at 45° C. in a vacuum oven overnight to afford crystalline hydrate (3a) (1.4 g, 70% recovery) as a white solid, m.p. 110.1-117.0° C.

Figure 2:
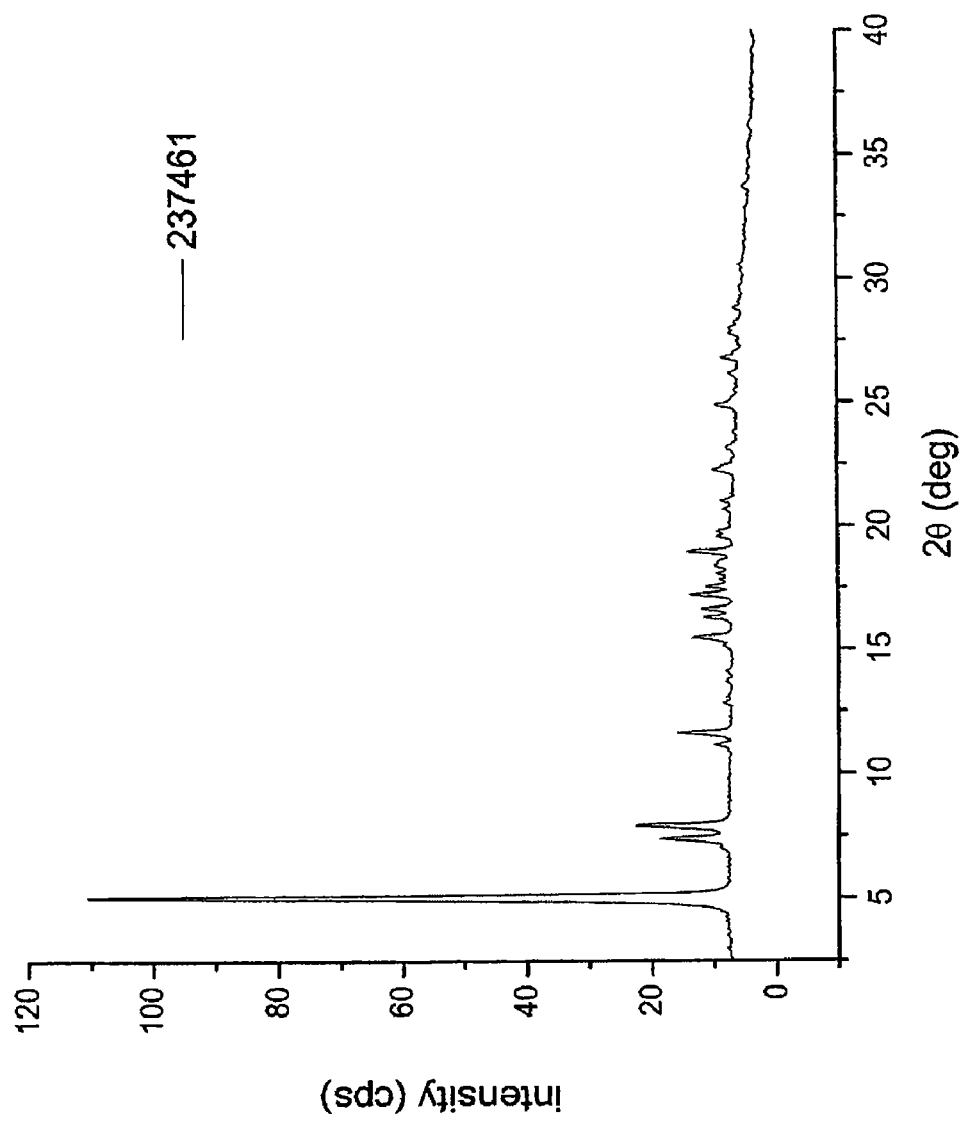
FIG. 2 shows an X-ray powder diffractogram of crystalline calcium (3S)-{[(1R)-isobutanoyloxyethoxy]carbonylaminomethyl}-5-methyl-hexanoate hydrate crystallized from isopropanol/water.

From Isopropanol-Water:
Compound (3) (6.87 g) was dissolved in 30 mL of isopropanol at 45° C. to form a clear solution, then 70 mL of water was added to afford a turbid mixture. The mixture was warmed to 50° C. to form a clear solution, which was then cooled first to room temperature and then to 4° C. overnight to promote crystallization. The solid was filtered, dried in a vacuum dessicator at room temperature, and then dried at 45° C. in a vacuum oven overnight to afford crystalline hydrate (3a) (5.06 g, 74% recovery) as a white solid, m.p. 111.7-117.0° C. An X-ray powder diffractogram of crystallinehydrate (3a) prepared according to this method, obtained as described in Example 7, is shown in FIG. 2.

Example 6

Alternate Synthesis of (3S)-{[(1R)-Isobutanoyloxyethoxy]carbonylaminomethyl}-5-methyl-hexanoic Acid (3)

Step A: 1-Chloro-2-methylpropyl methylthioformate (6a)

To a stirred solution of 1-chloro-2-methylpropyl methylformate in dichloromethane (DCM) was added a solution of sodium methanethiolate ($CH_3$—SNa) (1.0 eq.) in water at 0° C. and 0.02 eq. of tetrabutylammonium bromide. The reactants were stirred at 0° C. for 30 min and then diluted with dichloromethane (DCM). The dichloromethane layer was allowed to separate, then washed with water and brine, and dried with anhydrous sodium sulfate ($Na_2SO_4$). After rotary evaporation to remove the solvent, the title compound (6a) was obtained. $^1H$-NMR ($CDCl_3$): δ 1.05 (d, J=5.6 Hz, 3H), 1.07 (d, J=5.6 Hz, 3H), 2.18 (m, 1H), 2.38 (s, 3H), 6.34 (d, J=5.6 Hz, 1H) ppm.

Step B: 1-Methylthiocarbonyloxyethyl 2-methylpropanoate (6b)

1-Chloro-2-methylpropyl methylthioformate (6a) was added to a mixture of a carboxylic acid (4 eq.) and diisopropylethylamine (DIEA) (2 eq.). The mixture was stirred at 75° C. for 24 hrs. The mixture was then partitioned between water and methyl-tert-butyl ether (MTBE). The MTBE layer was washed three times with water, aqueous sodium bicarbonate (NaHCO$_3$), water, and brine, and then dried over anhydrous sodium sulfate (Na$_2$SO$_4$). After the solvent was removed by rotary evaporation the racemic title compound (6b) was obtained with 60-80% yield. $^1$H-NMR (CDCl$_3$): δ 1.18 (d, J=7.0 Hz, 3H), 1.16 (d, J=7.6 Hz, 3H), 1.50 (d, J=5.6 Hz, 3H), 2.34 (s, 3H), 2.55 (septet, J=7.2 Hz, 1H), 6.92 (q, J=5.6 Hz, 1H) ppm. $^1$H-NMR with chiral solvating agent (R)-(−)-2,2,2-trifluoro-1-(9-anthryl)ethanol: δ 1.18 (m, 6H), 1.495 (d, J=5.2 Hz, 1.5H), 1.50 (d, J=5.6 Hz, 1.5H), 2.33 (s, 1.5H), 2.34 (s, 1.5H), 2.56 (septet, J=7.2 Hz, 0.5H), 2.56 (septet, J=7.2 Hz, 0.5H), 6.92 (q, J=5.6 Hz, 0.5H), 6.92 (q, J=5.6 Hz, 0.5H) ppm.

Step C: (1R)-1-Methylthiocarbonyloxyethyl-2-methylpropanoate (5)

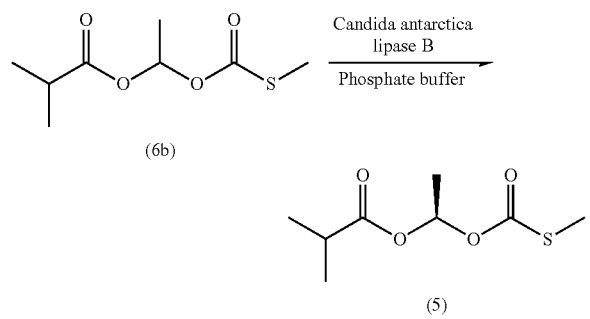

A 20-L, multi-necked, cylindrical reactor, fitted with a mechanical stirrer, a nitrogen inlet and an outlet connected to an oxidation bath and a bleach bath (14% NaOCl) to oxidize librated methanethiol and acetaldehyde was charged with racemic 1-methylthiocarbonyloxyethyl-2-methylpropanoate (6b) (5.32 kg, 25.8 mol) and 0.8 M phosphate buffer (10 L, pH 7.0). Solid supported *Candida antarctica* lipase B (125 g, Novozyme 435) was slowly added while stirred. The reaction mixture was stirred at room temperature (22-24° C.) for ca. 18 hours.

The reaction mixture was diluted with methyl tert-butyl ether (MTBE) (8 L) and the organic phase separated. The organic phase was washed with phosphate buffer (0.57 M, 2×5 L), water (10 L) and brine (7 L). The solid supported enzyme was removed by filtration and the organic phase was dried over sodium sulfate (Na$_2$SO$_4$), filtered and concentrated by rotary evaporation to afford the title compound (5) as light yellow oil. The product was further concentrated at 65° C. under reduced pressure to provide 2.45 kg of the title compound (5) (92% yield). $^1$H-NMR (CDCl$_3$): δ 1.17 (d, J=7.0 Hz, 3H), 1.18 (d, J=7.6 Hz, 3H), 1.59 (d, J=5.6 Hz, 3H), 2.34 (s, 3H), 2.55 (septet, J=7.2 Hz, 1H), 6.92 (q, J=5.6 Hz, 1H) ppm. $^1$H-NMR in presence of (R)-(−)-2,2,2-trifluoro-1-(9-anthryl)ethanol as chiral solvating agent (CDCl$_3$): δ 1.17 (d, J=7.2 Hz, 3H), 1.18 (d, J=7.2 Hz, 3H), 1.48 (d, J=5.6 Hz, 3H), 2.33 (s, 3H), 2.56 (septet, J=7.2 Hz, 1H), 6.92 (q, J=5.6 Hz, 1H) ppm.

For comparison, racemic 1-methylthiocarbonyloxyethyl-2-methylpropanoate: $^1$H-NMR in presence of (R)-(−)-2,2,2-trifluoro-1-(9-anthryl)ethanol as chiral solvating agent (CDCl$_3$): δ 1.18 (m, 6H), 1.49 (d, J=5.2 Hz, 1.5H), 1.50 (d, J=5.6 Hz, 1.5H), 2.33 (s, 1.5H), 2.34 (s, 1.5H), 2.55 (septet, J=7.2 Hz, 0.5H), 2.56 (septet, J=7.2 Hz, 0.5H), 6.92 (q, J=5.6 Hz, 0.5H), 6.92 (q, J=5.6 Hz, 0.5H) ppm.

Step D: {[(1R)-Isobutanoyloxyethoxy]carbonyloxy}succinimide (6)

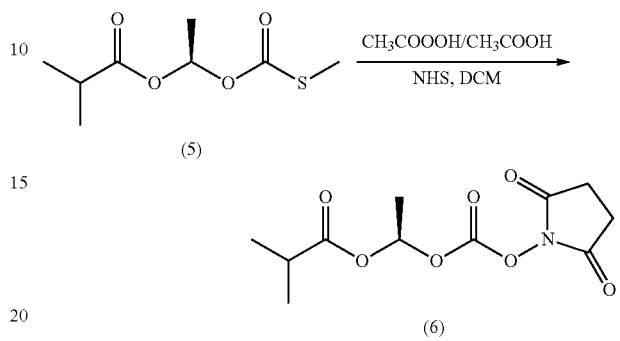

In a 20-L jacketed reaction vessel equipped with a mechanical stirrer, an internal thermometer and a nitrogen inlet was added (1R)-1-methylthiocarbonyloxyethyl-2-methylpropanoate (5) (1.44 kg, 7 mol), and N-hydroxysuccinimide (1.61 kg, 14 mol) in dichloromethane (DCM) (8 L). The resulting suspension was cooled to 9° C. A solution of peracetic acid in acetic acid (32%, 4.98 kg, 4.4 L; 21 mol) was slowly added while maintaining the reaction temperature between 9° C. and 15° C. The reaction mixture was then stirred at 9° C. for ca. 23 hours.

The reaction mixture was then diluted with water (3 L) and the organic phase was separated. The organic phase was washed with water (2×2 L), saturated potassium bicarbonate solution (4 L) and a solution of sodium thiosulfate (350 g in water 4 L). The organic phase was dried over sodium sulfate (Na$_2$SO$_4$) and volatiles were removed under vacuum, resulting in the crude product as a white-solid. To this solid was added 2-propanol (3 L) and hexane (3 L). The resulting slurry was warmed to 30° C. for 30 minutes. The resulting slurry was cooled for two hours using an ice-bath. The product was collected by filtration. The filter cake was washed with hexane (4 L) and dried under vacuum to provide the title compound (6) as a white solid (1 kg, 50% yield). $^1$H-NMR (CDCl$_3$): 1.17 (d, J=6.8 Hz, 3H), 1.18 (d, J=6.8 Hz, 3H), 1.60 (d, J=5.6 Hz, 3H), 2.58 (m, 1H), 2.83 (s, 4H), 6.80 (q, J=5.2 Hz, 1H) ppm.

Step E: (3S)-{[(1R)-Isobutanoyloxyethoxy]carbonylaminomethyl}-5-methyl-hexanoic Acid (3)

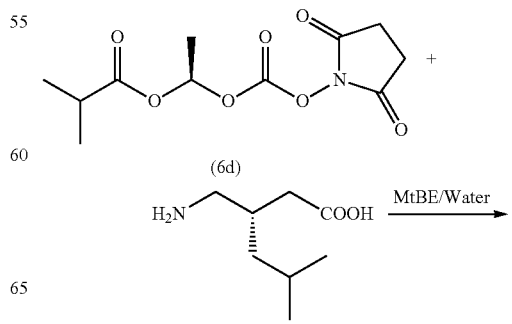

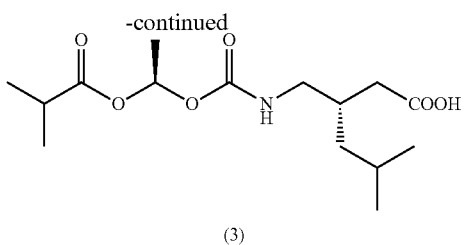

(3)

A 20-L pilot plant equipped with a mechanical stirrer and a nitrogen inlet was charged with NHS-carbonate, (1R)-1-(5-methylene-2-oxazolidinyloxycarbonyloxy)ethyl-2-methyl-propanoate (6), 1.31 kg, 4.7 mol) and (S)-pregabalin (431 g; overall 1.2 eq. of pregabalin) in a mixture of methyl tert-butyl ether (MTBE) and water (3:1; 10 L). The resulting suspension was stirred for 24 hours at room temperature.

The reaction mixture was then diluted with water (3 L). The organic phase was separated and washed with water (3×3 L), aqueous sulfuric acid (5%, 4 L), and water (4 L). The organic phase was dried over sodium sulfate ($Na_2SO_4$) and volatiles were removed under vacuum to provide the title compound (3) as a clear, viscous-oil (1.33 kg, 89% yield).

Example 7

Figure 4:
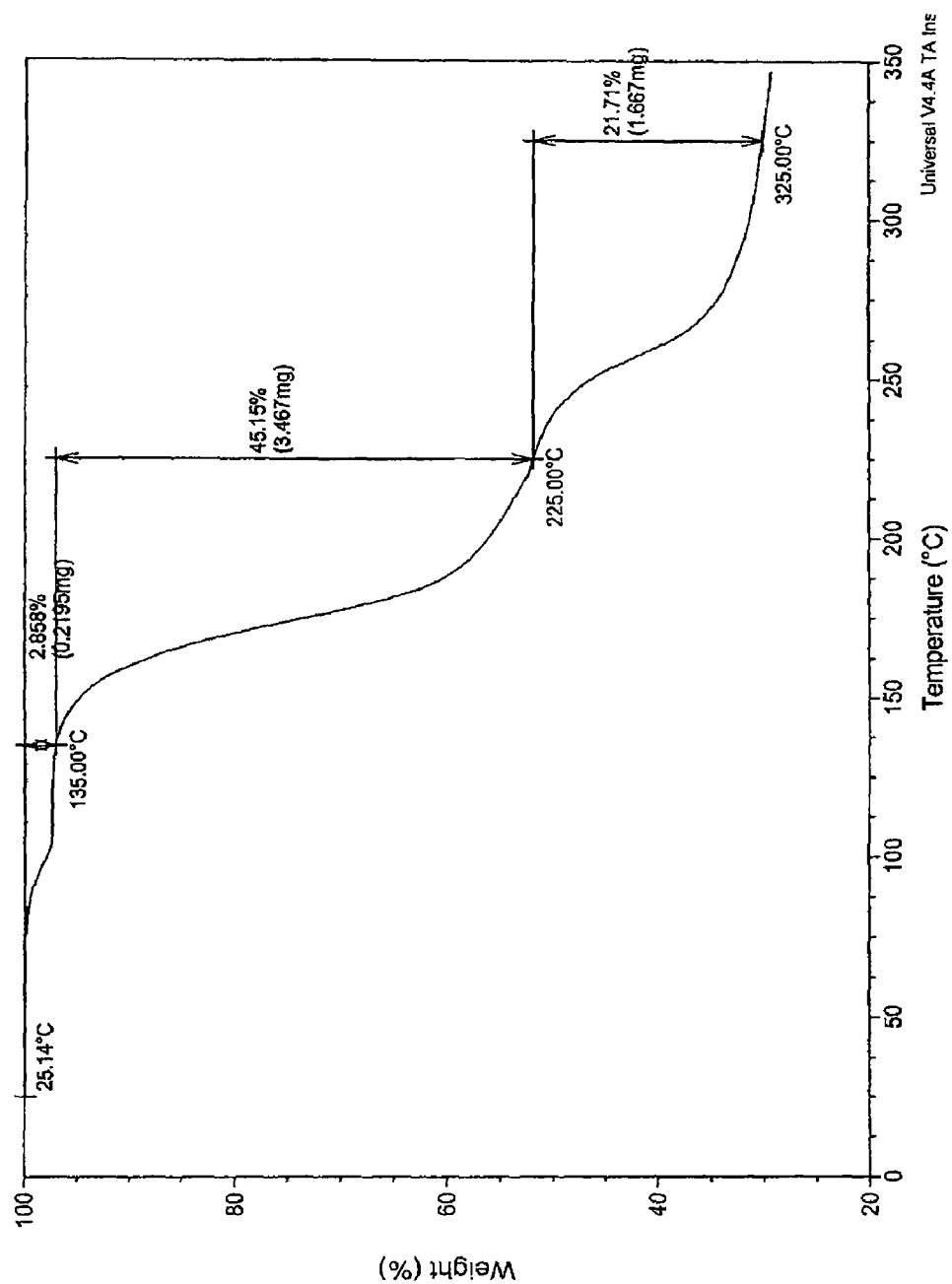
FIG. 4 shows thermal gravimetric analysis of crystalline calcium (3S)-{[(1R)-isobutanoyloxyethoxy]carbonylaminomethyl}-5-methyl-hexanoate hydrate.

Water Content and Elemental Analysis of Crystalline Calcium (3S)-{[(1R)-Isobutanoyloxyethoxy]carbonylaminomethyl}-5-methyl-hexanoate Hydrate Thermogravimetric analyses were performed using a TA Instruments 2950 thermogravimetric analyzer. Each sample was placed in an aluminum sample pan and inserted into the thermogravimetric furnace. The furnace was first equilibrated at 25° C., and then heated under a nitrogen atmosphere at a rate of 10° C./min to a final temperature of 350° C. Nickel and Alumel™ were used as calibration standards. Thermogravimetric analysis of calcium (3S)-{[(1R)-isobutanoyloxyethoxy]carbonylaminomethyl}-5-methyl-hexanoate hydrate crystallized from ethanol/water according to Example 5 showed about 3% weight loss from 25° C. to 75° C. and a 2.75% weight loss from 75° C. to 125° C. The weight loss between 75° C. to 125° C. can be attributed to hydrate water loss. Thermogravimetric analysis of a sample of crystalline calcium (3S)-{[(1R)-isobutanoyloxyethoxy]carbonylaminomethyl}-5-methyl-hexanoate hydrate having a weight loss of 2.86% between about 75° C. and 125° C. is shown in FIG. 4.

Coulometeric Karl Fischer (KF) analysis of water determination was performed using a Mettler Toledo DL39 Karl Fischer titrator. Approximately 14 mg of sample was dissolved in approximately 3.8 g of Hydranal-Coulomat AD. Approximately 0.9 g to 1.0 g of the extracted solution was placed in the KF titration vessel containing Hydranal-Coulomat AD and mixed for 10 seconds to ensure dissolution. The sample was then titrated by means of a generator electrode, which produces iodine by electrochemical oxidation. Karl Fischer analysis of calcium (3S)-{[(1R)-isobutanoyloxyethoxy]carbonylaminomethyl}-5-methyl-hexanoate hydrate crystallized from ethanol/water according to Example 5 determined the water content to be about 4.1% water. The water content of other batches of crystalline calcium (3S)-{[(1R)-isobutanoyloxyethoxy]carbonylaminomethyl}-5-methyl-hexanoate hydrate as determined by Karl Fischer analysis ranged from about 2.9% to about 4.5%.

Elemental microanalysis of the compounds was performed by Desert Analytics (Tucson, Ariz.). Theoretical elemental analysis for calcium (3S)-{[(1R)-isobutanoyloxyethoxy]carbonylaminomethyl}-5-methyl-hexanoate ($C_{30}H_{52}CaN_2O_{12}$) provides the following elemental composition: 53.55% C, 7.79% H, 4.16% N; and 5.96% Ca. Theoretical elemental analysis for calcium (3S)-{[(1R)-isobutanoyloxyethoxy]carbonylaminomethyl}-5-methyl-hexanoate monohydrate ($C_{30}H_{54}CaN_2O_{13}$) provides the following elemental composition: 52.16% C, 7.88% H, 4.05% N; and 5.80% Ca. The theoretical water content of the monohydrate is about 2.6% (w/w).

Experimental elemental analysis for crystalline calcium (3S)-{[(1R)-isobutanoyloxyethoxy]carbonylaminomethyl}-5-methyl-hexanoate hydrate crystallized from ethanol/water according to Example 5 provided the following elemental composition: 51.70% C, 7.66% H, 3.92% N; and 5.78% Ca. This experimental elemental analysis corresponds to a water content of about 3.9% (w/w), which is equivalent to about 1.6 moles water per mole calcium (3S)-{[(1R)-isobutanoyloxyethoxy]carbonylaminomethyl}-5-methyl-hexanoate.

Elemental analysis for another batch of crystalline calcium (3S)-{[(1R)-isobutanoyloxyethoxy]carbonylaminomethyl}-5-methyl-hexanoate hydrate showed the following elemental composition: 52.02% C, 7.97% H, 4.00% N; and 5.81% Ca.

The calcium content of crystalline calcium (3S)-{[(1R)-isobutanoyloxyethoxy]carbonylaminomethyl}-5-methyl-hexanoate hydrate was also determined by ion chromatography. Crystalline calcium (3S)-{[(1R)-isobutanoyloxyethoxy]carbonylaminomethyl}-5-methyl-hexanoate hydrate was dissolved in small amount of methanol and diluted with 20 mM methanesulfonic acid, then analyzed for calcium content by ion chromatography. The method employs IonPac CS12A (250×4 mm, Art. 46073 Dionex) as the separation column and IonPac CG12A (250×4 mm, Art. 46074 Dionex) pre column, operating at room temperature with conductivity detection. The mobile phase is isocratic (20 mM methanesulfonic acid) at flow rate of 1.0 mL/min. The calcium content in % w/w was determined by comparison of the IC peak areas with the reference standard made of calcium chloride, dihydrate. The $Ca^{2+}$ content of various batches of crystalline calcium (3S)-{[(1R)-isobutanoyloxyethoxy]carbonylaminomethyl}-5-methyl-hexanoate hydrate as determined by ion chromatography ranged from about 5.4% to about 5.8%.

The results of thermogravimetric analysis of water content, Karl Fischer analysis of water content, elemental analysis, and XRPD (see Examples 7 and 10) are consistent with crystalline calcium (3S)-{[(1R)-isobutanoyloxyethoxy]carbonylaminomethyl}-5-methyl-hexanoate hydrate having one molecule of water per molecule of calcium (3S)-{[(1R)-isobutanoyloxyethoxy]carbonylaminomethyl}-5-methyl-hexanoate incorporated into the crystal lattice; i.e., crystalline calcium (3S)-{[(1R)-isobutanoyloxyethoxy]carbonylaminomethyl}-5-methyl-hexanoate monohydrate, with a loosely bound water content. In other experiments, crystalline calcium (3S)-{[(1R)-isobutanoyloxyethoxy]carbonylaminomethyl}-5-methyl-hexanoate hydrate was shown to be hygroscopic.

Example 8

Differential Scanning Calorimetry of Crystalline Calcium (3S)-{[(1R)-Isobutanoyloxyethoxy]carbonylaminomethyl}-5-methyl-hexanoate Hydrate Differential scanning calorimetry was performed using a Puris Diamond differential scanning calorimeter (DSC) from Perkin Elmer. Following equilibration at 30° C., sample cells were heated under a nitrogen atmosphere at a rate of 10° C./min to a final temperature of 150° C. Indium metal was used as the calibration standard.

Crystalline calcium (3S)-{[(1R)-isobutanoyloxyethoxy]carbonylaminomethyl}-5-methyl-hexanoate hydrate prepared from ethanol/water according to Example 5 exhibited a melt transition from about 101° C. to about 116° C., with a peak maximum at about 110° C. and a ΔH of about 42.5 J/g.

Crystalline calcium (3S)-{[(1R)-isobutanoyloxyethoxy]carbonylaminomethyl}-5-methyl-hexanoate hydrate prepared from isopropanol/water according to Example 5 exhibited a melt transition from about 105° C. to about 122° C., with a peak maximum at about 115° C. and a ΔH of about 38.8 J/g.

Differential scanning calorimetry of another batch of crystalline calcium (3S)-{[(1R)-isobutanoyloxyethoxy]carbonylaminomethyl}-5-methyl-hexanoate hydrate was performed using a TA instruments Q2000 differential scanning calorimeter. The sample was placed into an aluminum DSC pan, and the weight accurately recorded. The pan was covered with a lid and then crimped. The sample cell was equilibrated at 25° C. and heated under a nitrogen purge at a rate of 10° C./minute, up to a final temperature of 250° C. Indium metal was used as the calibration standard. The DSC thermogram of crystalline calcium (3S)-{[(1R)-isobutanoyloxyethoxy]carbonylaminomethyl}-5-methyl-hexanoate hydrate exhibited a melt transition form about 91° C. to about 129° C. with a peak maximum at about 117° C. The broad transition is consistent with a phase transition from a crystalline to mesophasic form of calcium (3S)-{[(1R)-isobutanoyloxyethoxy]carbonylaminomethyl}-5-methyl-hexanoate hydrate.

Example 9

Figure 5:
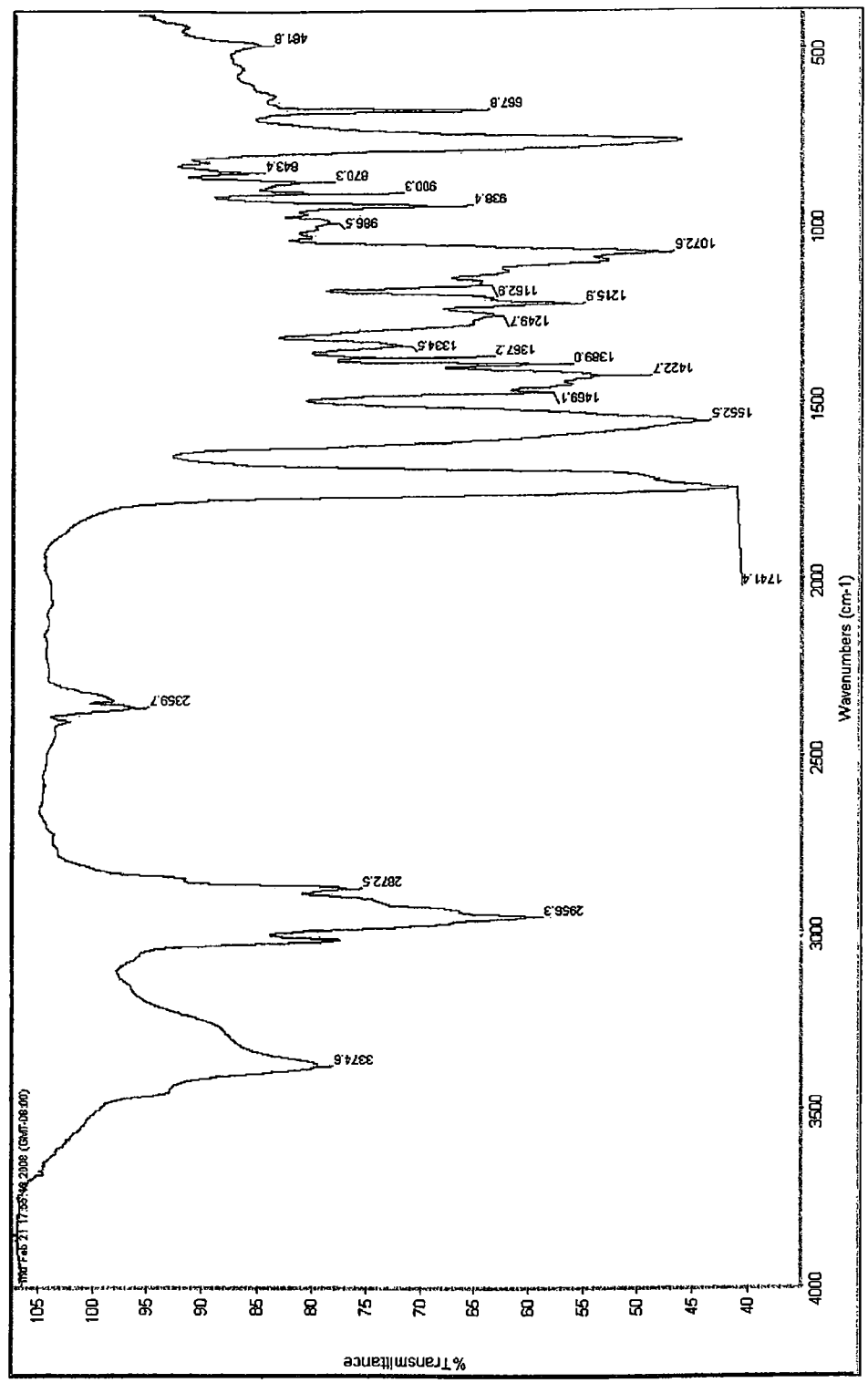
FIG. 5 shows an infrared spectra of crystalline calcium (3S)-{[(1R)-isobutanoyloxyethoxy]carbonylaminomethyl}-5-methyl-hexanoate hydrate.

IR Spectroscopy of Crystalline Calcium (3S)-{[(1R)-Isobutanoyloxyethoxy]carbonylaminomethyl}-5-methyl-hexanoate Hydrate A FT-IR spectrum of crystalline calcium (3S)-{[(1R)-isobutanoyloxyethoxy]carbonylaminomethyl}-5-methyl-hexanoate hydrate is shown in FIG. 5. The spectrum was acquired on the Nicolet Avatar 370 DTGS Fourier transform infrared (FT-IR) spectrophotometer (Thermo-Nicolet) equipped with a standard range potassium bromide (KBr) beam-splitter, and a deuterated triglycine sulfate (DTGS) detector. The sample was dissolved in $CHCl_3$ at a concentration of 100 mg/mL. The liquid sample was placed into the demountable path length cell (Thermo-Nicolet) prior to analysis. The spectra were obtained using 32 scans at 4 cm$^{-1}$ resolution and no post-processing was performed. Assignments for the major absorbance frequencies are listed in Table 1.

TABLE 1

FT-IR Absorbance Frequency Assignments based on the spectrum in FIG. 5.

| Wave Numbers (cm-1) | Functional Groups |
| --- | --- |
| 3375 | N—H stretching |
| 2956, 2873 | C—H stretching |
| 1741 | C=O stretching |
| 1552 | —C(=O)—NH— stretching |
|  | —C(=O)—O— stretching |
| 1250 (broad) | —C(=O)—O—R stretching |

Example 10

X-Ray Powder Diffraction Analysis

X-ray powder diffraction analyses were performed using either a Shimazdu XRD-6000 X-ray powder diffractometer or an Inel XRG-3000 diffractometer using Cu—Kα radiation (1.54178 Å). The Shimazdu instrument was equipped with a long fine focus X-ray tube. The tube voltage and amperage were set to 40 kV and 40 mA respectively. The divergence and scattering slits were set at 1° and the receiving slit was set at 150 µm. Diffracted radiation was detected by a NaI scintillation detector. A θ-2θ continuous scan at 3°/min from 2.5° to 40° 2θ was used. A silicon standard was analyzed to confirm the instrument alignment. Data was collected and analyzed using XRD-6100/7000 v.5.0 software. Samples were prepared for analysis by placing a compound on an aluminum holder with a silicon insert.

Data was collected on the Inel instrument at a resolution of 0.03° 2θ. The tube voltage and amperage were set to 40 kV and 30 mA, respectively. The monochromator slit was set at 5 mm×160 µm. The diffraction patterns were displayed from 2.5° to 40° 2θ. Samples were prepared for analysis by packing a compound into thin-walled glass capillaries. Each capillary was mounted onto a goniometer head that was motorized to permit spinning of the capillary during data acquisition. Samples were analyzed for 5 minutes and instrument calibration performed using a silicon reference standard.

Figure 6:
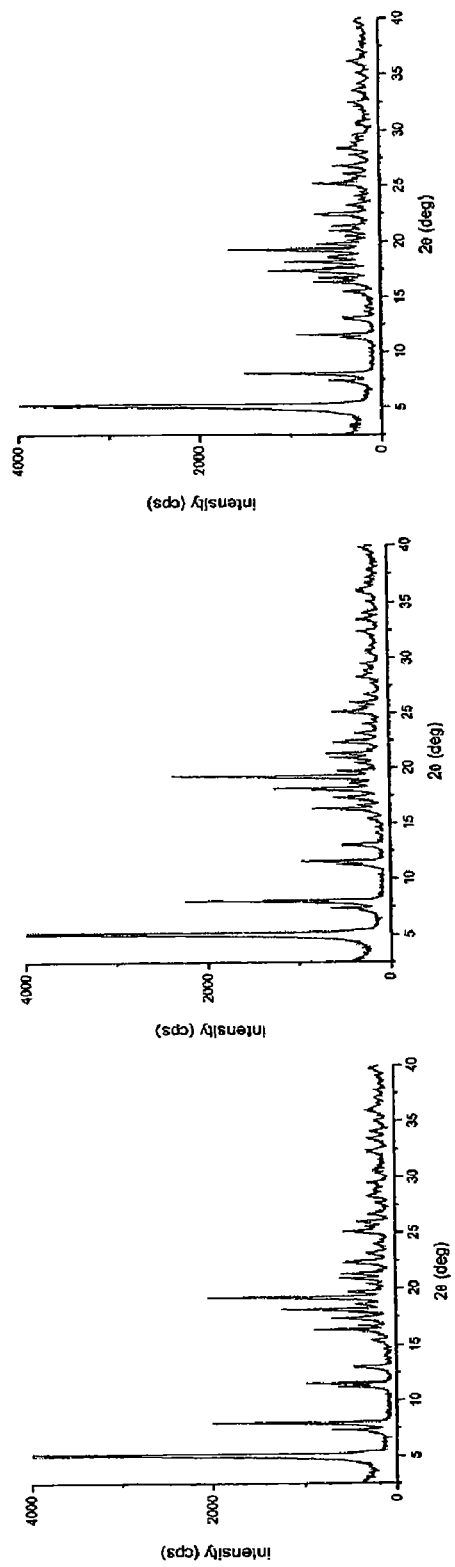
FIG. 6 shows X-ray powder diffratograms of different batches of crystalline calcium (3S)-{[(1R)-isobutanoyloxyethoxy]carbonylaminomethyl}-5-methyl-hexanoate hydrate.

The X-ray powder diffractograms for various batches of crystalline calcium (3S)-{[(1R)-isobutanoyloxyethoxy]carbonylaminomethyl}-5-methyl-hexanoate hydrate are shown in FIG. 1 and FIG. 2 and exhibit the same reflections for each batch, suggesting the same crystal form has been produced. A number of larger batches of crystalline calcium (3S)-{[(1R)-isobutanoyloxyethoxy]carbonylaminomethyl}-5-methyl-hexanoate hydrate prepared by crystallization from ethanol/water or isopropanol/water at temperature of 45° C. to room temperature had similar XPRD spectra to those shown in FIG. 6, suggesting that under these crystallization conditions, only one form of crystalline calcium (3S)-{[(1R)-isobutanoyloxyethoxy]carbonylaminomethyl}-5-methyl-hexanoate hydrate is generated. Characteristic scattering angles for various batches of calcium (3S)-{[(1R)-isobutanoyloxyethoxy]carbonylaminomethyl}-5-methyl-hexanoate hydrate shown in FIGS. 1, 2, and 6 are presented in Table 2.

TABLE 2

XRPD Scattering Angles.

| Batch A θ2θ(deg) | Batch B θ2θ(deg) | Batch C θ2θ(deg) | Batch D θ2θ(deg) |
| --- | --- | --- | --- |
| 5.0 | 5.1 | 5.1 | 5.16 |
|  | 5.3 | 5.3 | 5.34 |
| 7.4 | 7.3 | 7.32 | 7.38 |
| 7.9 | 7.96 | 7.98 | 8.02 |
|  | 11.24 | 11.24 | 11.30 |
| 11.6 | 11.52 | 11.54 | 11.58 |
|  | 12.92 | 12.92 |  |
|  | 13.04 | 13.08 | 13.12 |
| 15.5 |  |  | 15.50 |
| 16.3 | 16.26 | 16.28 | 16.32 |
| 16.6 |  |  | 16.70 |
| 17.2 | 17.28 | 17.30 | 17.36 |
|  |  |  | 17.54 |
|  | 18.08 | 18.10 | 18.16 |
|  | 18.58 |  | 18.56 |

TABLE 2-continued

XRPD Scattering Angles.

| Batch A θ2θ(deg) | Batch B θ2θ(deg) | Batch C θ2θ(deg) | Batch D θ2θ(deg) |
|---|---|---|---|
| 19.0 | 19.18 | 19.20 | 19.24 |
|  | 19.68 | 19.68 | 19.74 |
|  | 20.88 | 20.90 | 20.94 |
|  | 21.30 | 21.30 | 21.36 |
| 22.2 | 22.34 | 22.34 | 22.42 |
| 24.9 | 25.08 | 25.10 | 25.16 |
|  | 25.94 | 25.98 | 26.04 |

Example 11

Intracolonic Bioavailability of Calcium (3S)-{[(1R)-Isobutanoyloxyethoxy]carbonylaminomethyl}-5-methyl-hexanoate in Monkeys Male cynomologous monkeys weighing about 2.3 kg were used in the studies. Monkeys were fasted overnight prior to the study until 4 hours after dosing. Water was provided ad libitum.

Calcium (3S)-{[(1R)-isobutanoyloxyethoxy]carbonylaminomethyl}-5-methyl-hexanoate prepared according to Example 4 (after lyophilization and before crystallization according to Example 5) was prepared as a suspension (21.4 mg/mL) in 0.5% methyl cellulose/0.1% Tween-80 in $NaH_2PO_4$, pH 7.02.

Calcium (3S)-{[(1R)-isobutanoyloxyethoxy]carbonylaminomethyl}-5-methyl-hexanoate (1 mL/kg; 10 mg-eq pregabalin/kg) was administered intracolonically to 4 monkeys. Blood samples were collected at pre-dose and at 0.17, 0.25, 0.5, 1, 2, 4, 6, 8, 12, 18, and 24 hours post-dose. About 0.3 mL of blood was collected in pre-chilled $K_2EDTA$ tubes. The contents were gently vortexed at low speed to ensure that the sampled blood came into contact with EDTA while maintaining ice on the samples at all times. About 0.1 mL of the anti-coagulated blood was added to each of 2 pre-chilled cryovials that each contained about 0.3 mL of quenching media (i.e., methanol) within 5 minutes of bleed. Each cryovial was vortexed to ensure thorough mixing of the quenching media. The samples were then stored at −70° C.

Blood samples were analyzed by a sensitive and specific LC-MS/MS method for simultaneous determination of (3S)-{[(1R)-isobutanoyloxyethoxy]carbonylaminomethyl}-5-methyl-hexanoate and pregabalin.

The intracolonic bioavailability (F %) of pregabalin following intracolonic administration of calcium (3S)-{[(1R)-isobutanoyloxyethoxy]carbonylaminomethyl}-5-methyl-hexanoate was determined to be at least 5 times greater than the intracolonic bioavailability of pregabalin following intracolonic administration of an equivalent dose of pregabalin.

Example 12

Pregabalin Pharmacokinetics Following Colonic Administration of Crystalline Calcium (3S)-{[(1R)-Isobutanoyloxyethoxy]carbonylaminomethyl}-5-methyl-hexanoate Hydrate The pharmacokinetics of pregabalin and crystalline calcium (3S)-{[(1R)-isobutanoyloxyethoxy]carbonylaminomethyl}-5-methyl-hexanoate hydrate following intracolonic administration in monkeys was determined.

A group of four male cynomolgus monkeys received an intracolonic dose of pregabalin or crystalline calcium (3S)-{[(1R)-isobutanoyloxyethoxy]carbonylaminomethyl}-5-methyl-hexanoate hydrate (10 mg-eq pregabalin/kg). A 7-day wash-out period was allowed between treatments. Blood samples (300 µL) were collected from all animals prior to dosing and at intervals up to 24 hours post-dosing and immediately quenched in tubes containing $K_2EDTA$ to prevent hydrolysis. Two aliquots (100 µL each) were immediately quenched with 300 µL methanol. All quenched blood samples were subsequently analyzed for (3S)-{[(1R)-isobutanoyloxyethoxy]carbonylaminomethyl}-5-methyl-hexanoate free acid and pregabalin using LC-MS/MS.

Pregabalin was obtained from Teva (Peteh Tiqva, Israel). Crystalline calcium (3S)-{[(1R)-isobutanoyloxyethoxy]carbonylaminomethyl}-5-methyl-hexanoate hydrate was synthesized from commercial pregabalin according to Examples 1-6.

Cynomologus monkeys (body weight approximately 2.5 kg to 5.0 kg) were used in the study. Monkeys were fasted overnight and for the first 4 hours after dose administration. Water was provided ad libitum. For intracolonic administration, pregabalin or crystalline calcium (3S)-{[(1R)-isobutanoyloxyethoxy]carbonylaminomethyl}-5-methyl-hexanoate hydrate was suspended in 0.5% methylcellulose/0.1% Tween 80 in sodium phosphate buffer at pH 7.4. Blood samples were analyzed and pharmacokinetic analysis performed as described in Example 14.

Table 3 shows the mean pharmacokinetic parameters for pregabalin in blood following intracolonic administration of pregabalin or crystalline calcium (3S)-{[(1R)-isobutanoyloxyethoxy]carbonylaminomethyl}-5-methyl-hexanoate hydrate.

TABLE 3

Mean (SD) Pharmacokinetic parameters for pregabalin in blood after intracolonic dosing of pregabalin or crystalline calcium (3S)-{[(1R)-isobutanoyloxyethoxy]carbonylaminomethyl}-5-methyl-hexanoate hydrate in monkeys.

| | Dose | Prodrug | | Mean (SD) PK Parameters for Pregabalin | | | | | |
|---|---|---|---|---|---|---|---|---|---|
| Compound | (mg-eq PG/kg) | Dose [a] (mg/kg) | Vehicle | $C_{max}$ (µg/mL) | $T_{max}$ (hr) | $T_{1/2}$ (hr) | $AUC_{last}$ (µg × hr/mL) | $AUC_{inf}$ (µg × hr/mL) | F (%) |
| Pregabalin | 10 | NA | 0.5% MC/ 0.1% Tween 80 in Sodium phosphate buffer, pH 7.5 | 0.24 (0.10) | 0.50 (0.43) | 6.15 | 2.2 (1.2) | 3.1 | 2.7 (1.5) |

TABLE 3-continued

Mean (SD) Pharmacokinetic parameters for pregabalin in blood after intracolonic dosing of pregabalin or crystalline calcium (3S)-{[(1R)-isobutanoyloxyethoxy]carbonylaminomethyl}-5-methyl-hexanoate hydrate in monkeys.

| Compound | Dose (mg-eq PG/kg) | Prodrug Dose[a] (mg/kg) | Vehicle | $C_{max}$ (µg/mL) | $T_{max}$ (hr) | $T_{1/2}$ (hr) | $AUC_{last}$ (µg × hr/mL) | $AUC_{inf}$ (µg × hr/mL) | F (%) |
|---|---|---|---|---|---|---|---|---|---|
| (3a) | 10 | 20 | 0.5% MC/ 0.1% Tween 80 in Sodium phosphate buffer, pH 7.4 | 7.54 (1.89) | 0.88 (0.25) | 4.17 (1.15) | 54.5 (11.3) | 55.9 (12.1) | 63.0 (16.3) |

Abbreviations: PG = Pregabalin; SD = Standard deviation; $C_{max}$ = Maximum concentration achieved; $T_{max}$ = Time to reach maximum concentration; $T_{1/2}$ = Half-life; $AUC_{last}$ = Area under the concentration vs. time curve from time zero to the last time point with measurable concentration; $AUC_{inf}$ = Area under the concentration vs. time curve extrapolated to infinity; F = % Bioavailability relative to IV pregabalin at 8 mg/kg.
[a] Free acid equivalents.

Figure 7:
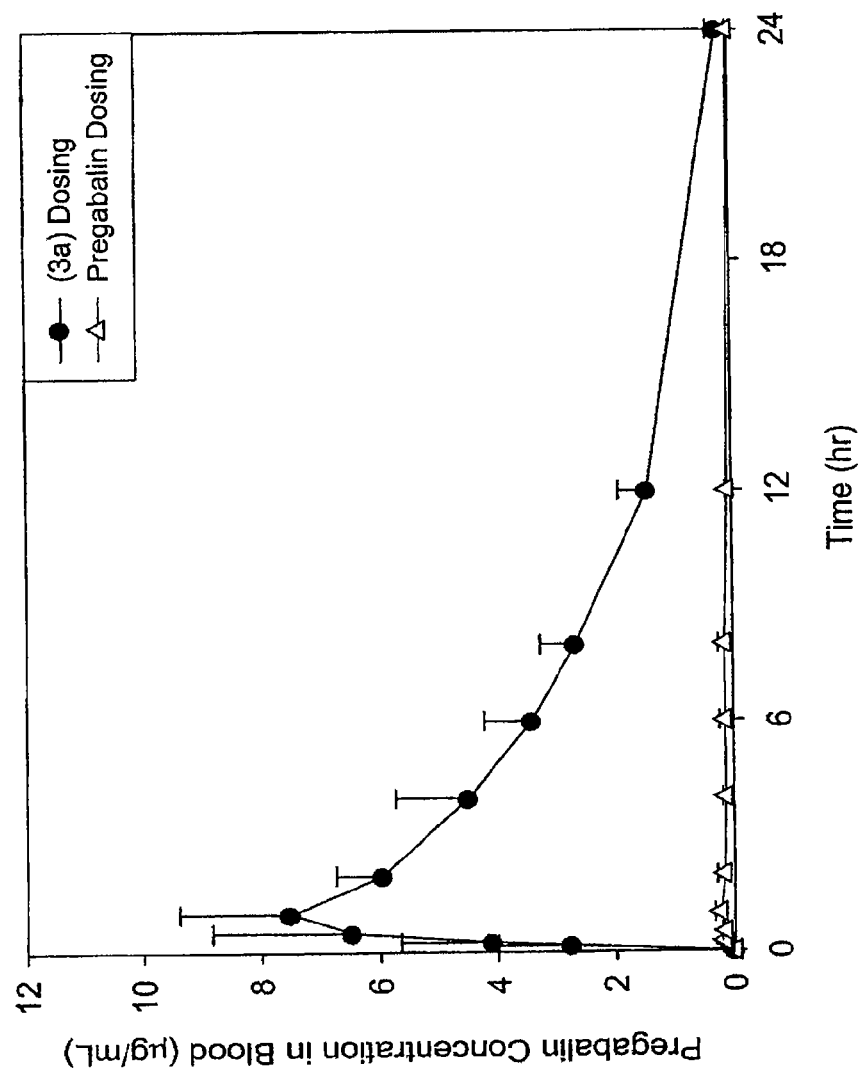
FIG. 7 shows mean (SD) concentrations of pregabalin in blood of monkeys following intracolonic dosing of pregabalin or crystalline calcium (3S)-{[(1R)-isobutanoyloxy-ethoxy]carbonylaminomethyl}-5-methyl-hexanoate hydrate at 10 mg-eq pregabalin/kg.

FIG. 7 shows the mean concentration-time profiles of pregabalin in blood after intracolonic dosing of either pregabalin or crystalline calcium (3S)-{[(1R)-isobutanoyloxyethoxy]carbonylaminomethyl}-5-methyl-hexanoate hydrate.

The greatly enhanced colonic bioavailability of pregabalin following administration of crystalline calcium (3S)-{[(1R)-isobutanoyloxyethoxy]carbonylaminomethyl}-5-methyl-hexanoate hydrate supports the development of sustained release formulations of the prodrug.

Example 13

Oral Dosage Forms of Crystalline Calcium (3S)-{[(1R)-Isobutanoyloxyethoxy]carbonylaminomethyl}-5-methyl-hexanoate Hydrate Tablet dosage formulations comprising crystalline calcium (3S)-{[(1R)-isobutanoyloxyethoxy]carbonylaminomethyl}-5-methyl-hexanoate hydrate were prepared. Crystalline calcium (3S)-{[(1R)-isobutanoyloxyethoxy]carbonylaminomethyl}-5-methyl-hexanoate hydrate was synthesized from commercial pregabalin according to Examples 1-6. Hydroxypropylmethyl cellulose (Methocel K100M Premium) was obtained from FMC Biopolymer; lactose (Direct Tableting 5X59009 (IR), Impalpable 5X73240 (SR)) was obtained from Kerry Bioscience); microcrystalline cellulose (Avicel PH 102 or Avicel PH 302) was obtained from Dow Chemical; colloidal silicon dioxide (Cab-O—Sil M5P) was obtained from Cabot; magnesium stearate was obtained from Mallinckrodt; and croscarmellose sodium (Ac-di-sol SD-711) was obtained from FMC Biopolymer.

The composition of crystalline calcium (3S)-{[(1R)-isobutanoyloxyethoxy]carbonylaminomethyl}-5-methyl-hexanoate hydrate formulations used in the monkey pharmacokinetic studies having 651 mg/unit dose are provided in Table 4. The composition of additional tablet formulations of crystalline calcium (3S)-{[(1R)-isobutanoyloxyethoxy]carbonylaminomethyl}-5-methyl-hexanoate hydrate are provided in Table 5.

TABLE 4

Composition of oral tablet formulations of crystalline calcium (3S)-{[(1R)-isobutanoyloxyethoxy]carbonylaminomethyl}-5-methyl-hexanoate hydrate.

| Component | IR Tablets % w/w | SR Tablets % w/w | SR1 Tablets % w/w | SR2 Tablets % w/w | Function |
|---|---|---|---|---|---|
| (3a) | 25.0[a] | 25.0[a] | 25.0[a] | 25.0[a] | Drug substance |
| Microcrystalline Cellulose (Avicel PH 102 or Avicel PH 302) | 17.75 | 15.25 | 12.12 | 8.25 | Filler/ Diluent |
| Anhydrous Lactose (Impalpable 5X73240 SR or Direct Tableting 5X59009 IR) | 53.25 | 45.75 | 36.38 | 24.75 | Filler/ Diluent |
| Hydroxypropyl Methylcellulose (Methocel K100M Premium) | — | 12.5 | 25.0 | 40.0 | Release-controlling Polymer |
| Colloidal Silicon Dioxide (Cab-O-Sil M5P) | — | 0.5 | 0.5 | 1.0 | Glidant |
| Magnesium Stearate | 1.0 | 1.0 | 1.0 | 1.0 | Lubricant |
| Croscarmellose Sodium (Ac-di-sol SD-711) | 3.0 | — | — | — | Disintegrant |
| Total Net | 100.0 | 100.0 | 100.0 | 100.0 | NA |

[a] 25.0 mg of crystalline calcium (3S)-{[(1R)-isobutanoyloxyethoxy]carbonylaminomethyl}-5-methyl-hexanoate hydrate is equivalent to 22.9 mg of the free acid of crystalline calcium (3S)-{[(1R)-isobutanoyloxyethoxy]carbonylaminomethyl}-5-methyl-hexanoate hydrate.

TABLE 5

Composition of oral tablet formulations of crystalline calcium (3S)-{[(1R)-isobutanoyloxyethoxy]carbonylaminomethyl}-5-methyl-hexanoate hydrate.

| Component | IR Tablets % w/w | IR Tablets mg/unit dose | SR1 Tablets % w/w | SR1 Tablets mg/unit dose | SR2 Tablets % w/w | SR2 Tablets mg/unit dose | Function |
|---|---|---|---|---|---|---|---|
| (3a) | 32.7[a] | 163.5 | 32.7 | 163.5[a] | 32.7 | 163.5[a] | Drug substance |
| Microcrystalline Cellulose (Avicel PH 102) | 15.7 | 78.5 | 10.2 | 51.0 | 6.5 | 32.5 | Filler/Diluent |
| Anhydrous Lactose (SR: Impalpable 5X73240, IR: Direct Tableting 5X59009) | 47.1 | 235.5 | 30.6 | 153.0 | 19.3 | 96.5 | Filler/Diluent |
| Hydroxypropyl Methylcellulose (Methocel K100M Premium) | — | — | 25.0 | 125.0 | 40.0 | 200.0 | Release-controlling Polymer |
| Colloidal Silicon Dioxide (Cab-O-Sil M5P) | — | — | 0.5 | 2.5 | 0.5 | 2.5 | Glidant |
| Magnesium Stearate | 1.5 | 7.5 | 1.0 | 5.0 | 1.0 | 5.0 | Lubricant |
| Croscarmellose Sodium (Ac-di-sol SD-711) | 3.0 | 15.0 | — | — | — | — | Disintegrant |
| Total Net | 100.0 | 500.0 | 100.0 | 500.0 | 100.0 | 500.0 | NA |

[a] 163 mg of crystalline calcium (3S)-{[(1R)-isobutanoyloxyethoxy]carbonylaminomethyl}-5-methyl-hexanoate hydrate (3a) is equivalent to 150 mg of the free acid of crystalline calcium (3S)-{[(1R)-isobutanoyloxyethoxy]carbonylaminomethyl}-5-methyl-hexanoate hydrate and 75 mg-equivalents of pregabalin.

A roller compaction granulation process was used for the manufacture of crystalline calcium (3S)-{[(1R)-isobutanoyloxyethoxy]carbonylaminomethyl}-5-methyl-hexanoate hydrate immediate and sustained release tablets. To prepare the tablets, all components were weighed. Crystalline calcium (3S)-{[(1R)-isobutanoyloxyethoxy]carbonylaminomethyl}-5-methyl-hexanoate hydrate was screened through a No. 20 or smaller mesh. All excipients except for magnesium stearate were screened through a No. 30 mesh. Crystalline calcium (3S)-{[(1R)-isobutanoyloxyethoxy]carbonylaminomethyl}-5-methyl-hexanoate hydrate and all excipients (except for magnesium stearate) were mixed in a V-blender. Magnesium stearate was passed through a No. 70 mesh screen and added to the blend, and ⅓ of the total magnesium stearate blended in the V-blender. The blend was passed through an Alexanderwerk WP 120×40V roller compactor (25 mm knurled rolls) to produce ribbons. The ribbons were milled by passing through the granulator on the roller compactor (screen sizes: 2 mm and 0.8 mm). The remaining magnesium stearate was added to the granules and mixed in a V-blender. The lubricated granules were formed into 500 mg tablets using concave, modified oval-shaped (0.5910-in× 0.2750-in) tooling.

Figure 8:
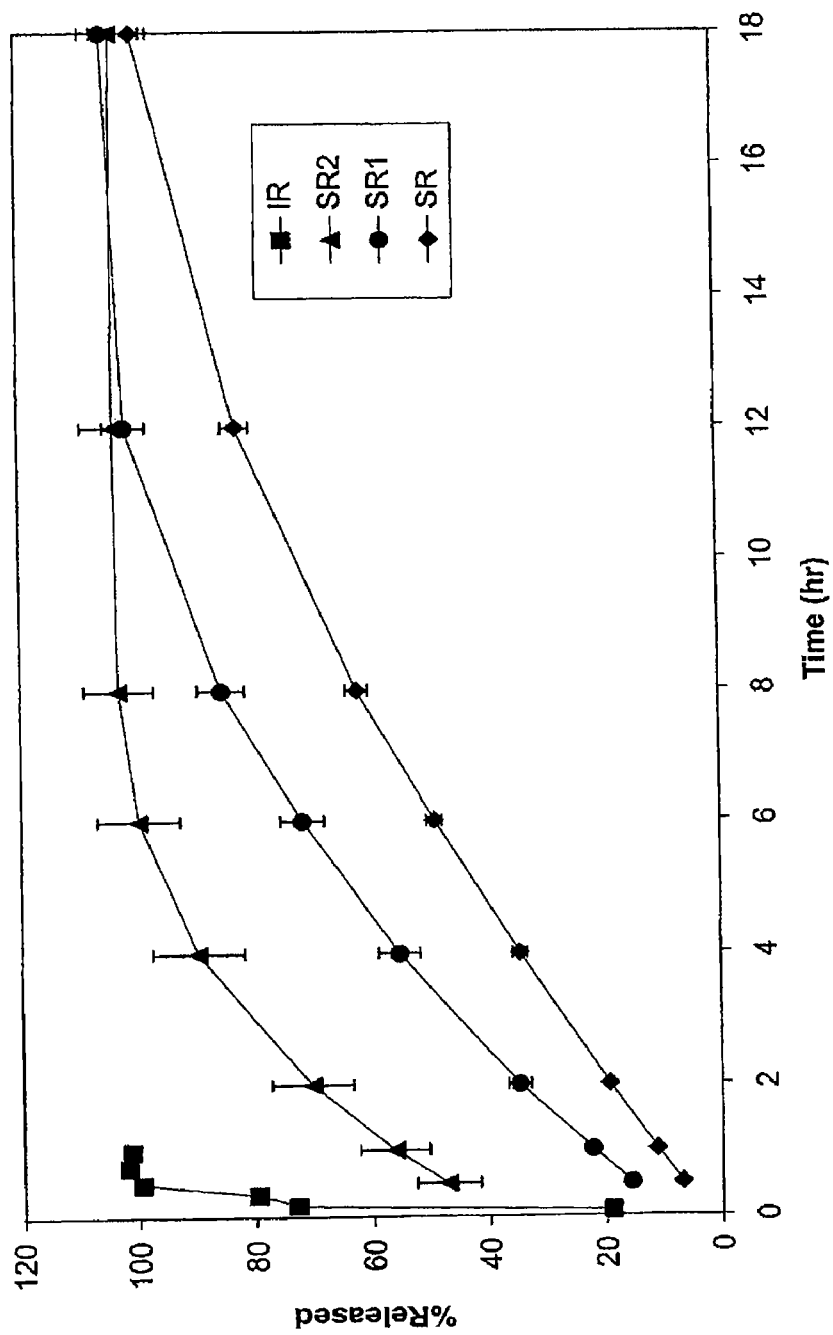
FIG. 8 shows dissolution profiles for tablets containing crystalline calcium (3S)-{[(1R)-isobutanoyloxyethoxy]carbonylaminomethyl}-5-methyl-hexanoate hydrate.

Dissolution testing was performed using the USP Apparatus II (paddle) method. To prepare the paddle dissolution test, six dissolution vessels were filled to contain 900 mL of 50 mM sodium phosphate monobasic buffer (pH 6.8) with 1% sodium lauryl sulfate and equilibrated to 37° C. One tablet was dropped into each vessel and the dissolution medium stirred at 100 rpm. A Japanese sinker was used if needed. Samples were withdrawn into HPLC vials at 15, 30, 45, and 60 minutes for IR tablets, and at 0.5, 2, 4, 6, 8, 12, 18, and 24 hours for SR tablets. The content of crystalline calcium (3S)-{[(1R)-isobutanoyloxyethoxy]carbonylaminomethyl}-5-methyl-hexanoate hydrate in the dissolution medium was determined by reversed-phase HPLC (Sunfire® C18, 4.6× 150 mm, 3.5 μm) equipped with a UV detector at 210 nm. An isocratic mobile phase (phosphate buffer/acetonitrile) was used. Dissolution profiles for 651 mg/unit dose IR and SR tablet formulations of crystalline calcium (3S)-{[(1R)-isobutanoyloxyethoxy]carbonylaminomethyl}-5-methyl-hexanoate hydrate prepared according the above procedure and having the compositions provided in Table 4 are shown in FIG. 8.

Example 14

Pregabalin Pharmacokinetics Following Administration of Oral Tablet Formulations One group of four male cynomolgus monkeys was used for the study. The mean body weight was approximately 2.9 kg at the start of the study and increased over the 9 months of the study to approximately 3.4 kg. The animals were fasted overnight and for the first 4 hours of the study after administration of each test formulation. Water was provided ad libitum.

All formulations were evaluated in a single group of four fasted male cynomolgus monkeys with at least 5 days washout between treatments. The IR tablet formulation was administered at 75 mg-eq pregabalin (1 tablet per animal). Three different SR tablet formulations were dosed orally at either 75 mg-eq. pregabalin or 69 mg-eq. pregabalin (1 tablet each per animal).

Blood samples were obtained from all animals at intervals up to 24 hours post-dosing. Approximately 0.3 mL of blood was collected in pre-chilled $K_2$EDTA tubes containing 0.3 mL of methanol. Within 30 minutes, the blood samples were stored at or below −70° C.

Quenched blood samples were frozen and stored at −20° C. prior to analysis. Samples were analyzed by a sensitive and specific LC-MS/MS method for simultaneous determination of (3S)-{[(1R)-isobutanoyloxyethoxy]carbonylaminomethyl}-5-methyl-hexanoate free acid and pregabalin concentrations.

Blood concentration data for all analytes were analyzed by non-compartmental methods using WinNonlin (WinNonlin™ Software, version 5.2, Pharsight Corp. Mountain View, Calif.). Non-compartmental analysis was performed on individual profiles in each animal. All concentration values below the limit of quantitation (BLQ) were treated as 0 (zero) for the pharmacokinetic analysis. Low concentration values at pre-dose were treated as BLQ. Nominal sample collection time points were used for the calculation of pharmacokinetic parameters. All concentration data were plotted using SigmaPlot (SigmaPlot™, Version 9.0, Systat Software Inc., Richmond, Calif.).

The maximum concentration ($C_{max}$) and time to $C_{max}$ ($T_{max}$) were obtained by observation. The apparent elimination half-life ($T_{1/2}$) was obtained by linear regression of three or more log-transformed data points in the terminal phase. The area under the concentration versus time curve ($AUC_{last}$) was obtained by the linear trapezoidal method using concentration data up to the last quantifiable concentration. The AUC value extrapolated to infinity ($AUC_{inf}$) was calculated as:

$$AUC_{inf} = AUC_{last} + C_{last}/\lambda_z$$

where $t_{last}$ is the time of the last quantifiable concentration ($C_{last}$) and $\lambda_z$ is the rate constant of the apparent terminal elimination phase.

The bioavailability (F) of pregabalin after extravascular dosing of pregabalin or prodrug was calculated by comparison to data following intravenous administration of pregabalin as follows:

$$F(\%) = 100 \times (AUC_{ex}/Dose_{ex})/(AUC_{iv}/Dose_{iv})$$

where $AUC_{ex}$ is the area under the pregabalin concentration versus time curve in μg×hr/mL following extravascular administration of pregabalin or crystalline calcium (3S)-{[(1R)-isobutanoyloxyethoxy]carbonylaminomethyl}-5-methyl-hexanoate hydrate formulation; $Dose_{ex}$ is the extravascular dose expressed in mg-equivalents of pregabalin/kg body weight; $AUC_{iv}$ is the area under the pregabalin concentration versus time curve in μg×hr/mL following intravenous administration of pregabalin; and $Dose_{iv}$ is the intravenous dose expressed in mg-equivalents of pregabalin/kg body weight.

The relative bioavailability ($F_{rel}$) of pregabalin after oral dosing of crystalline calcium (3S)-{[(1R)-isobutanoyloxyethoxy]carbonylaminomethyl}-5-methyl-hexanoate hydrate formulations was calculated by comparison to data following oral administration of LYRICA (pregabalin; Pfizer) as follows:

$$F_{rel}(\%) = 100 \times (AUC_{PO}/Dose_{PO})/(AUC_{Lyrica}/Dose_{Lyrica})$$

where $AUC_{PO}$ is the area under the pregabalin concentration versus time curve in μg×hr/mL following oral administration of crystalline calcium (3S)-{[(1R)-isobutanoyloxyethoxy]carbonylaminomethyl}-5-methyl-hexanoate hydrate formulations; $Dose_{PO}$ is the pregabalin dose expressed in mg-equivalents of pregabalin in crystalline calcium (3S)-{[(1R)-isobutanoyloxyethoxy]carbonylaminomethyl}-5-methyl-hexanoate hydrate formulations; $AUC_{Lyrica}$ is the area under the pregabalin concentration versus time curve in μg×hr/mL following oral administration of LYRICA formulation; and $Dose_{Lyrica}$ is oral dose expressed in mg of pregabalin in LYRICA formulation.

Table 6 shows the mean (SD) pharmacokinetic parameters for pregabalin in blood of monkeys following oral administration of pregabalin or crystalline calcium (3S)-{[(1R)-isobutanoyloxyethoxy]carbonylaminomethyl}-5-methyl-hexanoate hydrate tablet formulations.

TABLE 6

Pharmacokinetic parameters for pregabalin in blood after oral dosing of pregabalin capsules or crystalline calcium (3S)-{[(1R)-isobutanoyloxyethoxy]carbonylaminomethyl}-5-methyl-hexanoate hydrate formulations in monkeys.

| Compound | Dose (mg-eq PG) | Dose (mg-eq PG/kg) | Formulation | $C_{max}$ (μg/mL) | $T_{max}$ (hr) | $AUC_{last}$ (μg × hr/mL) | F (%) |
|---|---|---|---|---|---|---|---|
| Pregabalin | 150 | 52.4 | LYRICA | 21.9 (1.9) | 3.0 (1.2) | 188 (12) | 41 (9) |
| (3a) | 75 | 22.4 | IR | 19.3 (2.4) | 2.0 (1.4) | 163 (25) | 82 (13) |
| (3a) | 75 | 21.7 | SR | 13.5 (3.2) | 3.2 (1.5) | 137 (40) | 70 (16) |
| (3a) | 75 | 22.3 | SR1 | 7.2 (1.2) | 8.0 (6.9) | 104 (16) | 52 (6) |
| (3a) | 69 | 21.1 | SR2 | 5.0 (0.3) | 14.0 (3.5) | 70 (1) | 35 (9) |

Abbreviations: PG = Pregabalin; SD = Standard deviation; $C_{max}$ = Maximum concentration; $T_{max}$ = Time to reach $C_{max}$; $AUC_{last}$ = Area under the concentration vs. time curve from time zero to the last time point with measurable concentration; F = % Bioavailability (based on $AUC_{last}$) relative to $AUC_{inf}$ of intravenous pregabalin at 8 mg/kg in the same monkey.

Figure 9:
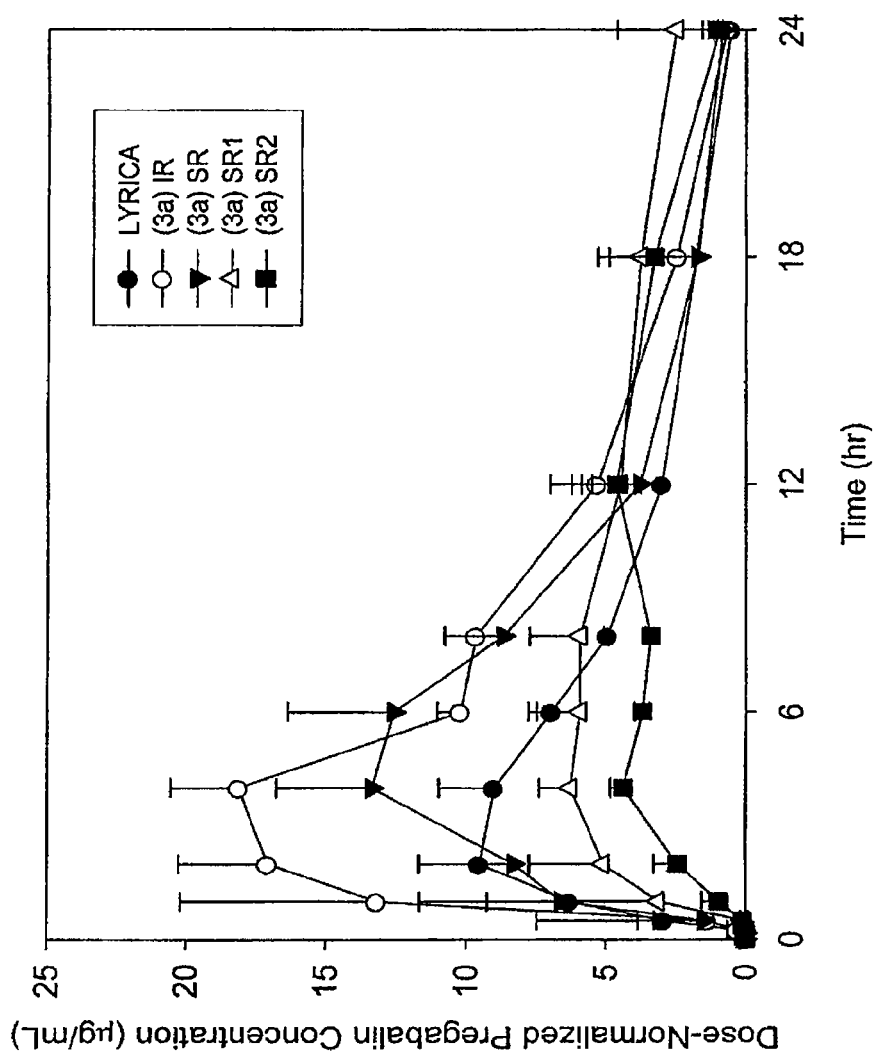
FIG. 9 shows mean (SD) concentrations of pregabalin in blood of monkeys following oral administration of pregabalin or crystalline calcium (3S)-{[(1R)-isobutanoyloxyethoxy]carbonylaminomethyl}-5-methyl-hexanoate hydrate formulations.

FIG. 9 shows the mean (SD) concentration-time profiles of pregabalin in blood after oral dosing of pregabalin or crystalline calcium (3S)-{[(1R)-isobutanoyloxyethoxy]carbonylaminomethyl}-5-methyl-hexanoate hydrate tablet formulations. For comparison, pregabalin concentrations for LYRICA and the SR2 formulation were normalized to 75 mg-eq pregabalin.

Example 15

Clinical Trials for Assessing Efficacy in Managing Perioperative Pain

Based on recent clinical trials performed in patients undergoing various surgical procedures such as total abdominal hysterectomy, laparoscopic hysterectomy, major laparoscopic surgery, and spinal fusion surgery, pregabalin doses of 150 mg to 300 mg administered 1 to 2 hours prior to surgery were effective in reducing pain and reducing opioid use (Reuben et al., *Anesth Analg* 2006, 103(5), 1271-7; Reuben et al., *J Bone and Joint Surgery* 2007, 89, 1343-58; Buvanendran et al., *Anesthesiology* 2007, 107, 358-359; and Jokela, *Pain*

2008, 134, 106-112). Based on these and other studies, it is expected $C_{max}$ and $AUC_{inf}$ values for efficacious doses of pregabalin for perioperative management of acute post-surgical pain are predicted to be in the range of 4.73 to 9.46 µg/mL and 33.2 to 66.3 µg×hr/mL, respectively.

Efficacy in treating and managing pain can be assessed using one or more outcome measures including the Visual Analog Scale (VAS) for pain, the Pain Intensity Scale, the Visual Analog Scale for Anxiety, supplemental opioid consumption, patient global assessment of pain control, cognitive impairment after surgery, and Range of Motion Composite. The Visual Analog Scale (VAS) is a straight line with the left end of the line representing no pain and the right end of the line representing the worst pain.

The Pain Intensity Rating scale is one of several different pain-intensity tools available to qualify pain. Pain intensity can be measured in a numerical format where the individual is asked to identify how much pain they are having by choosing a number from 0 (no pain) to 10 (the worst pain) on a numerical scale. In the VAS Anxiety Scale patients rate anxiety on horizontal line from left to right were 0=no anxiety and 100=worst anxiety. Supplemental Opioid Consumption reflects the amount of supplemental opioid used to control pain during specified time frame. In the Subject Global Assessment of Pain control patients respond at predetermined intervals after surgery how he/she feels regarding pain control. In the Physician Global Assessment of Pain control the physician responds at predetermined intervals after surgery how he/she feels regarding pain control in the patient. Cognitive impairment can be assessed in a post surgical setting by use of the Confusion Assessment Method Rating Scale (CAM) which was developed as a screening instrument based on the DSM-IIIR criteria for non psychiatric physicians in high risk settings. Range of motion assessments may be used to evaluate a patient's ability to flex and extend a particular joint such as the knee.

A multi-center, randomized, double-blind, placebo-controlled, parallel group study of the post-operative analgesic efficacy and safety of pre-operative dosing of crystalline calcium (3S)-{[(1R)-isobutanoyloxyethoxy]carbonylaminomethyl}-5-methyl-hexanoate hydrate in patients undergoing bunionectomy is performed.

Male and female study subjects, approximately 50 in each treatment arm, are randomly assigned in a balanced allocation to receive a single oral dose of crystalline calcium (3S)-{[(1R)-isobutanoyloxyethoxy]carbonylaminomethyl}-5-methyl-hexanoate hydrate or placebo. All patients receive crystalline calcium (3S)-{[(1R)-isobutanoyloxyethoxy]carbonylaminomethyl}-5-methyl-hexanoate hydrate or placebo approximately 1 hour prior to the surgical incision and have access to patient controlled analgesia (PCA) such as morphine after surgery.

Pain intensity reported by patients on the VAS at 2, 4, 6, 12 and 24 hours after surgery, the amount of opioid consumed over 24 hours following surgery, time to first request for rescue PCA pain medication during the 24-hour post-surgical period, and the level of sedation at defined time points after surgery are determined.

Efficacy is assessed by comparing the outcome measures in patients receiving crystalline calcium (3S)-{[(1R)-isobutanoyloxyethoxy]carbonylaminomethyl}-5-methyl-hexanoate hydrate and placebo.

A multi-center, randomized, double-blind, placebo-controlled, parallel group dose-ranging study to evaluate the post-operative analgesic efficacy and safety of peri-operative administration of crystalline calcium (3S)-{[(1R)-isobutanoyloxyethoxy]carbonylaminomethyl}-5-methyl-hexanoate hydrate in patients undergoing primary unilateral total knee arthroplasty is performed.

On the evening before surgery patients are instructed in the use of the 100-mm visual analog scale for pain (VAS Pain) and anxiety (VAS Anxiety). Also during this evening visit the instructions on use of a patient controlled anesthesia (PCA) device are provided. Patients are randomized into one of 5 study arms. Placebo+IV PCA morphine or one of 4 doses of crystalline calcium (3S)-{[(1R)-isobutanoyloxyethoxy]carbonylaminomethyl}-5-methyl-hexanoate hydrate (e.g., 150 mg, 300 mg, 600 mg, or 900 mg, or other appropriate dose or doses)+PCA morphine. On the morning of surgery patients receive crystalline calcium (3S)-{[(1R)-isobutanoyloxyethoxy]carbonylaminomethyl}-5-methyl-hexanoate hydrate or placebo approximately 1 hour prior to the surgical incision. After a defined period in the recovery room, PCA morphine is made available to the patient. Patients receive PCA with morphine at doses of 2.5 mg with a lock-out of 10 min for 24 hours postoperatively. Vicodin (hydrocodone 7.5 mg/acetaminophen 500 g) is made available 24 hours after surgery to replace the PCA morphine and patients continue on 300-mg of crystalline calcium (3S)-{[(1R)-isobutanoyloxyethoxy]carbonylaminomethyl}-5-methyl-hexanoate hydrate q AM for the next 5 days as outpatients. Pain control is evaluated during physical therapy.

VAS for pain intensity at 2, 4, 6, 12, 24 and 48 hours after surgery, categorical pain intensity scores in the AM at 48, 72, 96 and 120 hrs post surgery and immediately before scheduled physical rehabilitation, the amounts of IV opioids (morphine equivalents) used following surgery in 24 hours (time frame of 24 hours), time needed for the first rescue PCA pain medication during the double blind period, the amount of rescue (Vicodin) medication, and the level of sedation at defined time points after surgery are determined. Outcome of the surgical procedure is determined using Knee Function Global Endpoint; Pain with Range of Motion Composite, Knee Function Composite assessments.

Example 16

Animal Model for Assessing Efficacy in Managing Osteoarthritis Pain

The monosodium iodoacetate rat model for osteoarthritis pain can be used to assess the efficacy of crystalline calcium (3S)-{[(1R)-isobutanoyloxyethoxy]carbonylaminomethyl}-5-methyl-hexanoate hydrate in managing osteoarthritis pain.

Sprague-Dawley male rats weighing 220-230 grams are housed singly in wire cages in sanitary ventilated animal rooms with controlled temperature, humidity and regular light cycles. Rodent chow and water are available ad libitum. Animals are acclimated for at least one week before use.

Arthritis is induced by a single intraarticular injection of iodoacetate into the knee joint of anesthetized rats. A 10 mg/mL solution of monosodium iodoacetate is prepared using injectable saline as the vehicle. After appropriate anesthesia each rat is positioned on its back and the left leg is flexed 90 degrees at the knee. The patellar ligament is palpated below the patella and the injection is made into this region. Each rat receives 0.025 mL intra-articular injection into the left knee. After injection of iodoacetate, rats are treated orally with either vehicle or test composition, e.g., crystalline calcium (3S)-{[(1R)-isobutanoyloxyethoxy]carbonylaminomethyl}-5-methyl-hexanoate hydrate and an opioid agonist such as tramadol, tapentadol or oxycodone, in vehicle for 3 weeks or other appropriate time period. Upon termination of the study, the left knees of the euthanized animals are disarticulated ant the tibial plateau imaged. The severity of damage in the images is assessed.

The hyperalgesic response can be assessed using the Hargreaves model. On the first day of the study, each animal is acclimated to the test equipment and thermal hyperalgesia determined using a Hargreaves Plantar Device (infrared radiant heat source) to establish baseline paw withdrawal latency (PWL) values. The baseline PWL values are calculated as the mean of 2 pre-dose values. Animals are fasted overnight prior to dosing. The following day animals are orally dosed with vehicle or test composition. Thirty minutes after dosing, each animal is anesthetized and receives an intraplantar injection of 0.1 mL of a 1.2% solution (w/v) of Carrageenan Viscarin GP 109 and returned to its cage to recover. Four hours post injection, the left hind limb of each rat is assessed for thermal hyperalgesia. The animals are placed into the Hargreaves Plantar Device once again to determine response to the heat stimulus as time to paw withdrawal.

Assessment of punctuate allodynia is evaluated by application of von Frey hairs in ascending order of force to the plantar surface of the hind paws. Dynamic allodynia is assessed by lightly stroking the plantar surface of the hind paw with a cotton bud. Paw withdrawal thresholds (PWT) to von Frey hairs and withdrawal latencies to cotton bud stimulus are assessed in the same group of animals on various days post-intraarticular injection.

The effect of joint damage on the weight distribution through the right (arthritic) and left (untreated) knee is assessed using an incapacitance tester, which measures weight distribution on the two hind paws.

To determine the inhibitory effects of test composition and opioid agonist on punctuate allodynia and weight bearing deficit, compounds are administered 14 days (or other appropriate time) post-intraarticular injection having established stable baseline PWT and weight bearing deficits prior to drug administration. Animals are administered (on separate days) with either vehicle or test compound(s) and changes from baseline assessed for up to 3 hours or other appropriate duration.

Example 17

Animal Model for Assessing Efficacy in Managing Muscle Pain

Adult male Sprague-Dawley rats weighing 250-300 g are used. To induce muscle pain, recombinant rat TNF diluted in 0.9% NaCl at a concentration of 1 µg in 50 µL is injected bilaterally either into the gastrocnemius or into the biceps brachii muscle. The time course of TNF-induced hyperalgesia is determined in pilot experiments. After injection into the M. gastrocnemius, pressure hyperalgesia is maximal after about 18 hours. After injection of 1 µg TNF into the M. biceps brachii, grip strength reduction is maximal at about 6 h.

Mechanical withdrawal thresholds to muscle pressure are measured with an algesimeter. Rats are allowed to crawl into a sock which helps the rat to relax. The hind limbs are positioned such that an increasing pressure could be applied onto the gastrocnemius muscle (maximum 250 g). The pressure needed to elicit withdrawal is recorded. Both hind limbs are tested ten times (interstimulus interval of >30 s) and means of all withdrawal thresholds are calculated for each rat.

Grip strength of the fore limbs is tested with a digital grip force meters. A rat is positioned to grab the grid with the fore limbs and is gently pulled so that the grip strength can be recorded. Means of ten trials are calculated. Hyperalgesia is assumed if the means of the tests before and after TNF injection are significantly different and if the difference to baseline is at least 1 g for the withdrawal threshold to pressure and at least 0.5 g for grip strength.

Rats undergo behavioral testing on three consecutive days before TNF injections to accustom the animals to the testing procedure. Values obtained on the third day are used as a baseline. Separate groups of rats are then either injected with TNF bilaterally into the M. gastrocnemius and tested for pressure hyperalgesia 18 h later, or injected with TNF bilaterally into the M. biceps brachii and tested for grip strength of the fore limbs 6 h later. Crystalline calcium (3S)-{[(1R)-isobutanoyloxyethoxy]carbonylaminomethyl}-5-methyl-hexanoate hydrate is then administered and the behavioral tests repeated at appropriate time intervals following administration.

All rats are monitored for general behavior after drug administration. Sedation ataxia, or other abnormalities of gait, interaction with other animals and feeding behavior are observed.

Comparative Example 1

Figure 3:
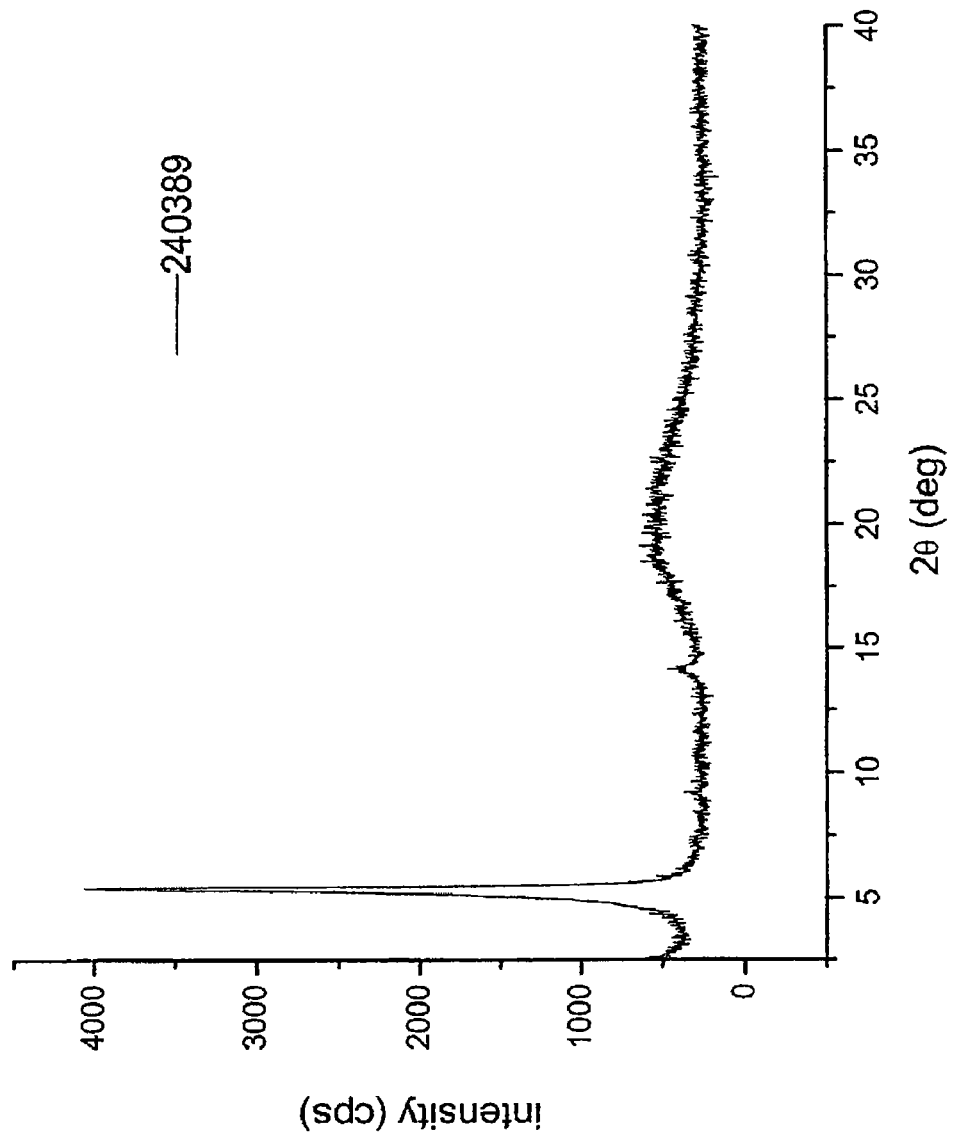
FIG. 3 shows an X-ray powder diffractogram of calcium (3S)-{[(1R)-isobutanoyloxyethoxy]carbonylaminomethyl}-5-methyl-hexanoate anhydrous crystallized from acetone/hexane.

Crystallization of Calcium (3S)-{[(1R)-Isobutanoyloxyethoxy]carbonylaminomethyl}-5-Methyl-Hexanoate From Non-Aqueous Solvents From Acetone-Hexane:
Calcium (3S)-{[(1R)-isobutanoyloxyethoxy]carbonylaminomethyl}-5-methyl-hexanoate (3) (500 mg) was dissolved in 2 mL of acetone then hexane (9 mL) was added as an anti-solvent. The suspension was warmed to 40° C. to form a clear solution. The solution was cooled to room temperature and allowed to stand overnight to permit crystallization. The product was filtered and dried in a vacuum dessicator to afford (3) (338 mg, 67% recovery) as a white, crystalline solid. m.p. 103.3-117.0° C. An X-ray powder diffractogram of (3) prepared according to this method, obtained as described in Example 10, is shown in FIG. 3 and is characterized as a mesophasic anhydrate.

From THF-Hexane:
Calcium (3S)-{[(1R)-isobutanoyloxyethoxy]carbonylaminomethyl}-5-methyl-hexanoate (3) (200 mg) was dissolved in 1 mL of THF to form a clear solution, then hexane (9 mL) as an anti-solvent was added to form a suspension. The suspension was warmed to 45° C. to give a clear solution. The solution was first cooled to room temperature and then to 4° C. to allow crystals to form. The product was filtered and dried in a vacuum dessicator to afford (3) (78 mg, 39% recovery) as a white, crystalline solid. m.p. 95.5-113.7° C. An X-ray powder diffractogram of (3) prepared according to this method, obtained as described in Example 10, was similar to that of FIG. 3 and is characterized as a mesophasic anhydrate.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. The compound crystalline calcium (3S)-{[(1R)-isobutanoyloxyethoxy]carbonylaminomethy}-5-methyl-hexanoate hydrate, which exhibits characteristic scattering angles (2α) at least at 5.1°±0.2°, 7.3°±0.2°, 8.0°±0.2°, 11.6°±0.2° and 16.3°±0.2° in an X-ray powder diffractogram measured using Cu—Kα radiation.

2. The compound of claim 1, comprising from 1 mole water per mole of the compound to 3 moles water per mole of the compound.

3. The compound of claim 1, comprising from 2 wt % water to 5 wt % water.

4. The compound of claim 1, which exhibits a melting point range from 107° C. to 111° C.

5. The compound of claim 1, wherein the compound is crystalline calcium 3-({[(1R)-1-(2-methylpropanoyloxy)ethoxy]-carbonylamino}methyl)(3S)-5-methylhexanoic acid monohydrate.

6. A pharmaceutical composition comprising the compound of claim 1 and a pharmaceutically acceptable vehicle.

7. The pharmaceutical composition of claim 6, wherein the pharmaceutical composition is a sustained release oral dosage formulation.

8. The pharmaceutical composition of claim 6, comprising an agent chosen from an opioid agonist, a selective serotonin re-uptake inhibitor, and a selective noradrenaline re-uptake inhibitor.

9. The pharmaceutical composition of claim 6, comprising an opioid agonist.

10. The pharmaceutical composition of claim 9, wherein the opioid agonist is chosen from tramadol, tapentadol, and oxycodone.

11. The pharmaceutical composition of claim 9, wherein the ratio of the amount of compound of claim 1 to the amount of opioid agonist in the pharmaceutical composition is from 1:4 to 4:1.

12. The pharmaceutical composition of claim 9, wherein the pharmaceutical composition is a sustained release oral dosage formulation.

13. The pharmaceutical composition of claim 12, wherein the sustained release oral dosage formulation comprises:
    50 mg to 1200 mg of the compound of claims 1; and
    10 mg to 400 mg of the opioid agonist.

14. A method of preparing the compound crystalline calcium (3S)-{[(1R)-isobutanoyloxyethoxy]carbonylaminomethyl}-5-methyl-hexanoate hydrate, which exhibits characteristic scattering angles (2α) at least at 5.1°±0.2°, 7.3°±0.2°, 8.0°±0.2°, 11.6°±0.2° and 16.3°±0.2° in an X-ray powder diffractogram measured using Cu—Kα radiation by steps comprising:
    providing a solution comprising calcium (3S)-{[(1R)-isobutanoyloxyethoxy]carbonylaminomethyl}-5-methyl-hexanoate, water, and a water-miscible solvent; and
    adjusting the temperature of the solution to provide crystalline calcium (3S)-{[(1R)-isobutanoyloxyethoxy]carbonylaminomethy}-5-methyl-hexanoate hydrate.

15. The method of claim 14, wherein the water-miscible solvent is chosen from ethanol and isopropanol.

16. The method of claim 14, wherein the solution comprises water in an amount ranging from about 40 v/v % to about 75 v/v %.

17. The method of claim 14, wherein the compound is prepared by steps comprising:
    providing a first solution comprising calcium (3S)-{[(1R)-isobutanoyloxyethoxy]carbonylaminomethyl}-5-methyl-hexanoate and an alcoholic solvent;
    adding de-ionized water to the first solution to provide a mixture;
    adjusting the temperature of the mixture to provide a second solution; and
    adjusting the temperature of the second solution to provide crystalline calcium (3S)-{[(1R)-isobutanoyloxyethoxy]carbonylaminomethyl}-5-methyl-hexanoate hydrate.

18. The method of claim 17, wherein the alcoholic solvent is chosen from ethanol and isopropanol.

19. A method of managing chronic pain in a patient comprising administering to a patient in need of such treatment a pharmaceutical composition comprising:
    the compound crystalline calcium (3S)-{[(1R)-isobutanoyloxyethoxy]carbonylaminomethyl}-5-methyl-hexanoate, which exhibits characteristic scattering angles (2α) at least at 5.1°±0.2°, 7.3°±0.2°, 8.0°±0.2°, 11.6°±0.2° and 16.3°±0.2° in an X-ray powder diffractogram measured using Cu—Kα;
    an agent chosen from an opioid agonist, a selective serotonin re-uptake inhibitor, and a selective noradrenaline re-uptake inhibitor; and
    a pharmaceutically acceptable vehicle.

20. The method of claim 19, wherein the agent is an opioid agonist.

21. The method of claim 19, wherein the opioid agonist is chosen from tramadol, tapentadol, and oxycodone.

* * * * *

UNITED STATES PATENT AND TRADEMARK OFFICE
CERTIFICATE OF CORRECTION

PATENT NO. : 8,258,179 B2  
APPLICATION NO. : 12/962472  
DATED : September 4, 2012  
INVENTOR(S) : Fenmei Yao et al.

Page 1 of 1

It is certified that error appears in the above-identified patent and that said Letters Patent is hereby corrected as shown below:

In column 56, at line 63, delete "tanoyloxyethoxy]carbonylaminomethy }-5-methyl-hex-" and insert -- tanoyloxyethoxy]carbonylaminomethyl}-5-methyl-hex- --.

In column 57, at line 7, delete "range from 107 °C. to 111 °C." and insert -- range from 107 °C to 111 °C. --.

In column 57, at line 35, delete "50 mg to 1200 mg of the compound of claims 1; and" and insert -- 50 mg to 1200 mg of the compound of claim 1; and --.

In column 58, at line 6, delete "bonylaminomethy }-5-methyl-hexanoate hydrate." and insert -- bonylaminomethyl}-5-methyl-hexanoate hydrate. --.

In column 58, at line 34, delete "togram measured using Cu-Kα;" and insert -- togram measured using Cu-Kα radiation; --.

Signed and Sealed this  
Twelfth Day of March, 2013

Teresa Stanek Rea  
*Acting Director of the United States Patent and Trademark Office*